(12) United States Patent
Hansel et al.

(10) Patent No.: US 12,178,415 B2
(45) Date of Patent: Dec. 31, 2024

(54) AIRWAY SAMPLING DEVICE AND ASSOCIATED METHODS

(71) Applicants: Hunt Developments Ltd., Midhurst (GB); Imperial College Innovations Limited, London (GB)

(72) Inventors: Trevor T Hansel, Paddington (GB); Toby Hunt, Midhurst (GB); Trevor Hunt, Midhurst (GB); Duncan Hunt, Chichester (GB)

(73) Assignees: Hunt Developments (UK) Ltd., West Sussex (GB); Imperial College Innovations Limited, London (GB)

( * ) Notice: Subject to any disclaimer, the term of this patent is extended or adjusted under 35 U.S.C. 154(b) by 917 days.

(21) Appl. No.: 16/973,864

(22) PCT Filed: Jun. 11, 2019

(86) PCT No.: PCT/GB2019/051617
§ 371 (c)(1),
(2) Date: Dec. 10, 2020

(87) PCT Pub. No.: WO2019/239122
PCT Pub. Date: Dec. 19, 2019

(65) Prior Publication Data
US 2021/0177384 A1    Jun. 17, 2021

(30) Foreign Application Priority Data

Jun. 11, 2018  (GB) ........................ 1809581

(51) Int. Cl.
*A61B 10/00*   (2006.01)
*A61B 1/07*    (2006.01)
*G01N 1/40*    (2006.01)

(52) U.S. Cl.
CPC ............ *A61B 10/0051* (2013.01); *A61B 1/07* (2013.01); *G01N 1/4055* (2013.01); *A61B 2010/009* (2013.01); *G01N 2001/4061* (2013.01)

(58) Field of Classification Search
CPC . A61B 10/0051; A61B 1/07; A61B 2010/009; A61B 10/00; A61B 2010/0087;
(Continued)

(56) References Cited

U.S. PATENT DOCUMENTS

| 8,551,016 B2 | 10/2013 | Slowey et al. |
| 2001/0037055 A1 | 11/2001 | Khatchatrian et al. |

(Continued)

FOREIGN PATENT DOCUMENTS

| WO | 9502996 A1 | 2/1995 |
| WO | 2009068864 A1 | 6/2009 |
| WO | 2011094745 A2 | 8/2011 |

OTHER PUBLICATIONS

Beale, Janine, et al.; "Rhinovirus-induced IL-25 in asthma exacerbation drives type 2 immunity and allergic pulmonary inflammation"; www.ScienceTranslationalMedicine.org; Oct. 1, 2014; vol. 6, Issue 256 256ra134; 12 pages; https://www.science.org/doi/10.1126/scitranslmed.3009124.

(Continued)

*Primary Examiner* — Suman K Nath
(74) *Attorney, Agent, or Firm* — Kenneth E. Horton; Barnes & Thornburg LLP

(57) ABSTRACT

The present application discloses a variety of airway sampling devices and associated methods. According to an embodiment, an airway sampling device for taking a sample from a subject's airway is provided with a handle to be gripped by a user when taking the sample and a sampling head carried by the handle, the sampling head comprising a (Continued)

cavity with an opening for entry by the sample and a sample collection membrane located within the cavity for receiving the sample.

23 Claims, 41 Drawing Sheets

(58) Field of Classification Search
CPC .............. A61B 13/00; G01N 1/4055; G01N 2001/4061
See application file for complete search history.

(56) References Cited

U.S. PATENT DOCUMENTS

| | | | |
|---|---|---|---|
| 2002/0106809 | A1 | 8/2002 | Cesarczyk |
| 2004/0019301 | A1* | 1/2004 | Wong .................. G01N 33/558 600/584 |
| 2016/0121322 | A1* | 5/2016 | Fuller ................ A61B 10/0051 422/417 |
| 2017/0049423 | A1* | 2/2017 | Mombrun .......... A61B 10/0045 |

OTHER PUBLICATIONS

Chawes, Bo L. K., MD, et al.; "A novel method for assessing unchallenged levels of mediators in nasal epithelial lining fluid"; J Allergy Clin Immunol; June 210; vol. 125, No. 6; pp. 1387-1389.e3.
Jackson, David J., et al.; "Interleukin-18 Is Associated With Protection Against Rhinovirus-Induced Colds and Asthma Exacerbations"; Clinical Infectious Diseases; May 15, 2015; vol. 60; pp. 1528-1531; https://doi.org/10.1093/cid/civ062.
Jayaraman, A.; "IL-15 complexes induce NK- and T-cell responses independent of type I IFN signaling during rhinovirus infection"; MucosalImmunology; Sep. 2014; vol. 7, No. 5; pp. 1151-1164.
Scadding, Guy W., et al.; "Optimisation of grass pollen nasal allergen challenge for assessment of clinical and immunological outcomes"; Journal of Immunological Methods; 2012; vol. 384; pp. 25-32; Doi:10.1016/j.iim.2012.06.013.
Valenta, Rudolf; "Mucosal Lining Fluid Biomarkers in Asthma: Basis for Rational Use of New Targeted Therapies?"; 2017; vol. 19; pp. 12-13; http://dx.doi.org/10.1016/j.ebiom.2017.04.016.
Cohen, J., et al.; "Ciclesonide improves measures of small airway involvement in asthma"; European Respiratory Journal; 2018; vol. 31, No. 6; pp. 1213-1220; DOI: 10.1183/09031936.00082407.
Ishizaka, Akitoshi, MD; "New bronchoscopic microsample probe to measure the biochemical constituents in epithelial lining fluid of patients with acute respiratory distress syndrome"; Crit Care Med; 2001; vol. 29, No. 4; pp. 896-898.
Owlstone Medical; The home of Breath Biopsy®; print out of website retrieved from Internet Achieve Wayback Machine <https://web.archive.org/web/20180310053829/https://www.owlstonemedical.com/>, dated Mar. 3, 2018; 8 pages.
Deton; The Deton Cough Collector; https://vimeo.com/182138724.
Mucosal Diagnostics; Nasosorption™ FX.i; https://www.mucosaldiagnostics.com/; available at least as early as Jun. 15, 2017; 5 pages.
Images of mouth and nasopharynx; Image 1 retrieved from https://www.netterimages.com/mouth-labeled-general-anatomy-frank-h-netter-8648.html ; Image 2 retrieved from https://www.fotosearch.com/LIF001/9879h_hr/ ; Image 3 retrieved from https://photos.com/featured/cross-section-biomedical-illustration-of-mirror-laryngoscopy-dorling-kindersley.html; all images available at least as early as Jan. 4, 2018.
Images of Two External Cough Collection Method; Image 1 retrieved from https://www.condair.co.uk/humidity-health-wellbeing/dry-air-and-airborne-infection ; Image 2 retrieved from https://ar.javamem.com/pictures/purulent-sputum-color ; Image 3 retrieved from https://www.slideshare.net/doctorrao/bordetella (image on slide 39 of 54); Image 4 not found; all images available at least as early as Apr. 16, 2018.

Getty Image; Spirometry—Lung Function Testing ; Link to image not found; image available at least as early as Apr. 16, 2018.
Pentax Nasolaryngoscope; Image of Video rhino-pharyngo-laryngoscope VNL-1570STK; Image retrieved from https://www.medicalexpo.com/prod/pentax/product-70880-721899.html ; image available at least as early as May 25, 2017.
Image of Flexible Fibreoptic Laryngoscopy; Image retrieved from https://fortworthent.net/ear-nose-throat/laryngopharyngeal-reflux-disease-lpr/flexible-fiberoptic-laryngoscopy-2/ ; image available at least as early as Apr. 16, 2018.
Image of External Collection of Sputum; Image retrieved from https://www.nursingtimes.net/clinical-archive/assessment-skills/specimen-collection-4-procedure-for-obtaining-a-sputum-specimen-11-09-2017/ ; image available at least as early as Apr. 16, 2018; print out of website retrieved from Internet Achieve Wayback Machine < http:/web.archive.org/web/20200822051309/https://www.nursingtimes.net/clinical-archive/assessment-skills/specimen-collection-4-procedure-for-obtaining-a-sputum-specimen-11-9-2017/ > , dated Aug. 22, 2020.
Images of Dental Mirrors; Image 1 retrieved from https://www.amazon.ca/DISPOSABLE-Price-Club-Dental-Supplies/dp/B005EIQJJO ; Image 2 retrieved from https://www.amazon.com/Mirror-Lighted-Dental-Hygiene-Personal/dp/B07KS24YM1 ; Image 3 retrieved from https://basicmedicalkey.com/laryngoscopy-and-endotracheal-intubation/ ; Image 4 (two images) retrieved from https://www.promiseedental.com/other-products/ ; all image available at least as early as May 25, 2017.
Images of Cervical Sampling; Image 1 retrieved from https://www.gov.uk/government/publications/cervical-screening-description-in-brief/cervical-screening-helping-you-decide--2 ; Image 2 retrieved from https://gynsurgicalsolutions.com/patients/treatment-options/myosure/procedure-steps-and-components/ ; all image available at least as early as May 25, 2017.
Hogan, Simon P., et al.; "Eosinophils: Biological Properties and Role in Health and Disease"; Clinical and Experimental Allergy; 2008; Blackwell Publishing Ltd; https://doi.org/10.1111/j.1365-2222.2008.02958.x ; pp. 709-750.
Rosenberg, Helene F., et al. ; "Eosinophils: changing perspectives in health and disease"; Nature Review | Immunology; Jan. 2013; vol. 13; Macmillan Publishers Limited; pp. 9-22.
Horn, Barry R., et al.; "Total Eosinophil Counts In The Management Of Bronchial Asthma"; The New England Journal Of Medicine; May 29, 1975; vol. 292, No. 22; Massachusetts Medical Society; pp. 1152-1155.
Bousquet, Jean, M.D., Ph.D., et al.; "Eosinophilic Inflammation In Asthma"; The New England Journal of Medicine; Oct. 11, 1990; vol. 323, No. 15; Massachusetts Medical Society; pp. 1033-1039.
Tefferi, Ayalew, MD; "Blood Eosinophilia: A New Paradigm in Disease Classification, Diagnosis, and Treatment"; Mayo Clin Proc.; Jan. 2005; vol. 80, Issue 1; pp. 75-83.
Pavord, Ian D.; "Mepolizumab for severe eosinophilic asthma (DREAM): a multicentre, double-blind, placebo-controlled trial"; The Lancet; Aug. 18, 2012; vol. 380; pp. 651-659.
Ortega, Hector G., M.D., Sc.D., et al.; "Mepolizumab Treatment in Patients with Severe Eosinophilic Asthma"; The New England Journal of Medicine; Sep. 8, 2014; Massachusetts Medical Society; DOI: 10.1056/NEJMoa1403290; 10 pages.
Bel, Elisabeth H., M.D., Ph.D., et al.; "Oral Glucocorticoid-Sparing Effect of Mepolizumab in Eosinophilic Asthma"; The New England Journal of Medicine; Sep. 25, 2014; vol. 371, No. 13; Massachusetts Medical Society; DOI: 10.1056/NEJMoa1403291; pp. 1189-1197.
Castro, Mario; "Benralizumab, an anti-interleukin 5 receptor a monoclonal antibody, versus placebo for uncontrolled eosinophilic asthma: a phase 2b randomised dose-ranging study"; The Lancet, Respiratory Medicine; Oct. 9, 2014; Elsevier Ltd.; https://doi.org/10.1016/S2213-2600(14)70201-2; 12 pages.
Busse, William, MD, et al.; "High eosinophil count: A potential biomarker for assessing successful omalizumab treatment effects"; The Journal of Allergy and Clinical Immunology; Apr. 15, 2013; Elsevier Inc.; https://doi. org/10.1016/j.jaci.2013.02.032; pp. 485-486.
Chung, Kian Fan, et al.; "International ERS/ATS guidelines on definition, evaluation and treatment of severe asthma"; Task Force

(56) References Cited

OTHER PUBLICATIONS

Report, ERS/ATS Guidelines on Severe Asthma; 2014; ERS; DOI: 10.1183/09031936.00202013; pp. 343-373.
Wempe, Johan B., MD, et al.; "Blood eosinophil numbers and activity during 24 hours: Effects of treatment with budesonide and bambuterol"; J Allergy Clin Immunol; Nov. 1992; vol. 90, No. 5; pp. X-765.
Sand, Kristin L., et al.; "Effects of exercise on leukocytosis and blood hemostasis in 800 healthy young females and males"; World Journal of Experimental Medicine; Feb. 20, 2013; vol. 3, Issue 1; Baishideng; doi:10.5493/wjem.v3.1.11; pp. 11-20.
Spector, Sheldon Laurence, et al.; "Is a Single Blood Eosinophil Count a Reliable Marker for "Eosinophilic Asthma?""; Journal of Asthma; 2012; Informa Healthcare USA, Inc.; DOI: 10.3109/02770903.2012.713428; pp. 807-810.
Horvath, J. Hunt, et al.; "Exhaled breath condensate: methodological recommendations and unresolved questions"; European Respiratory Journal; 2005; vol. 26, No. 3; ERS Journals Ltd.; DOI: 10.1183/09031936.05.00029705; pp. 523-548.
Effros, Richard M., et al.; "Dilution of Respiratory Solutes in Exhaled Condensates"; American Journal of Respiratory and Critical Care Medicine; 2002; vol. 165; DOI: 10.1164/rccm.2101018; pp. 663-669.
Effros, Richard M., et al.; "The Effects of Volatile Salivary Acids and Bases on Exhaled Breath Condensate pH"; American Journal of Respiratory and Critical Care Medicine; 2006; vol. 173.; pp. 386-392.
Effros, Richard M., et al.; "Exhaled Breath Condensates: Analyzing the Expiratory Plume"; American Journal of Respiratory and Critical Care Medicine; vol. 185, Issue 8; Apr. 15, 2012; American Thoracic Society; DOI: 10.1164/rccm.201109-1702ED; pp. 803-804.
Nicolaou, Nicolaos C.; "Exhaled Breath Condensate pH and Childhood Asthma, Unselected Birth Cohort Study"; American Journal of Respiratory and Critical Care Medicine; 2006; vol. 174; pp. 254-259.
Liu, Lei, PhD; "Determinants of Exhaled Breath Condensate pH in a Large Population With Asthma"; Chest; Feb. 2011; American College of Chest Physicians; pp. 328-336.
Wagener, Ariane H.; "Toward Composite Molecular Signatures in the Phenotyping of Asthma"; Ann Am Thorac Soc; Dec. 2013; vol. 10; American Thoracic Society; DOI: 10.1513/AnnalsATS.201302-035AW; pp. S197-S205.
Bikov, Andras; "Standardised exhaled breath collection for the measurement of exhaled volatile organic compounds by proton transfer reaction mass spectrometry"; BMC Pulmonary Medicine; 2013; Bikov et al; https://bmcpulmmed.biomedcentral.com/articles/10.1186/1471-2466-13-43; 7 pages.
Van der Schee, Marc P., et al.; "Altered exhaled biomarker profiles in children during and after rhinovirus-induced wheeze"; Eur Respir J; 2015; ERS; DOI: 10.1183/09031936.00044414; pp. 440-448.
Van der Schee, Marc Philippe, MD, et al.; "Breathomics in Lung Disease"; Chest; Jan. 2015; pp. 224-231.
Brown, H. Morrow, et al.; "Treatment of Chronic Asthma With Prednisolone Significance of Eosinophils in the Sputum"; Original Articles; Dec. 13, 1958; pp. 1245-1247.
Finlayson, R., M.A., M.D.; "The Vicissitudes of Sputum Cytology"; pp. 24-35.
Djukanovic, R., et al.; "Standardised methodology of sputum induction and processing"; European Respiratory Journal; 2002; DOI: 10.1183/09031936.02.00000102; 2 pages.
Green, Ruth H., et al.; "Asthma exacerbations and sputum eosinophil counts: a randomised controlled trial"; The Lancet; Nov. 30, 2002; vol. 360; The Lancet Publishing Group; pp. 1715-1721.
Moore, Wendy C., MD, et al.; "Sputum neutrophil counts are associated with more severe asthma phenotypes using cluster analysis"; The Journal of Allergy and Clinical Immunology; Jun. 2014; vol. 133, No. 6; https://doi.org/10.1016/j.iaci.2013.10.011; pp. 1557-1563.

Hastie, Annette T., PhD, et al.; "Analyses of asthma severity phenotypes and inflammatory proteins in subjects stratified by sputum granulocytes"; J Allergy Clin Immunol; May 2010; vol. 125, No. 5; doi: 10.1016/j.iaci.2010.02.008; pp. 1028-1036.
Hastie, Annette T., PhD, et al.; "Biomarker surrogates do not accurately predict sputum eosinophil and neutrophil percentages in asthmatic subjects"; J Allergy Clin Immunol; Jul. 2013; vol. 132, No. 1; https://doi.org/10.1016/j.iaci.2013.03.044; pp. 72-80.
Schleich, Florence Nicole, et al.; "Importance of concomitant local and systemic eosinophilia in uncontrolled asthma"; Eur Respir J; 2014; DOI: 10.1183/09031936.0020181; pp. 97-108.
Schleich, Florence N., et al.; "Distribution of sputum cellular phenotype in a large asthma cohort: predicting factors for eosinophilic vs neutrophilic inflammation"; BMC Pulmonary Medicine; 2013; BioMed Central; https://bmcpulmmed.biomedcentral.com/articles/10.1186/1471-2466-13-11; 8 pages.
Wagener, A. H., et al.; "External validation of blood eosinophils, FENO and serum periostin as surrogates for sputum eosinophils in asthma"; Thorax; 2015; doi:10.1136/thoraxjnl-2014-205634; pp. 115-120.
Keatings, V., et al.; "Analysis of fluid-phase mediators"; Eur Respir J; 2002; ERS Journals Ltd.; DOI: 10.1183/09031936.02.00002402; pp. 24-39.
Kelly, Margaret M., et al.; "Induced sputum: Validity of fluid-phase IL-5 measurement"; J Allergy Clin Immunol; Jun. 2000; vol. 105, No. 6, Part 1; doi:10.1067/mai.2000.106375; pp. 1162-1168.
Kelly, M.M., et al.; "Increased detection of interleukin-5 in sputum by addition of protease inhibitors"; European Respiratory Journal; 2001; pp. 685-691.
Lü, Fabien X., et al.; "Novel nasal secretion collection method for the analysis of allergen specific antibodies and inflammatory biomarkers"; Journal of Immunological Methods; Apr. 30, 2010; vol. 356, Issues 1-2; Elsevier B.V.; https://doi.org/10.1016/j.jim.2010.03.004; pp. 6-17.
Chawes, Bo L. K., MD, et al.; "A novel method for assessing unchallenged levels of mediators in nasal epithelial lining fluid"; J Allergy Clin Immunol; Jun. 2010; vol. 125, No. 6; pp. 1387-1389. e3.
Følsgaard, Nilofar V., et al.; "Neonatal Cytokine Profile in the Airway Mucosal Lining Fluid Is Skewed by Maternal Atopy"; American Journal of Respiratory and Critical Care Medicine; 2012; vol. 185; pp. 275-280.
Nicholson, Grant C., BSc, et al.; "The effects of an anti-IL-13 mAb on cytokine levels and nasal symptoms following nasal allergen challenge"; J Allergy Clin Immunol; Oct. 2011; vol. 128, No. 4; pp. 800-807.e9.
Scadding, Guy W., et al.; "Optimisation of grass pollen nasal allergen challenge for assessment of clinical and immunological outcomes"; Journal of Immunological Methods; Oct. 2012; vol. 384; pp. 25-32; https://doi.org/10.1016/j.jim.2012.06.013.
Dhariwal J, Kitson J, Jones RE, Nicholson, et al. (2015) Nasal Lipopolysaccharide Challenge and Cytokine Measurement Reflects Innate Mucosal Immune Responsiveness. PLos One 10(9): e0135363. doi:10.1371/journal.pone.0135363.
Jayaraman, A., et al.; "IL-15 complexes induce NK- and T-cell responses independent of type I IFN signaling during rhinovirus infection"; MucosalImmunology; Sep. 2014; vol. 7, No. 5; pp. 1151-1164.
Beale, Janine, et al.; "Rhinovirus-induced IL-25 in asthma exacerbation drives type 2 immunity and allergic pulmonary inflammation"; www.ScienceTranslationalMedicine.org; Oct. 1, 2014; vol. 6 Issue 256 256ra134; 11 pages.
Jackson, David J., et al.; "IL-33-Dependent Type 2 Inflammation during Rhinovirus-induced Asthma Exacerbations In Vivo"; American Journal of Respiratory and Critical Care Medicine; Dec. 15, 2014; vol. 190, No. 12; pp. 1373-1382.
Jackson, David J., et al.; "Interleukin-18 Is Associated With Protection Against Rhinovirus-Induced Colds and Asthma Exacerbations"; Clinical Infectious Diseases; 2015; 60(10); pp. 1528-1531; DOI: 10.1093/cid/civ062 Leaker, BR., et al: "The nasal mucosal late allergic reaction to grass pollen involves type 2 inflammation (IL-5

(56) References Cited

OTHER PUBLICATIONS and IL-13), the inflammasome (IL-1b), and complement"; MucosalImmunology; Mar. 2, 2017; vol. 10, No. 2; www.nature.com/mi ; pp. 408-420.

Thwaites, Ryan S., PhD, et al.; "Biphasic activation of complement and fibrinolysis during the human nasal allergic response"; J Allergy Clin Immunol; May 2018; vol. 141, No. 5; pp. 1892-1895.e6.

Hansel, Trevor T., et al.; "A Comprehensive Evaluation of Nasal and Bronchial Cytokines and Chemokines Following Experimental Rhinovirus Infection in Allergic Asthma: Increased Interferons (IFN-γ and IFN-λ) and Type 2 Inflammation (IL-5 and IL-13)"; EBioMedicine; 2017; vol. 19; pp. 128-138; http:/dx.doi.org/10.1016/j.ebiom.2017.03.033.

Thwaites, Ryan S., et al.; "Nasosorption as a Minimally Invasive Sampling Procedure: Mucosal Viral Load and Inflammation in Primary RSV Bronchiolitis"; The Journal of Infectious Diseases; Apr. 15, 2017; pp. 1240-1244.

\* cited by examiner

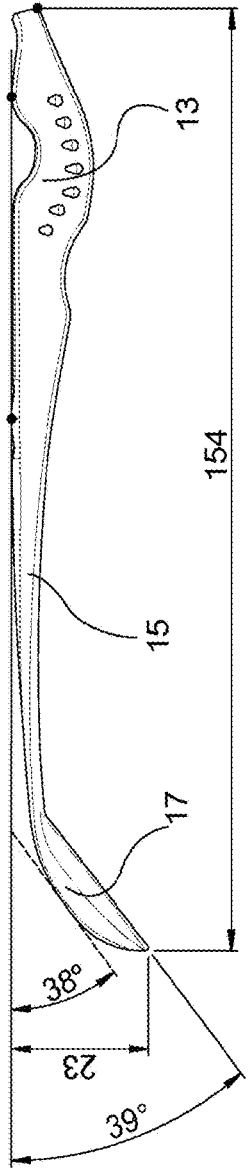
Figure 7C
Figure 7D
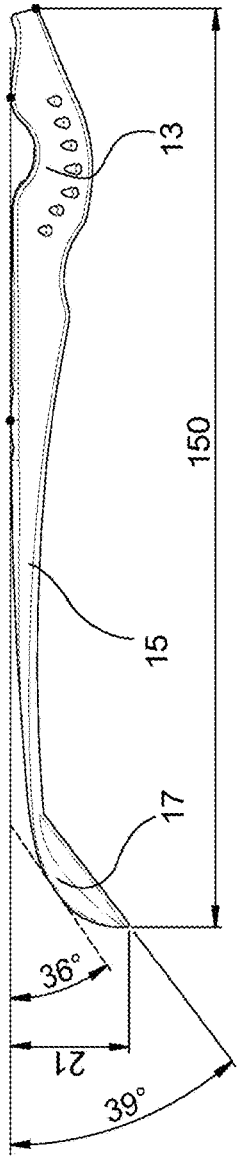
Figure 7E
Figure 7F
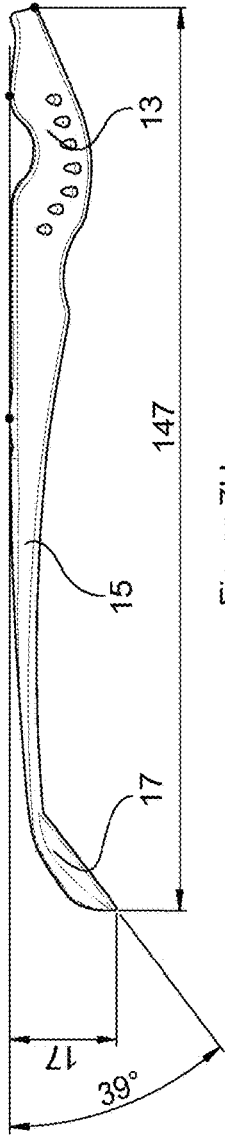
Figure 7G
Figure 7H

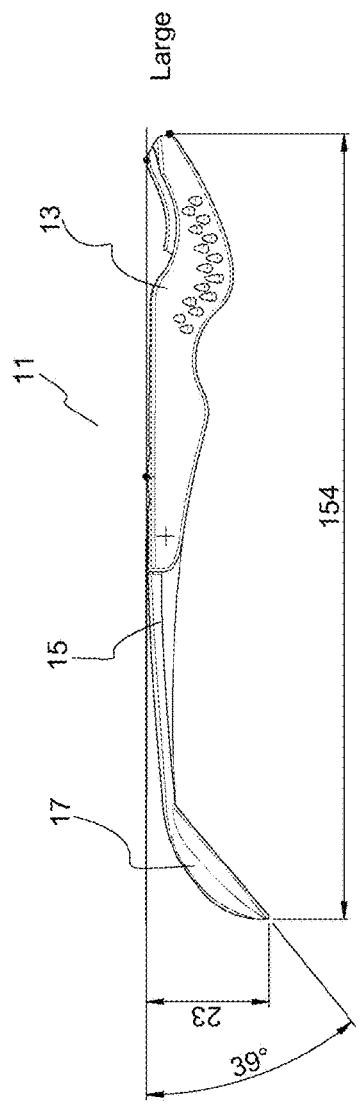
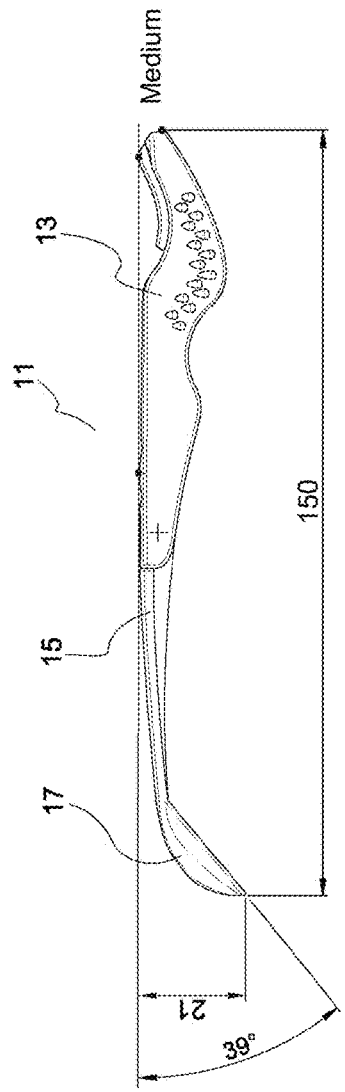
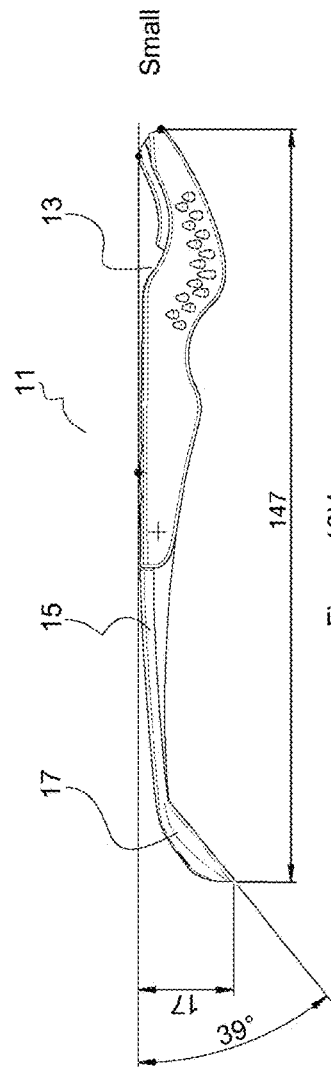
Figure 18D Figure 18F Figure 18H
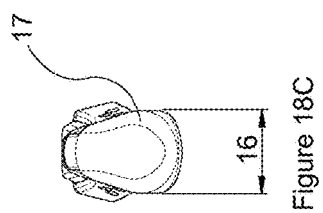
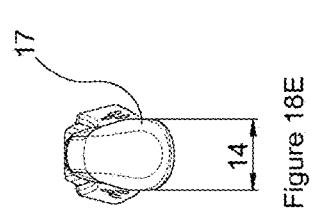
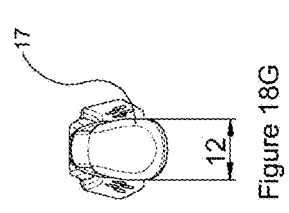
Figure 18C Figure 18E Figure 18G

AIRWAY SAMPLING DEVICE AND ASSOCIATED METHODS

FIELD OF THE INVENTION

The present invention relates to an airway sampling device and associated methods. In particular, embodiments of the present invention seek to provide a non-invasive lower airway mucosal lining fluid sampling device and associated methods.

BACKGROUND OF THE INVENTION

Current methods to monitor inflammation in the airways utilise blood samples, exhaled breath samples, sputum samples, nasal samples and samples obtained during invasive bronchoscopy.

However, various problems are associated with these existing respiratory sampling techniques, and overall there is failure of the prior art when measuring inflammation with non-invasive sampling methods (blood, breath, sputum and nasal methods) when studying lung diseases. The following takes the example of measuring inflammation in asthma in order to illustrate the range of problems with blood, breath, sputum and nasal samples; but these samples are deficient in a range of lung diseases, and not merely asthma.

Blood analysis: blood sampling is from a site too distant from the airways; blood is influenced by many organs through the circulation around the body, and there is considerable dilution in a volume of approximately 5 L. In modern clinical practice in asthma there is a tendency to use the blood eosinophil count to assess the level of airway inflammation. This is reflected in a minimum level of blood eosinophils being required before selection of asthmatic patients for a monoclonal antibody therapy (anti-interleukin-5 or anti-IL-5). However, blood eosinophil counts vary greatly during the day with exercise and due to circadian steroid rhythms.

The eosinophil is regarded as an important target for patients with asthma, since it is a pro-inflammatory cell that migrates from the bloodstream into inflamed respiratory and gut sites (1, 2). Historically, the humble blood eosinophil count has been extensively used in the management of asthma (3-5). Recently, there has been renewed interest in using blood eosinophil counts to select asthmatic patients for monoclonal antibody therapy (6-10). A mathematical algorithm has been used to predict elevated sputum eosinophils: the eosinophil/lymphocyte and eosinophil/neutrophil index (ELEN) index (9). Moreover, the blood eosinophil count is favoured by recent American Thoracic Society/European Respiratory Society international guidelines on severe asthma, that suggest that the utility of other biomarkers in identifying asthma phenotypes needs further validation (11). However, blood eosinophil counts are notoriously variable, with levels increasing during the day (12) and exercise having the capacity to increase the eosinophil count (13). A recent study of 24-hour blood eosinophil counts noted increased variability in the blood eosinophil count of patients with moderate asthma (14).

Breath NO: levels of exhaled nitric oxide (NO, or FENO) are a crude measure of airway inflammation in asthma. However, levels are variable and very non-specific and can be changed by therapy, dietary factors, and the menstrual cycle in women. They do not provide a specific marker for asthma, where we need to study a range of protein, lipid and prostanoid mediators.

Exhaled breath condensate (EBC) analysis is confounded by the influence of condensed water vapour and the oropharynx; A major problem with current non-invasive sampling methods from the respiratory tract, including breath and sputum analysis, is contamination from the mouth (or oropharynx). Exhaled breath has been extensively studied as a non-invasive means to assess airway inflammation, including by measurement of mediators in exhaled breath condensate (EBC) (15). Richard Effros and colleagues have elegantly highlighted the issues of salivary contamination and dilution in condensed water vapour that occurs during collection of EBC (16-18); and this is likely to be a serious obstacle to measuring EBC pH (19) (20) and levels of inflammatory mediators that are in breath droplets.

Breath volatile organic compound (VOC) analysis and metabolomics looks to be more promising (21-24). However, VOCs do not include proteins such as cytokines, chemokines and antibodies.

Sputum contains dead and dying cells and mediator levels are influenced by bacteria, saliva, proteases, and sticky mucus proteins. Sputum was used to measure eosinophilia by the late Morrow Brown in his original studies from the 1950s showing the efficacy of oral prednisolone in asthma (25), although sputum has been of interest to clinicians since before the time of Hippocrates (26). The clinical application of quantitation of levels of eosinophils in induced sputum was pioneered by the late Freddy Hargreave (27). As an extension of this work, normalisation of sputum eosinophil counts has been shown by Ian Pavord and colleagues (Leicester and Oxford) to be effective in the reduction of asthma exacerbations (28). In addition, adult asthma phenotypes have been defined by sputum eosinophil and neutrophil percentages (29) (30). There are reports that blood eosinophil counts are a poor surrogate for sputum eosinophil counts (31, 32), while another group found that blood eosinophil counts can be used to predict sputum eosinophil counts (33, 34). The analysis of fluid-phase mediators derived from sputum samples has a large number of technical problems (35): these range from degradation by proteases and bacteria, loss of protein secondary structure due to reduction by dithiothreitol (DTT), binding to mucus, contamination with saliva and oropharyngeal contents, and variable leakage of mediators from dead and dying cells. Elegant attempts have been made to validate measurement of fluid phase levels of IL-5 in sputum (36), and this has highlighted the effects of proteases (37).

Nasal sampling is from the airways or respiratory tract, but the mucociliary escalator (MCE) takes nasal molecules from the anterior to posterior, from the nares to the pharynx. Hence the nasal MCE is non-continuous with the MCE up from the lower airways through bronchi and trachea. However, nasosorption is looking preferable to nasal lavage to measure inflammatory mediators, and does inform about airway inflammation from the upper respiratory tract.

Bronchoscopy sampling includes bronchial biopsy, bronchoalveolar lavage (BAL), bronchial brushes, and bronchosorption. Carrying out bronchoscopy to obtain bronchial mucosal biopsies and bronchial brush samples requires a team of specialist staff in an endoscopy suite, and the patient requires sedation and local anaesthesia. Biopsies, BAL, bronchial brushing samples and bronchosorption from the airways are useful samples for analysis: but the procedure is too erroneous for most asthmatics. Bronchoscopy is generally performed in selected patients with lung cancer, tuberculosis (TB) and interstitial lung diseases at specialised centres.

REFERENCE LIST

1. Hogan S P, Rosenberg H F, Moqbel R, Phipps S, Foster P S, Lacy P, Kay A B, Rothenberg M E. *Eosinophils: biological properties and role in health and disease.* Clin Exp Allergy 2008; 38: 709-750.
2. Rosenberg H F, Dyer K D, Foster P S. *Eosinophils: changing perspectives in health and disease.* Nat Rev Immunol 2013; 13: 9-22.
3. Horn B R, Robin E D, Theodore J, Van K A. *Total eosinophil counts in the management of bronchial asthma.* N Engl J Med 1975; 292: 1152-1155.
4. Bousquet J, Chanez P, Lacoste J Y, Barneon G, Ghavanian N, Enander I, Venge P, Ahlstedt 5, Simony-Lafontaine J, Godard P, *Eosinophilic inflammation in asthma.* N Engl J Med 1990; 323: 1033-1039.
5. Tefferi A. *Blood eosinophilia: a new paradigm in disease classification, diagnosis, and treatment.* Mayo Clin Proc 2005; 80: 75-83.
6. Pavord I D, Korn 5, Howarth P, Bleecker E R, Buhl R, Keene O N, Ortega H, Chanez P. *Mepolizumab for severe eosinophilic asthma (DREAM): a multicentre, double-blind, placebo-controlled trial.* Lancet 2012; 380: 651-659.
7. Ortega H G, Liu M C, Pavord I D, Brusselle G G, Fitzgerald I M, Chetta A, Humbert M, Katz L E, Keene O N, Yancey S W, Chanez P. *Mepolizumab treatment in patients with severe eosinophilic asthma.* N Engl J Med 2014; 371: 1198-1207.
8. Bel E H, Wenzel S E, Thompson P1, Prazma C M, Keene O N, Yancey S W, Ortega H G, Pavord I D. *Oral glucocorticoid-sparing effect of mepolizumab in eosinophilic asthma.* N Engl J Med 2014; 371: 1189-1197.
9. Castro M, Wenzel S E, Bleecker E R, Pizzichini E, Kuna P, Busse W W, Gossage D L, Ward C K, Wu Y, Wang B, Khatry D B, van der Merwe R, Kolbeck R, Molfino N A, Raible D G. *Benralizumab, an anti-interleukin 5 receptor alpha monoclonal antibody, versus placebo for uncontrolled eosinophilic asthma: a phase 2b randomised dose-ranging study.* Lancet Respir Med 2014; 2: 879-890.
10. Busse W, Spector 5, Rosen K, Wang Y, Alpan O. *High eosinophil count: a potential biomarker for assessing successful omalizumab treatment effects.* J Allergy Clin Immunol 2013; 132: 485-486.
11. Chung K F, Wenzel S E, Brozek J L, Bush A, Castro M, Sterk P1, Adcock I M, Bateman E D, Bel E H, Bleecker E R, Boulet L P, Brightling C, Chanez P, Dahlen S E, Djukanovic R, Frey U, Gaga M, Gibson P, Hamid Q, Jajour N N, Mauad T, Sorkness R L, Teague W G. *International ERS/ATS guidelines on definition, evaluation and treatment of severe asthma.* Eur Respir J 2014; 43: 343-373.
12. Wempe I B, Tammeling E P, Koeter G H, Hakansson L, Venge P, Postma D S. *Blood eosinophil numbers and activity during 24 hours: effects of treatment with budesonide and bambuterol.* J Allergy Clin Immunol 1992; 90: 757-765.
13. Sand K L, Flatebo T, Andersen M B, Maghazachi A A. *Effects of exercise on leukocytosis and blood hemostasis in 800 healthy young females and males.* World J Exp Med 2013; 3: 11-20.
14. Spector S L, Tan R A. *Is a single blood eosinophil count a reliable marker for "eosinophilic asthma?".* J Asthma 2012; 49: 807-810.
15. Horvath I, Hunt J, Barnes P J. *Exhaled breath condensate: methodological recommendations and unresolved questions.* Eur Respir12005; 26: 523-548.
16. Effros R M, Hoagland K W, Bosbous M, Castillo D, Foss B, Dunning M, Gare M, Lin W, Sun F. *Dilution of respiratory solutes in exhaled condensates.* Am J Respir Crit Care Med 2002; 165: 663-669.
17. Effros R M, Casaburi R, Su J, Dunning M, Torday J, Biller J, Shaker R. *The effects of volatile salivary acids and bases on exhaled breath condensate pH.* Am J Respir Crit Care Med 2006; 173: 386-392.
18. Effros R M, Casaburi R, Porszasz J, Morales E M, Rehan V. *Exhaled breath condensates: analyzing the expiratory plume.* Am J Respir Crit Care Med 2012; 185: 803-804.
19. Nicolaou N C, Lowe L A, Murray C S, Woodcock A, Simpson A, Custovic A. *Exhaled breath condensate pH and childhood asthma: unselected birth cohort study.* Am J Respir Crit Care Med 2006; 174: 254-259.
20. Liu L, Teague W G, Erzurum 5, Fitzpatrick A, Mantri 5, Dweik R A, Bleecker E R, Meyers D, Busse W W, Calhoun W I, Castro M, Chung K F, Curran-Everett D, Israel E, Jarjour W N, Moore W, Peters S P, Wenzel 5, Hunt I F, Gaston B. *Determinants of exhaled breath condensate pH in a large population with asthma.* Chest 2011; 139: 328-336.
21. Wagener A H, Yick C Y, Brinkman P, van der Schee M P, Fens N, Sterk P J. *Toward composite molecular signatures in the phenotyping of asthma.* Ann Am Thorac Soc 2013; 10 Suppl: S197-5205.
22. Bikov A, Paschalaki K, Logan-Sinclair R, Horvath I, Kharitonov S A, Barnes P1, Usmani O S, Paredi P. *Standardised exhaled breath collection for the measurement of exhaled volatile organic compounds by proton transfer reaction mass spectrometry.* BMC Pulm Med 2013; 13: 43.
23. van der Schee M P, Hashimoto 5, Schuurman A C, Repelaer van Driel I S, Adriaens N, van Amelsfoort R M, Snoeren T, Regenboog M, Sprikkelman A B, Haarman E G, van Aalderen W M, Sterk P J. *Altered exhaled biomarker profiles in children during and after rhinovirus-induced wheeze.* Eur Respir J 2015; 45: 440-448.
24. van der Schee M P, Paff T, Brinkman P, van Aalderen W M, Haarman E G, Sterk P J. *Breathomics in lung disease.* Chest 2015; 147: 224-231.
25. Brown H M. *Treatment of chronic asthma with prednisolone; significance of eosinophils in the sputum.* Lancet 1958; 2: 1245-1247.
26. FINLAYSON R. *The vicissitudes of sputum cytology.* Med Hist 1958; 2: 24-35.
27. Djukanovic R, Sterk P1, Fahy I V, Hargreave F E. *Standardised methodology of sputum induction and processing.* Eur Respir J Suppl 2002; 37: 1s-2s.
28. Green R H, Brightling C E, McKenna 5, Hargadon B, Parker D, Bradding P, Wardlaw A J, Pavord I D. *Asthma exacerbations and sputum eosinophil counts: a randomised controlled trial.* Lancet 2002; 360: 1715-1721.
29. Moore W C, Hastie A T, Li X, Li H, Busse W W, larjour NN, Wenzel S E, Peters S P, Meyers D A, Bleecker E R. *Sputum neutrophil counts are associated with more severe asthma phenotypes using cluster analysis.* J Allergy Clin Immunol 2014; 133: 1557-1563.
30. Hastie A T, Moore W C, Meyers D A, Vestal P L, Li H, Peters S P, Bleecker E R. *Analyses of asthma severity phenotypes and inflammatory proteins in sub-* jects stratified by sputum granulocytes. *J Allergy Clin Immunol* 2010; 125: 1028-1036.
31. Hastie A T, Moore W C, Li H, Rector B M, Ortega V E, Pascual R M, Peters S P, Meyers D A, Bleecker E R. *Biomarker surrogates do not accurately predict sputum eosinophil and neutrophil percentages in asthmatic subjects. J Allergy Clin Immunol* 2013; 132: 72-80.
32. Schleich F N, Louis R. *Importance of concomitant local and systemic eosinophilia in uncontrolled asthma. Eur Respirl* 2014; 44: 1098-1099.
33. Schleich F N, Manise M, Sele J, Henket M, Seidel L, Louis R. *Distribution of sputum cellular phenotype in a large asthma cohort: predicting factors for eosinophilic vs neutrophilic inflammation. BMC Pulm Med* 2013; 13: 11.
34. Wagener A H, de Nijs S B, Lutter R, Sousa A R, Weersink E J, Bel E H, Sterk P J. *External validation of blood eosinophils, FE(NO) and serum periostin as surrogates for sputum eosinophils in asthma. Thorax* 2015; 70: 115-120.
35. Kelly M M, Keatings V, Leigh R, Peterson C, Shute 1, Venge P, Djukanovic R. *Standardsed methodology of sputum induction and processing (ERS Task Force): analysis of fluid-phase mediators. Eur Respirl* 2002; 20: 24s-39s.
36. Kelly M M, Leigh R, Horsewood P, Gleich G I, Cox G, Hargreave F E. *Induced sputum: validity of fluid-phase IL-5 measurement. J Allergy Clin Immunol* 2000; 105: 1162-1168.
37. Kelly M M, Leigh R, Carruthers 5, Horsewood P, Gleich G I, Hargreave F E, Cox G. *Increased detection of interleukin-5 in sputum by addition of protease inhibitors. Eur Respirl* 2001; 18: 685-691.
38. Lu F X, Esch R E. *Novel nasal secretion collection method for the analysis of allergen specific antibodies and inflammatory biomarkers. J Immunol Methods* 2010; 356: 6-17.
39. BLK C, MI E, B S, C W, GC N, AJ T, NV F, K B, H B, TT H. *A letter to the editor: A novel method for assessing unchallenged levels of mediators in nasal epithelial lining fluid. J Allergy Clin Immunol* 2010; 125: 1387-1389.
40. NV F, BL C, MA R, AL B, CG C, J S, L P, TT H, K B, S B, H B. *Maternal atopic skewing of the neonatal nasal cytokine signature. Am J Resp Crit Care Med* 2011.
41. Nicholson G C, Kariyawasam H H, Tan A J, Hohlfeld J M, Quinn D, Walker C, Rodman D, Westwick J, Jurcevic 5, Kon O M, Barnes P J, Krug N, Hansel T T. *The effects of an anti-IL-13 mAb on cytokine levels and nasal symptoms following nasal allergen challenge. J Allergy Clin Immunol* 2011; 128: 800-807.
42. Scadding G W, Calderon M A, Bellido V, Koed G K, Nielsen N C, Lund K, Togias A, Phippard D, Turka L A, Hansel T T, Durham S R, Wurtzen P A. *Optimisation of grass pollen nasal allergen challenge for assessment of clinical and immunological outcomes. J Immunol Methods* 2012; 384: 25-32.
43. Dhariwal J, Kitson J, Jones R E, Nicholson G, Tunstall T, Walton R P, Francombe G, Gilbert J, Tan A J, Murdoch R, Kon O M, Openshaw P J, Hansel T T. *Nasal Lipopolysaccharide Challenge and Cytokine Measurement Reflects Innate Mucosal Immune Responsiveness. PLoS ONE* 2015; 10: e0135363.
44. Jayaraman A, Jackson D J, Message S D, Pearson R M, Aniscenko J, Caramori G, Mallia P, Papi A, Shamji B, Edwards M, Westwick J, Hansel T, Stanciu L A, Johnston S L, Bartlett N W. *IL-15 complexes induce NK-and T-cell responses independent of type I IFN signaling during rhinovirus infection. Mucosal Immunol* 2014; 7: 1151-1164.
45. Beale J, Jayaraman A, Jackson D J, Macintyre J D, Edwards M R, Walton R P, Zhu J, Ching Y M, Shamji B, Edwards M, Westwick J, Cousins D J, Hwang Y Y, McKenzie A, Johnston S L, Bartlett N W. *Rhinovirus-induced IL-25 in asthma exacerbation drives type 2 immunity and allergic pulmonary inflammation. Sci Trans' Med* 2014; 6: 256ra134.
46. Jackson D J, Makrinioti H, Rana B M, Shamji B W, Trujillo-Torralbo M B, Footitt J, Jerico D, Telcian A G, Nikonova A, Zhu J, Aniscenko J, Gogsadze L, Bakhsoliani E, Traub S, Dhariwal J, Porter J, Hunt D, Hunt T, Hunt T, Stanciu L A, Khaitov M, Bartlett N W, Edwards M R, Kon O M, Mallia P, Papadopoulos N G, Akdis C A, Westwick J, Edwards M J, Cousins D J, Walton R P, Johnston S L. *IL-33-Dependent Type 2 Inflammation during Rhinovirus-induced Asthma Exacerbations In Vivo. Am J Respir Crit Care Med* 2014; 190: 1373-1382.
47. Jackson D J, Glanville N, Trujillo-Torralbo M B, Shamji B W, Del-Rosario J, Mallia P, Edwards M J, Walton R P, Edwards M R, Johnston S L. *Interleukin-18 is associated with protection against rhinovirus-induced colds and asthma exacerbations. Clin Infect Dis* 2015; 60: 1528-1531.

STATEMENTS OF INVENTION

Aspects of the present invention seek to provide improved airway sampling devices and methods which seek to overcome or ameliorate one or more of the problems associated with the prior art. In particular, embodiments of the present invention aim to provide a non-invasive airway sampling device and sampling method for sampling airway mucosal lining fluid (MLF), and especially to obtain lower respiratory tract samples (originating from beyond the vocal cords) free from (or with only minimal) salivary and oropharyngeal contamination.

An aspect of the current invention is based on sampling droplets from the vocal cords and lower respiratory tract (the peripheral airways beyond the vocal cords). The aspect samples mucosal lining fluid (MLF) that is expelled from the lower respiratory tract by forced expiration or coughing. A key feature of an aspect of the invention is to minimise salivary contamination of the obtained sample. A further aspect of the invention is to non-invasively obtain a lower respiratory tract specimen without employing bronchoscopy. An important feature of lower airway MLF is that it passes continuously up the respiratory tract through the mucociliary escalator (MCE), and then passages through the vocal cords before being swallowed. Hence MLF from the vocal cords reflect airway events in the peripheral lower respiratory tract. The MLF in the small airways contains molecules and biomarkers that reflect disease in the underlying tissue. The small airway MLF is transmitted by the MCE to larger airways and up to the vocal cords. The inventors of the present invention have appreciated that it is of great benefit to assess respiratory diseases to capture the fluids from the vocal cords and lower airways in a non-invasive and precise manner, obtaining a sample from the lower respiratory tract (the trachea, bronchi and bronchioles) that is free from (or with only minimal) saliva and oropharyngeal contamination.

According to a first aspect of the present invention, there is provided an airway sampling device for taking a sample from a subject's airway, the device comprising a handle to be gripped by a user when taking the sample and a sampling head carried by the handle, the sampling head comprising a cavity with an opening for entry by the sample and a sample collection membrane located within the cavity for receiving the sample.

Preferably, the sample collection membrane comprises absorbent and/or adsorbent material.

Preferably, the sample collection membrane is detachable from the sampling head.

Preferably, the sample collection membrane comprises a perforation to facilitate its removal from the sampling head.

Preferably, the sample collection membrane comprises a notch to facilitate grasping of the sample collection membrane when detaching the sample collection membrane from the sampling head.

Preferably, the cavity has a gutter provided at least partly around its opening.

Preferably, the cavity is defined within a peripheral wall provided at least partly around the sampling head, and wherein outer surfaces of the peripheral wall are configured to be perpendicular to the tonsils of the subject when the sampling head is inserted into and/or removed from the subject's pharynx.

Preferably, the cavity is defined within a peripheral wall provided at least partly around the sampling head, and wherein an outer surface of the peripheral wall is configured to be perpendicular to the uvula and/or posterior wall of the oropharynx of the subject during capture of the sample.

Preferably, an outer surface of the peripheral wall is configured to deflect the uvula of the subject, allowing the sampling head to enter the pharynx from the oral cavity.

Preferably, the sampling head is connected to the handle via a stem.

Preferably, the sampling head, stem and handle are integrally formed.

Preferably, the handle is provided with a protrusion for engagement by a finger of the user, to facilitate grip of the handle.

Preferably, the handle is provided with a chamber, and the sampling head is movable relative to the handle between a first condition in which the sampling head is distal from the handle and a second condition in which the cavity is located over the chamber to define an enclosure which encloses the sample collection membrane between the interior of the cavity and the interior of the chamber.

Preferably, the enclosure is fluid-tight.

Preferably, a weakened area is provided in one of the chamber or the cavity.

Preferably, the weakened area is configured to rupture when pressure is applied to the enclosure.

Preferably, the weakened area is provided in the chamber, and the chamber is formed from a deformable material to allow a user to apply pressure to the enclosure.

Preferably, the weakened area is configured to permit a syringe needle to be inserted into the enclosure.

Preferably, the weakened area is configured to rupture when the sampling device is spun by a centrifuge.

Preferably, the interior of the cavity is provided with one or more protrusions on which the sample collection membrane is located.

Preferably, the interior of the cavity is provided with a plurality of protrusions in a chevron pattern on which the sample collection membrane is located.

Preferably, the interior of the chamber is provided with one or more protrusions which contact the sample collection membrane when the sampling device is placed into its second condition.

Preferably, the one or more protrusions are configured to push against the sample collection membrane when the user applies pressure to the enclosure.

Preferably, the sampling device comprises retaining means to retain the sampling device in its first condition and in its second condition.

Preferably, an edge of the handle comprises a scalloped area to facilitate movement of the sampling device into the first condition from the second condition.

Preferably, the sampling device further comprises an illumination module, and the sampling head is configured as a light guide to guide and emit light emitted from the illumination module.

Preferably, the illumination module is removably mounted on the sampling device.

Preferably the illumination module comprises a switch and the handle comprises a projection for actuating the switch to an on position when the sampling device is mounted to the sampling device.

Preferably the illumination module comprises a switch and the handle comprises a projection for actuating the switch to an on position when the sampling device is placed into its first condition.

Preferably the illumination module comprises an LED light source or a laser light source.

Preferably, the sampling head is provided at a first end of the sampling device distal from a second end of the sampling device at which the handle is provided, and the sampling device further comprises a shield mounted between the first and second ends of the sampling device, for shielding the user from sample from the subject.

Preferably, the airway sampling device is shaped and dimensioned so as to locate the opening of the cavity over the vocal cords and within the oropharynx posterior to the uvula of a subject when the sampling head is located at a sampling position in the patient's airway for taking the sample.

Preferably, the sampling head is angled relative to the handle, so as to present the plane of the opening of the cavity at an angle of between 25° to 45° downwardly from horizontal when the sampling head is located at the sampling position in the patient's airway.

Most preferably, the sampling head is angled relative to the handle, so as to present the plane of the opening of the cavity at an angle of 39° downwardly from horizontal when the sampling head is located at the sampling position in the patient's airway.

Preferably, the depth of the sampling device, from an uppermost surface of the handle to a lowermost tip of the sampling head is from 17 mm to 23 mm.

Preferably, the length of the opening is between 15 mm to 30 mm.

Most preferably, the length of the opening is 26 mm.

Preferably, the maximum width of the sampling head is between 10 mm to 16 mm.

Most preferably, the maximum width of the sampling head is 16 mm.

Preferably, an outer surface of the sampling head is designed so as to be perpendicular to at least one of the tonsils, uvula, and back of a subject's throat during placement, sample capture, and removal of the sampling device from the subject's airway.

According to a second aspect of the present invention, there is provided an airway sampling device for taking a sample from a sampling position within a subject's airway, the device comprising a handle to be gripped by a user when taking the sample and a sampling head for insertion into the subject's airway and being carried by the handle, the sampling head comprising a cavity with an opening for entry by the sample, and wherein the airway sampling device is shaped and/or dimensioned so as to locate the opening over the vocal cords and within the oropharynx, posterior to the uvula, of a subject when the sampling head is located at the sampling position in the patient's airway.

Preferably, the sampling head is angled relative to the handle, so as to present the plane of the opening of the cavity at an angle of between 25° to 45° downwardly from horizontal when the sampling head is located at the sampling position in the patient's airway.

Most preferably, the sampling head is angled relative to the handle, so as to present the plane of the opening of the cavity at an angle of 39° downwardly from horizontal when the sampling head is located at the sampling position in the patient's airway.

Preferably, the depth of the sampling device, from an uppermost surface of the handle to a lowermost tip of the sampling head is from 17 mm to 23 mm.

Preferably, the length of the opening is between 15 mm to 30 mm.

Most preferably, the length of the opening is 26 mm.

Preferably, the maximum width of the sampling head is between 10 mm to 16 mm.

Most preferably, the maximum width of the sampling head is 16 mm.

Preferably, an outer surface of the sampling head is designed so as to be perpendicular to the tonsils, uvula, and back of a subject's throat during placement, sample capture, and removal of the sampling device from the subject's airway.

According to a third aspect of the present invention, there is provided an airway sampling device for taking a sample from a subject's airway, the device comprising a handle to be gripped by a user when taking the sample and a sampling head carried by the handle, wherein the handle is provided with a chamber, and the sampling head is movable relative to the handle between a first condition of the sampling device in which the sampling head is distal from the handle and a second condition of the sampling device in which the sampling head is located adjacent the chamber.

Preferably, an enclosure is defined between the sampling head and the chamber when the sampling device is in the second condition.

Preferably, the enclosure is fluid-tight.

Preferably, a weakened area is provided in one of the chamber or the sampling head.

Preferably, the weakened area is configured to rupture when pressure is applied to the enclosure.

Preferably, the weakened area is provided in the chamber, and the chamber is formed from a deformable material to allow a user to apply pressure to the enclosure.

Preferably, the weakened area is configured to permit a syringe needle to be inserted into the enclosure.

Preferably, the weakened area is configured to rupture when the sampling device is spun by a centrifuge.

Preferably, a sample collection membrane is located within the sampling head.

Preferably, the interior of the sampling head is provided with one or more protrusions on which the sample collection membrane is located.

Preferably, the interior of the sampling head is provided with a plurality of protrusions in a chevron pattern on which the sample collection membrane is located.

Preferably, the interior of the chamber is provided with one or more protrusions which contact the sample collection membrane when the sampling device is placed into its second condition.

Preferably, the sampling device comprises retaining means to retain the sampling device in its first condition and in its second condition.

Preferably, an edge of the handle comprises a scalloped area to facilitate movement of the sampling device into the first condition from the second condition.

According to a fourth aspect of the present invention, there is provided a method of taking a sample from a subject's airway, the method comprising collecting a sample from a sampling position located above the vocal cords and within the oropharynx and posterior to the uvula of a subject.

Preferably, the step of collecting the sample comprises:
positioning a sample collector within the subject's airway at the sampling position; and
prompting the subject to cough or give a forced exhalation, so as to produce the sample.

Preferably, the sample comprises mucosal lining fluid projected from the subject's vocal cords by the subject's cough or forced exhalation.

According to a fifth aspect of the present invention, there is provided a method of preparing a sample from a subject taken using the sampling device of the first aspect, the method comprising exposing the sample collection membrane to an elution buffer to elute the sample into the elution buffer.

Preferably, the method comprises removing the sample collection membrane from the cavity and placing it into the elution buffer.

Preferably, the handle of the sampling device is provided with a chamber, and the sampling head is movable relative to the handle between a first condition in which the sampling head is distal from the handle and a second condition in which the cavity is located over the chamber to define an enclosure which encloses the sample collection membrane between the interior of the cavity and the interior of the chamber, and wherein the method comprises introducing the elution buffer into the chamber and placing the sampling device into its second condition, to expose the sample collection membrane to the elution buffer.

Preferably, the method further comprises agitating the sampling device after the sampling device has been placed into its second condition.

Preferably, a weakened area is provided in one of the chamber or the cavity, and the method further comprises applying pressure to the enclosure to rupture the weakened area, to remove the elution buffer, containing the eluted sample, from the enclosure.

Preferably, the method further comprises inserting the needle of a syringe into the enclosure, and extracting the elution buffer, containing the eluted sample, from the enclosure using the syringe.

Preferably, a weakened area is provided in one of the chamber or the cavity, and the method further comprises placing the sampling device, still in its second condition, into a vessel and spinning the vessel using a centrifuge, rupturing the weakened area and introducing the elution buffer, containing the eluted sample, into the vessel.

Preferably, the method further comprises freezing the sampling device, still in its second condition, with the elution buffer, containing the eluted sample, still located within the enclosure.

LIST OF FIGURES

In order that the present invention may be more readily understood, embodiments thereof will now be described, by way of example only, with reference to the accompanying drawings, of which:

FIG. 1 is a schematic view showing a detail of part of the muco-ciliary escalator of a human subject;

FIGS. 2A TO 2E schematically illustrate the cough function of a human subject;

Figures 10, 11:
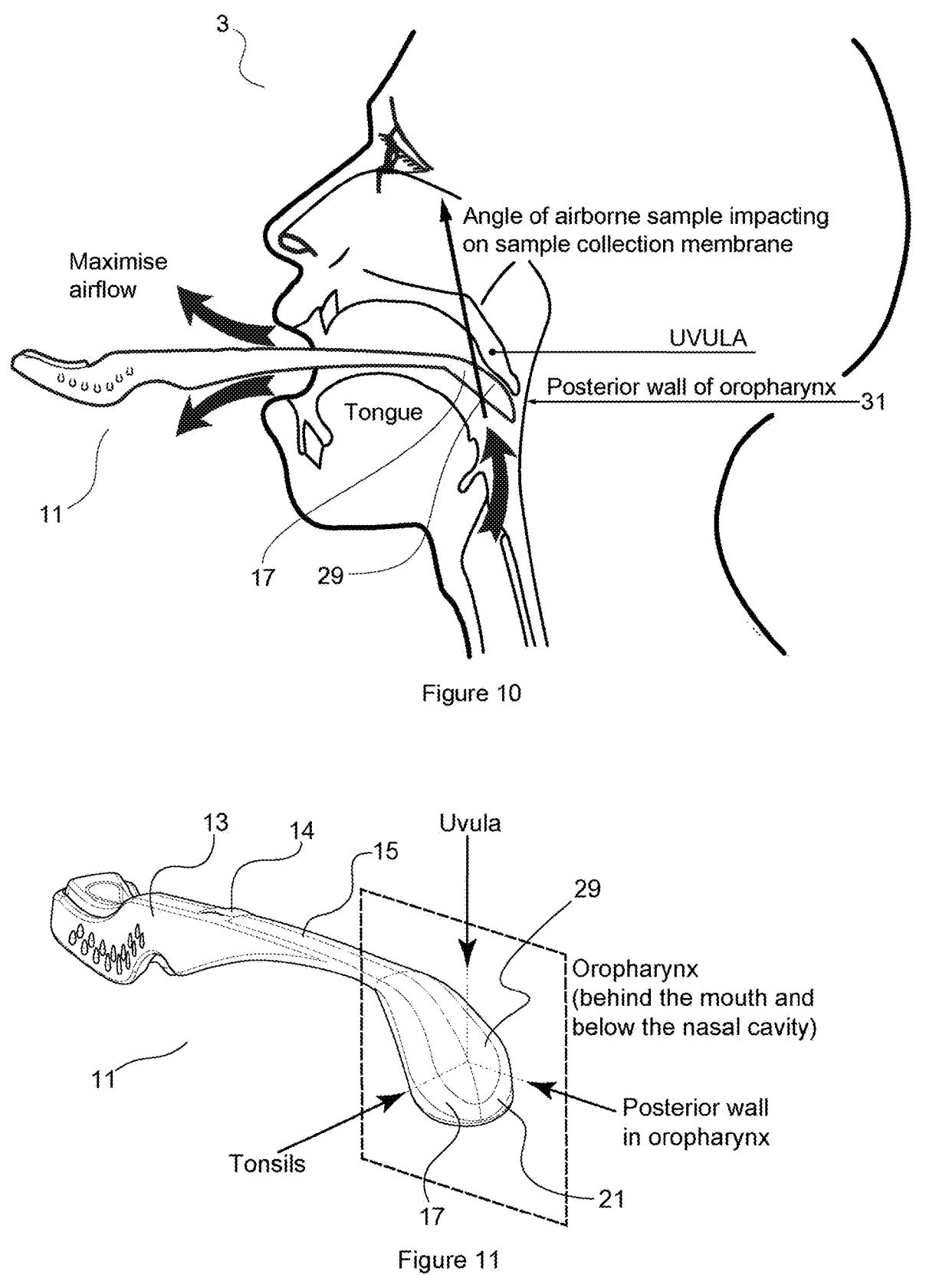
Figure 12:
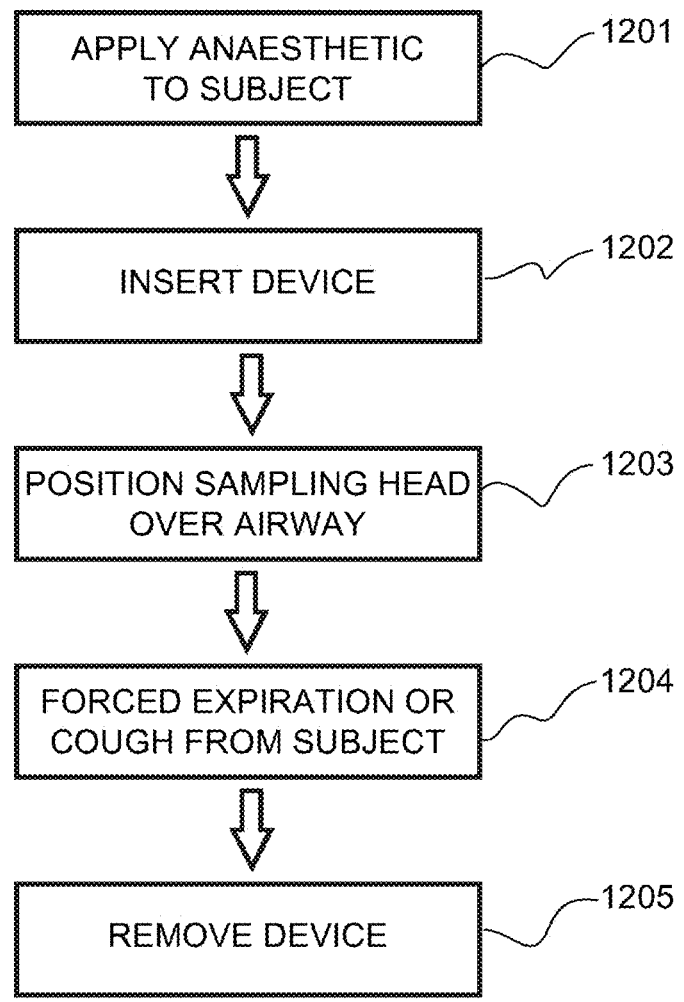
Figure 13:
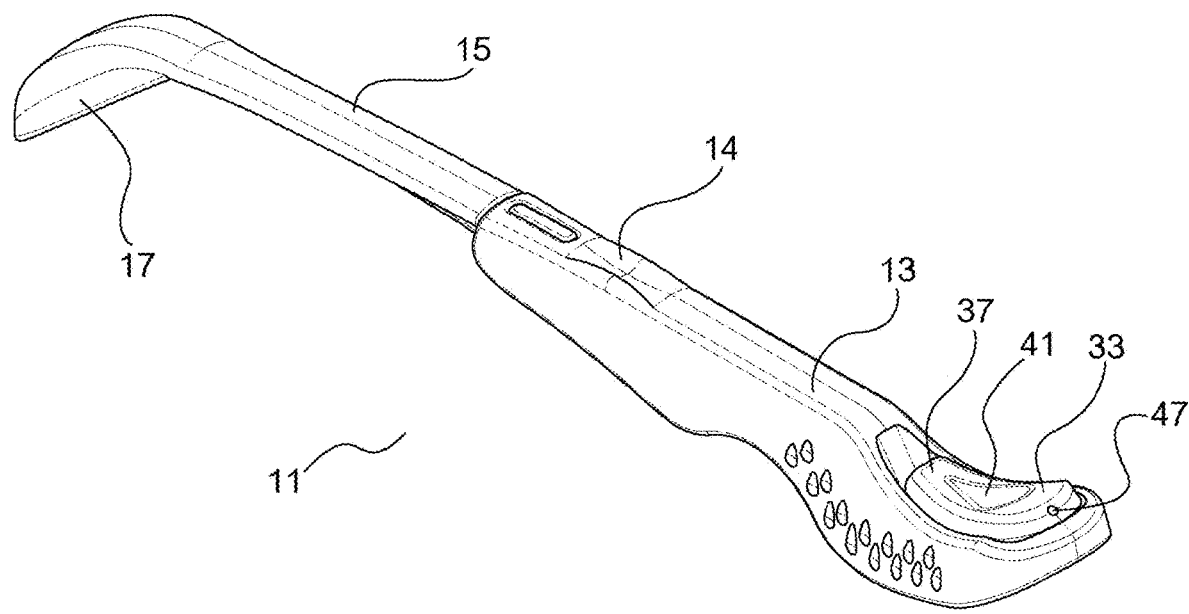
Figure 17A:
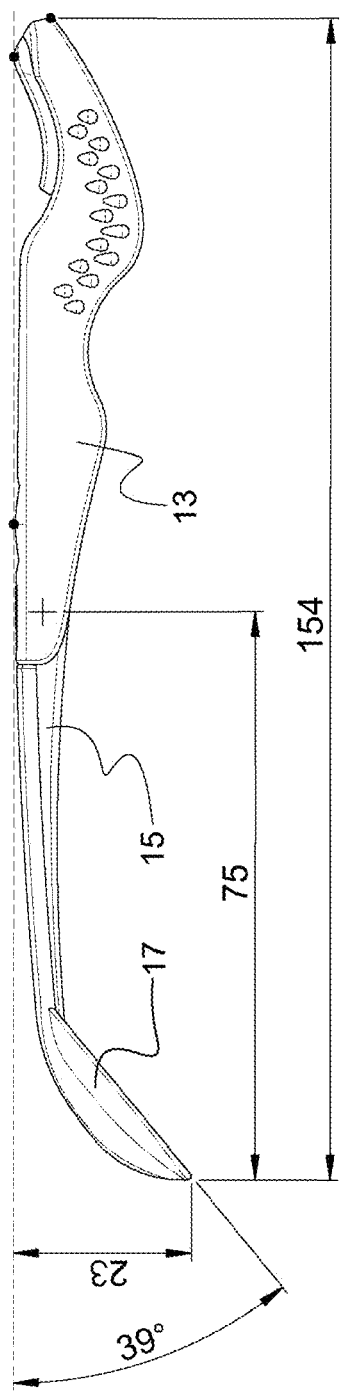
Figure 17B:
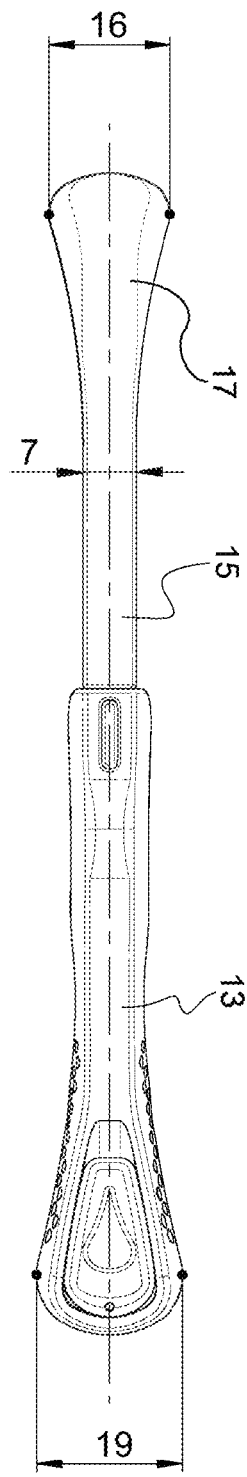
Figure 20:
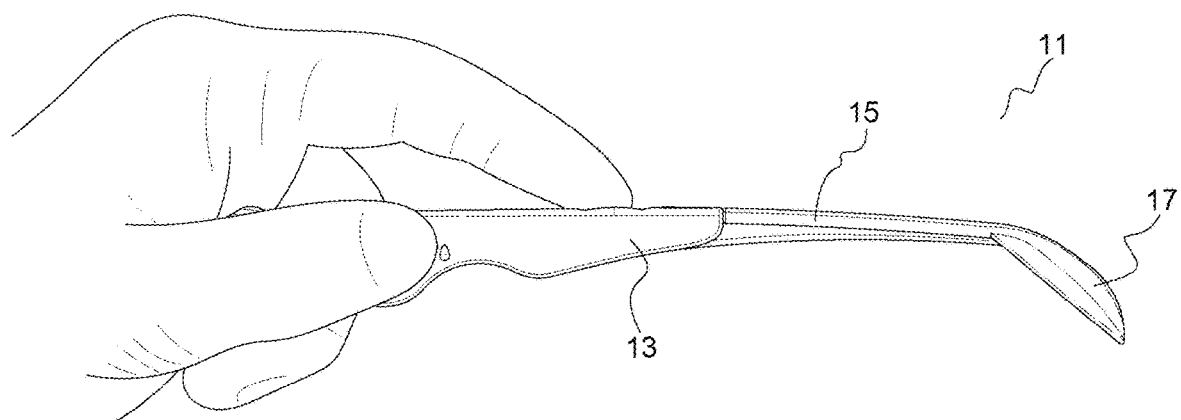
Figure 21:
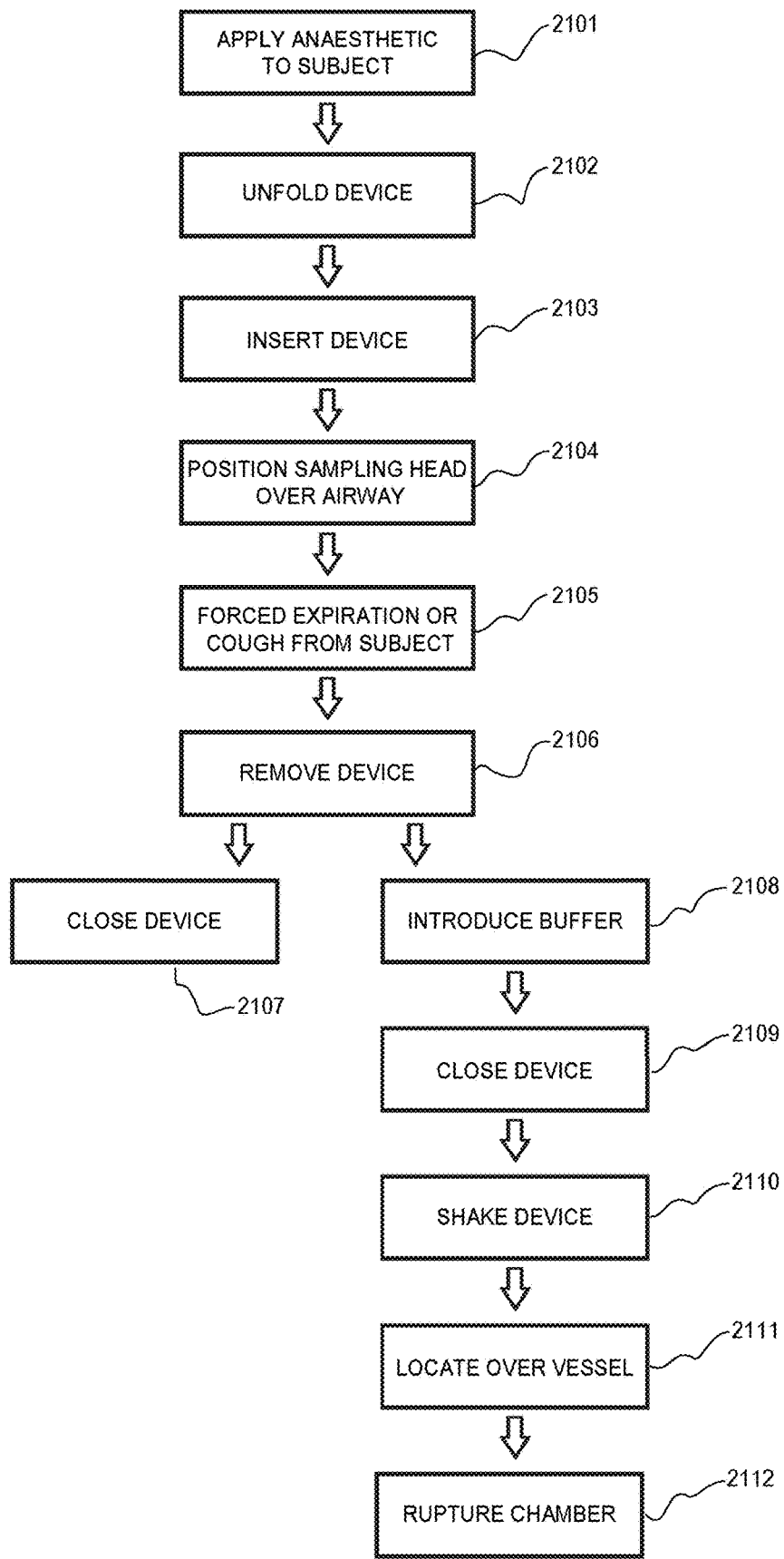
Figure 22:
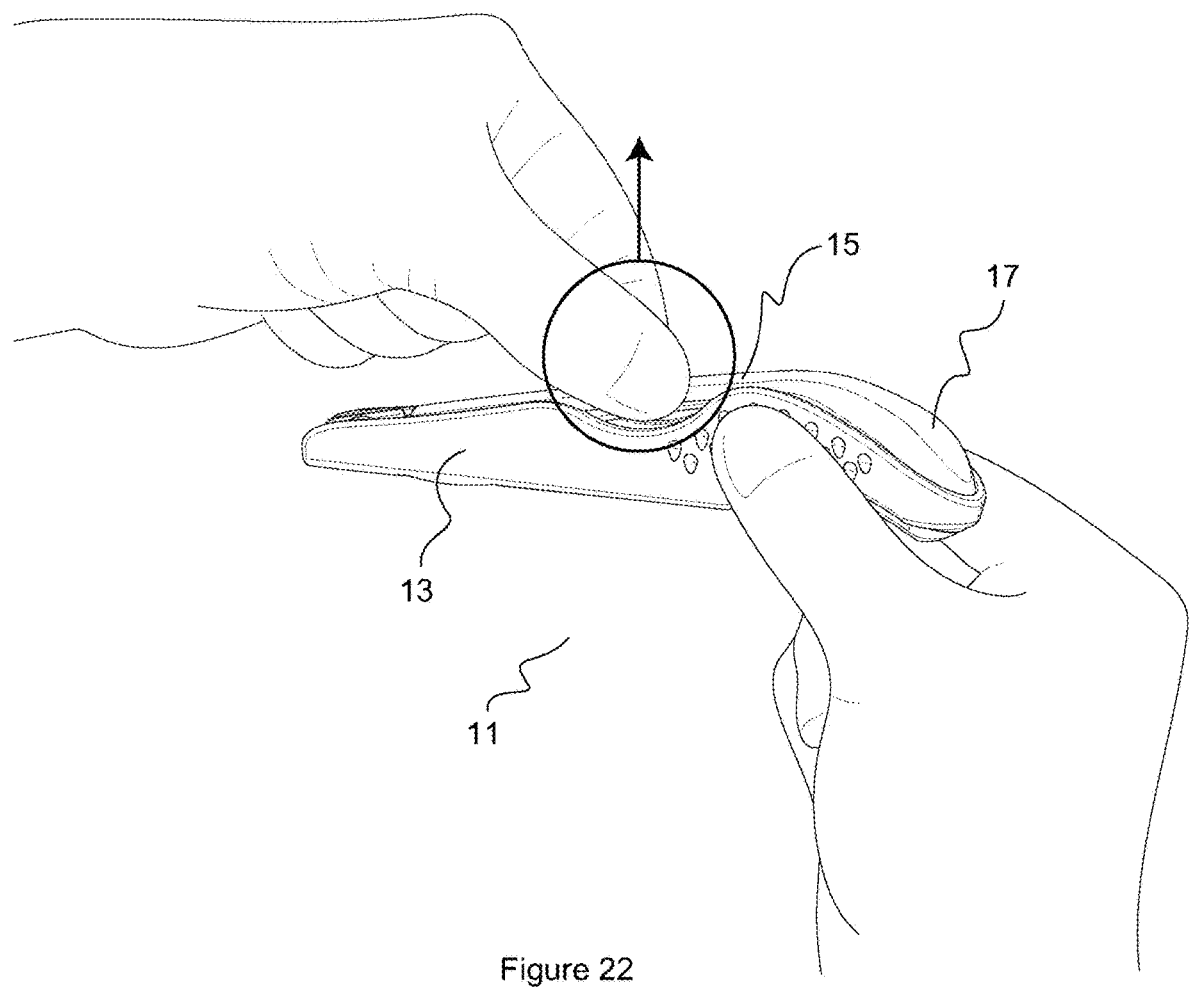
Figure 23:
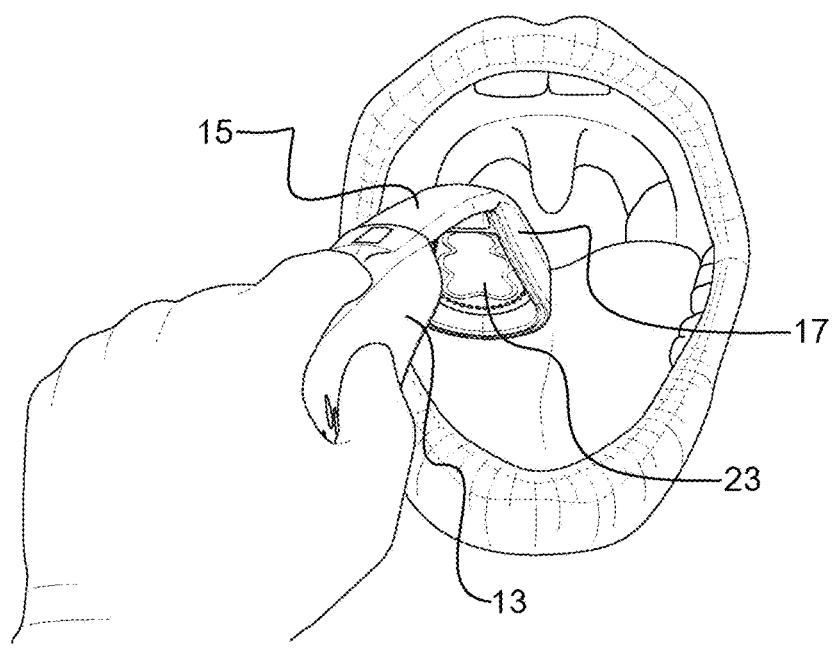
Figure 24:
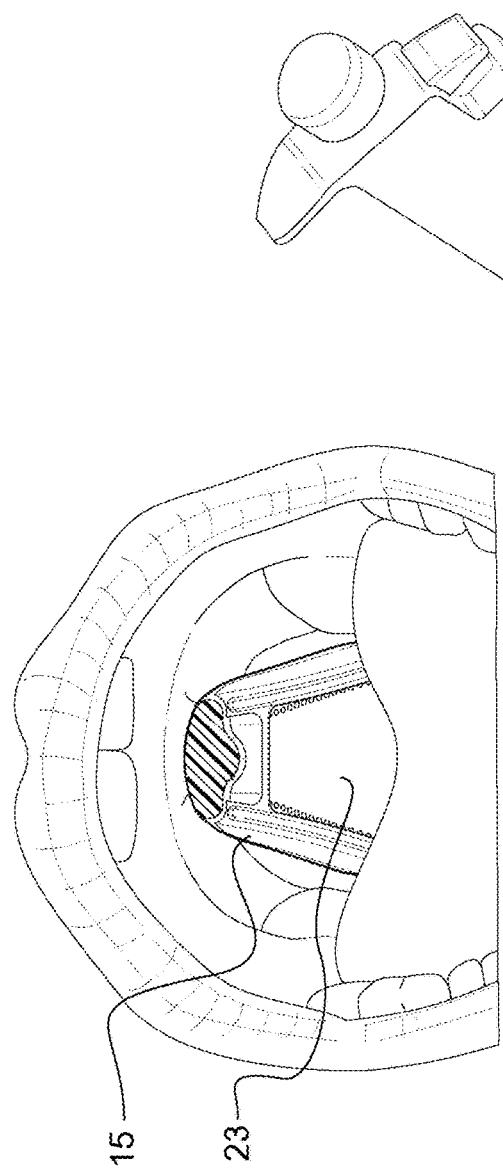
Figure 25A:
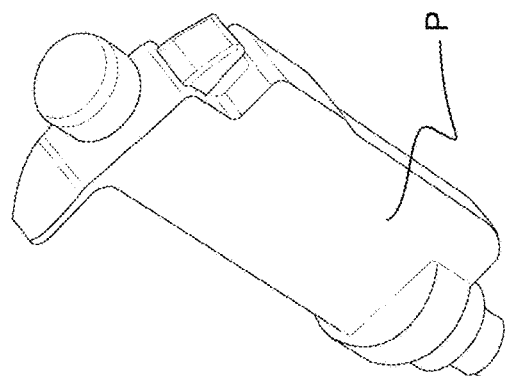
Figure 25A:
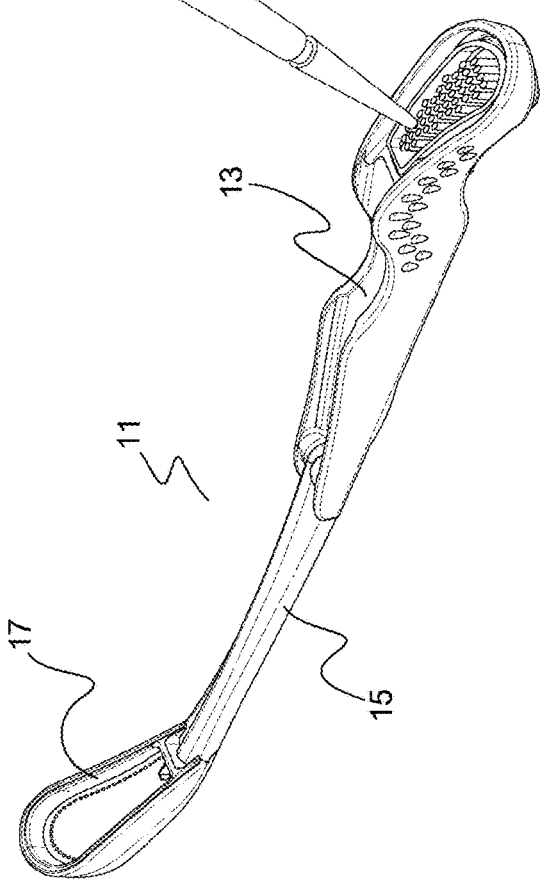
Figure 32:
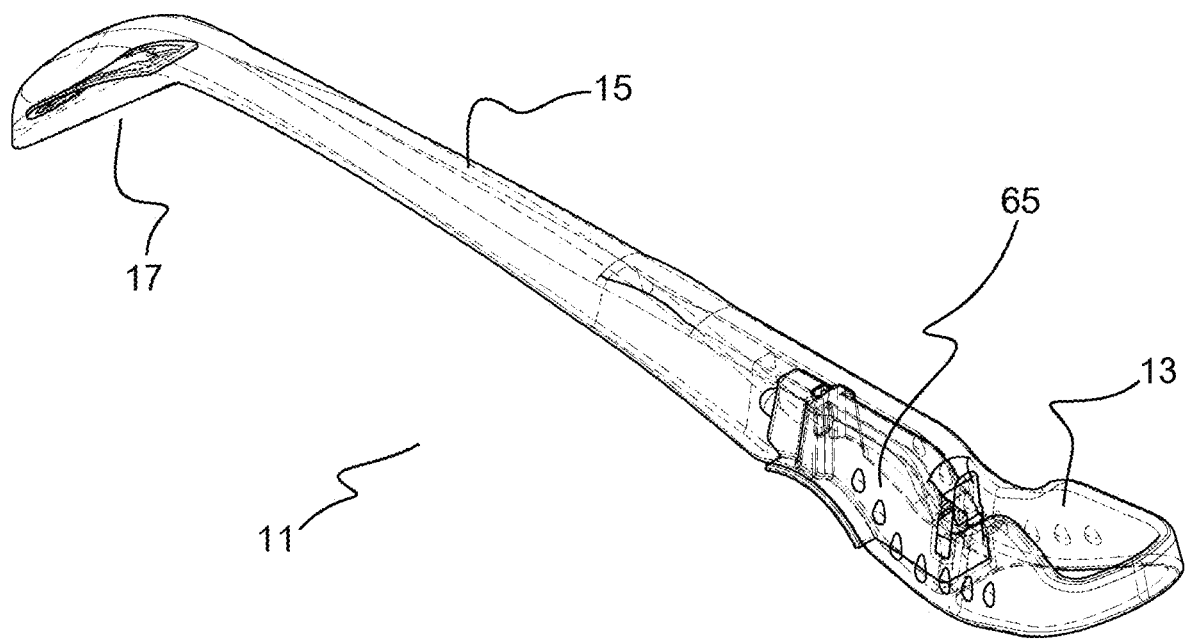
Figure 33:
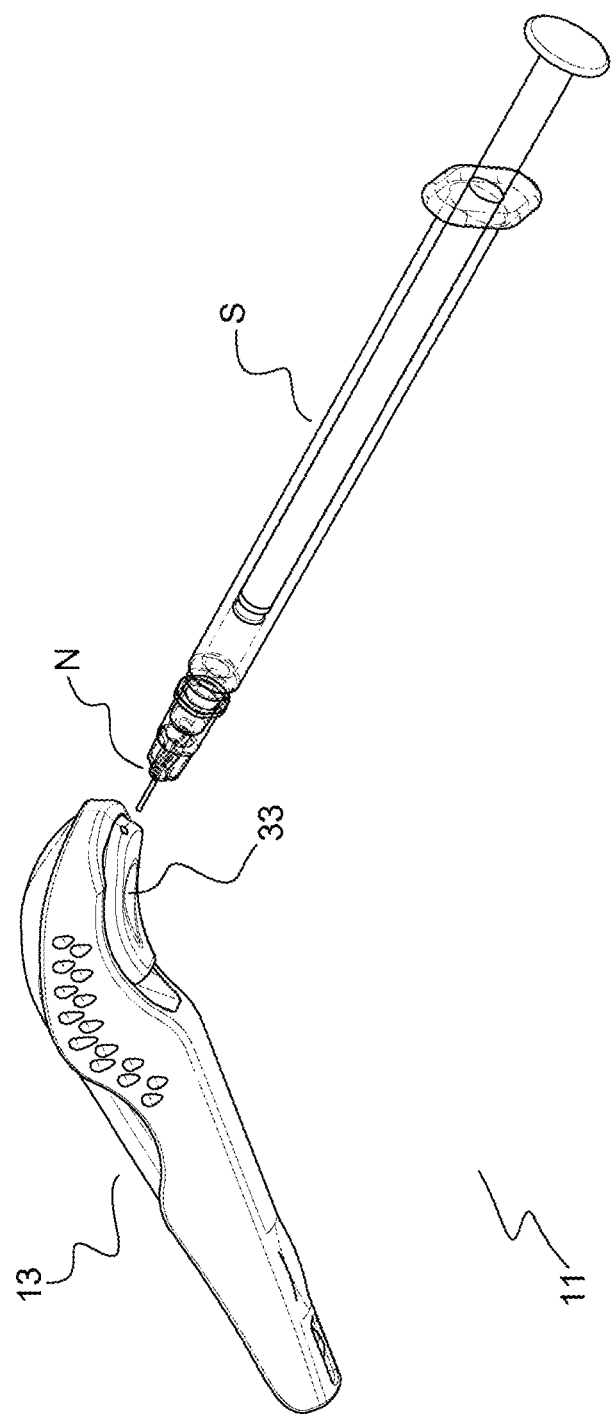
Figure 36:
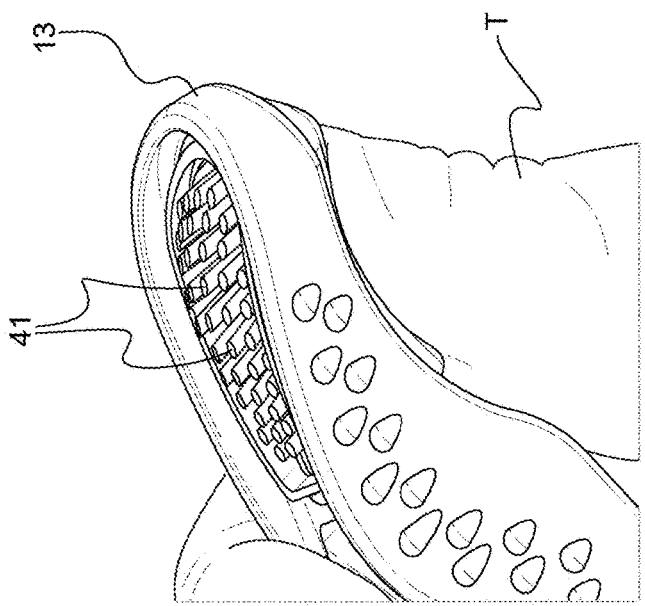
Figure 34:
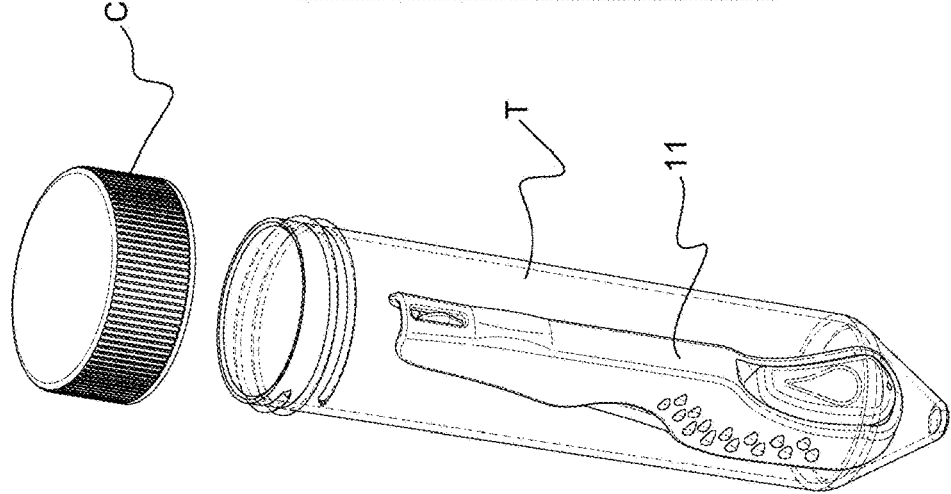

FIGS. 6 to 10 describe various preferable dimension and angling features of the first embodiment;

FIG. 11 shows a protective hood of the sampling device of the first embodiment;

FIG. 12 is a flow chart of a first sampling method according to an embodiment of the present invention;

FIGS. 13 to 15 show a second embodiment of a sampling device according to the present invention and various details thereof;

FIG. 16 shows assembly of the second embodiment;

FIGS. 17 and 18 show various preferable dimension and angling features of the second embodiment;

FIGS. 19A to 19E show the second embodiment in various free standing conditions;

FIG. 20 shows the second embodiment being held by a user;

FIG. 21 is a flow chart illustrating a second embodiment of a sampling method according to the present invention, with FIGS. 22 to 27 illustrating various steps of that method;

FIG. 28 shows a third embodiment of a sampling device according to the present invention;

FIGS. 29 to 31 shows a fourth embodiment of a sampling device according to the present invention;

FIG. 32 shows a fifth embodiment of a sampling device according to the present invention;

FIGS. 33 and 34 illustrate alternative sampling methods according to further embodiments of the present invention; and FIGS. 25 and 36 show details of the second embodiment.

DESCRIPTION OF EXEMPLARY EMBODIMENTS

Figure 1:
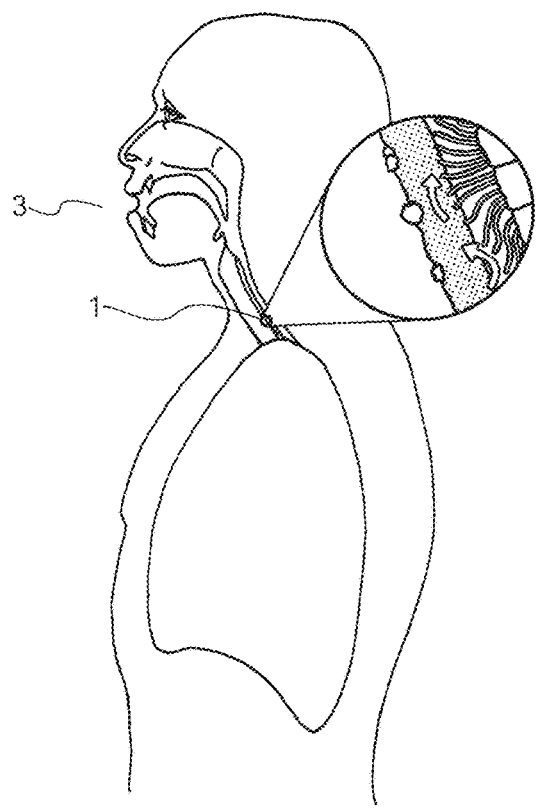

FIG. 1 is a schematic diagram showing a detail of a small section of the Muco-Ciliary Escalator (MCE) (shown generally at 1) in a human subject 3. The MCE 1 transports Mucosal Lining Fluid (MLF) from the small airways up to the larynx and the vocal cords. In particular, ciliary beating carries MLF upwards from small bronchioles to larger bronchi and onwards to the trachea and to the larynx through the vocal cords. The MLF is then normally swallowed (at a rate of approximately 30 ml/day).

The vocal cords (in the larynx) are "the gateway to the lower respiratory tract" and airways. The MLF provides the body with a barrier against infection clearing out the airways carrying with it foreign particles and microorganisms. Due to the MCE, vocal cord MLF (from part of the larynx) reflects large and small airway molecular events. The surface MLF reflects information in the underlying airway wall and peripheral airway. This is relevant to biomarkers for example for vaccination, lung cancer, infection (whether viral, bacterial or fungal), inflammation, asthma/chronic obstructive pulmonary disease (COPD)/lung fibrosis/cystic fibrosis.

Embodiments of the present invention aim to collect pure vocal cord MLF, free (or with only minimal contamination) from saliva. To do so, embodiments of the present invention take advantage of the fact that the cough function of the human body expels MLF from the vocal chords to the oropharynx. By sampling this expelled MLF from a position within the oropharynx, pure vocal cord MLF, uncontaminated (or with only minimal contamination) by saliva, may be obtained, e.g. to allow analysis of biomarkers contained in the MLF.

The cough function is schematically illustrated with reference to FIGS. 2A to 2E. Coughing forces air through the vocal cords at high speed (typically, air is expelled in a cough at velocities ranging from around 75 to 100 miles/hour). Tracheal and vocal cord MLF is expelled from the mouth by coughing, along with saliva from the uvula, tongue and oropharynx.

Figure 2A:
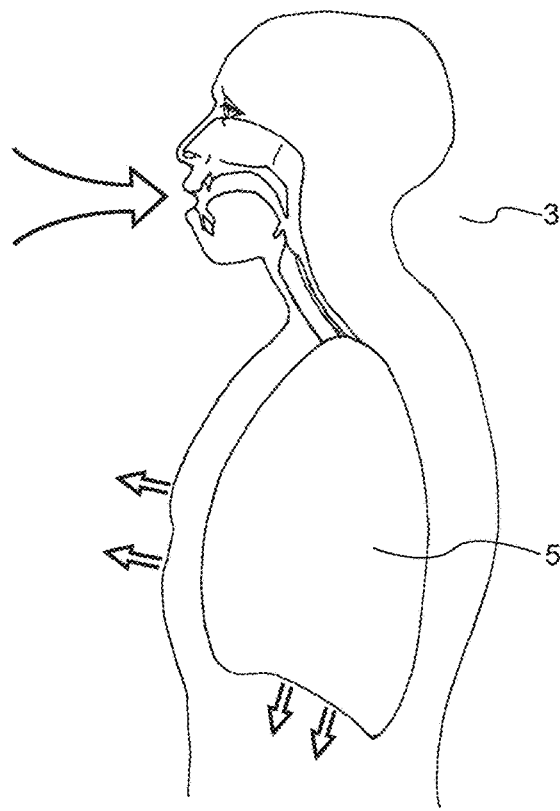
Figure 2B:
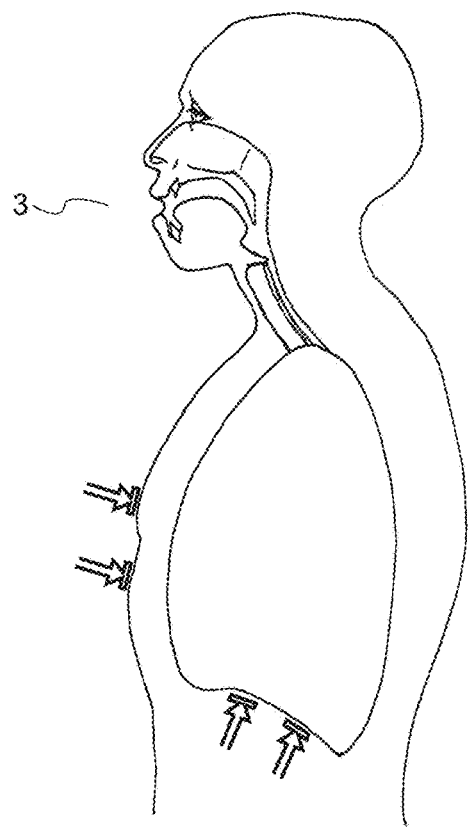
Figure 2C:
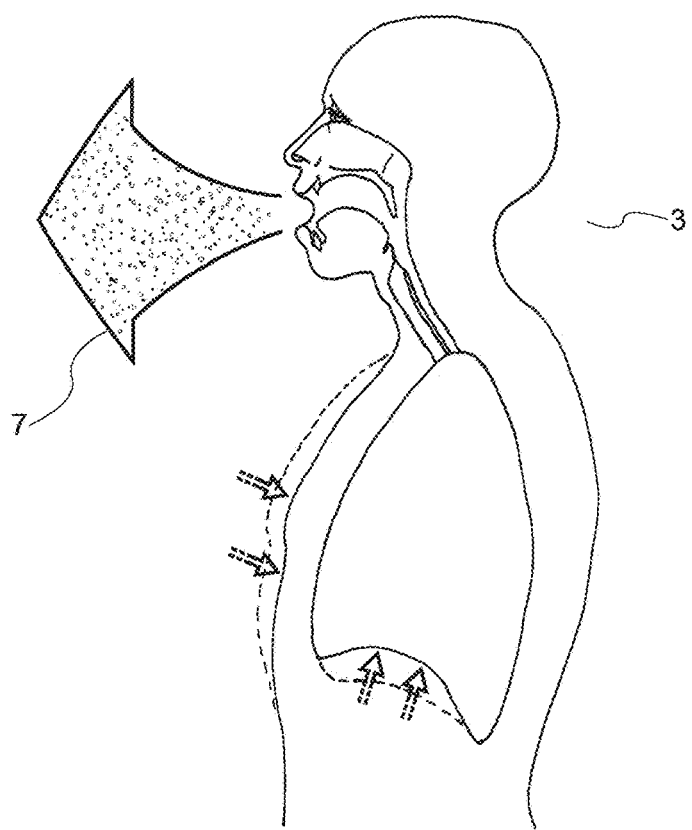
Figure 2D:
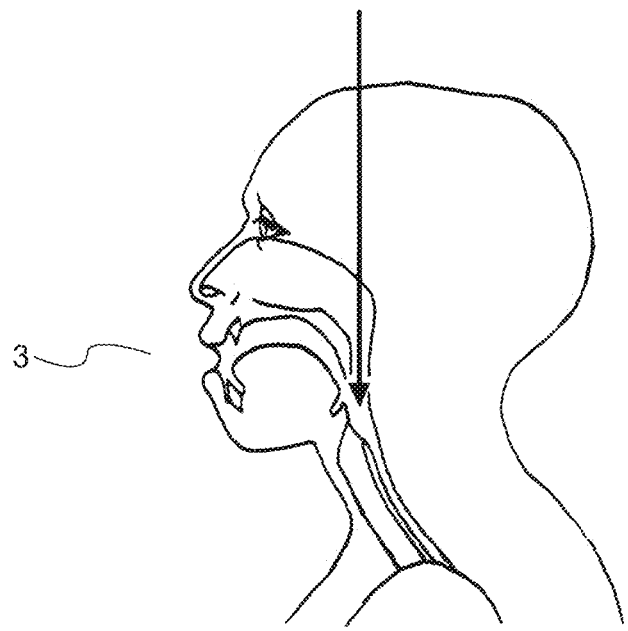
Figure 2E:
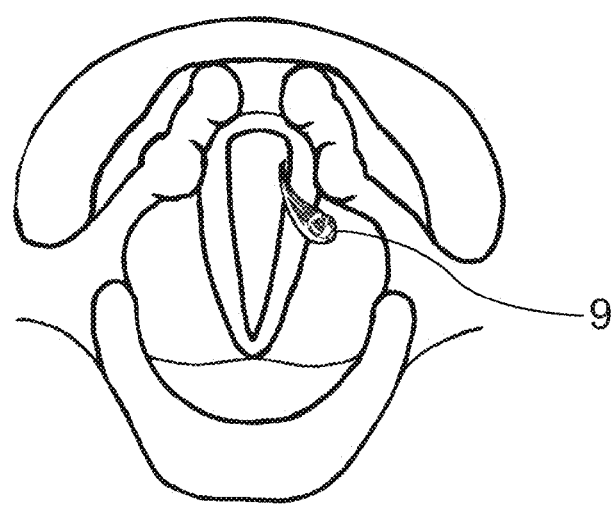

In more detail, FIG. 2A illustrates an inhalation phase of the cough function (typically triggered by airway irritation), which fills the lungs (generally at 5) with air. In the next stage of the cough function, shown in FIG. 2B, the glottis is closed, and the abdominal muscles are compressed, to create pressure. In the following stage of the cough function, shown in FIGS. 2C and 2E (the latter being a cross-sectional view through the oropharynx, at the position indicated by the arrowhead in FIG. 2D), the glottis is opened and a cough-cloud 7 is emitted. As part of this process, MLF 9 is transmitted from the vocal cords to the oropharynx (see FIG. 2E).

Figure 3:
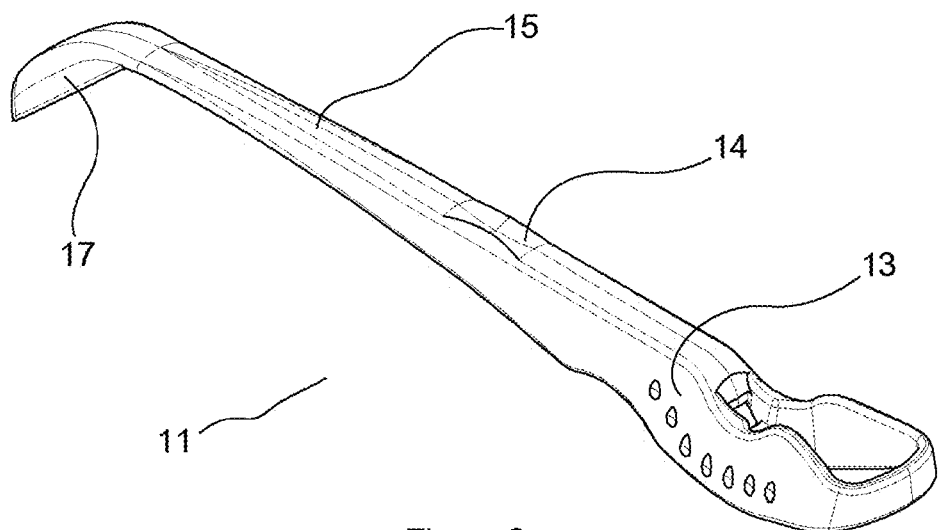
FIG. 3 shows a first embodiment of a sampling device according to the present invention.

A first embodiment of an airway sampling device 11 is shown in FIG. 3. The device 11 comprises a handle 13 to be gripped by a user (facilitated by a locator 14 provided on the upper surface of the handle 13 for contact with the user's forefinger), a stem 15 extending from the handle 13 and a sampling head 17 provided at the end of the stem distal from the handle 13, and angled relative to the longitudinal axis of the handle 13.

In the present embodiment, the handle 13, stem 15 and sampling head 17 are provided as an integrally formed, unitary body e.g. by moulding. An integrally formed stem 15, handle 13 and sampling head 17 is preferred to minimise the chances of any one of those components coming loose and being swallowed. However, in other embodiments, one or more of these parts of the sampling device 11 may be formed as separate parts which may then be attached, releasably or non-releasably, to the other parts to assemble the device. Also in the present embodiment, the sampling device 11 may be formed for example from plastics materials such as acrylonitrile butadiene styrene (ABS) or polypropylene (PP); however, different materials (either plastics or otherwise) may be used, as appropriate.

Figure 4A:
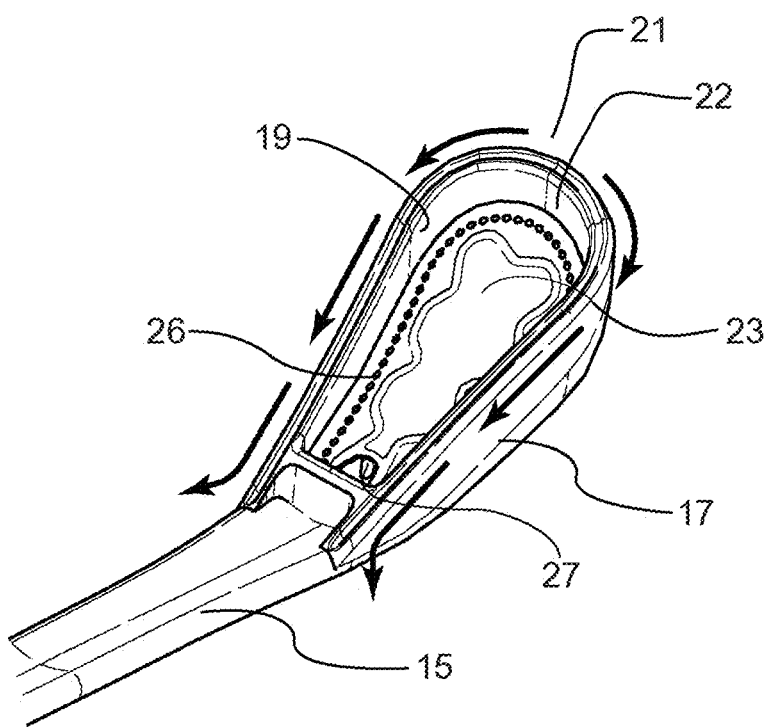
FIGS. 4A to 4C show details of a sampling head of the first embodiment.
Figure 4B:
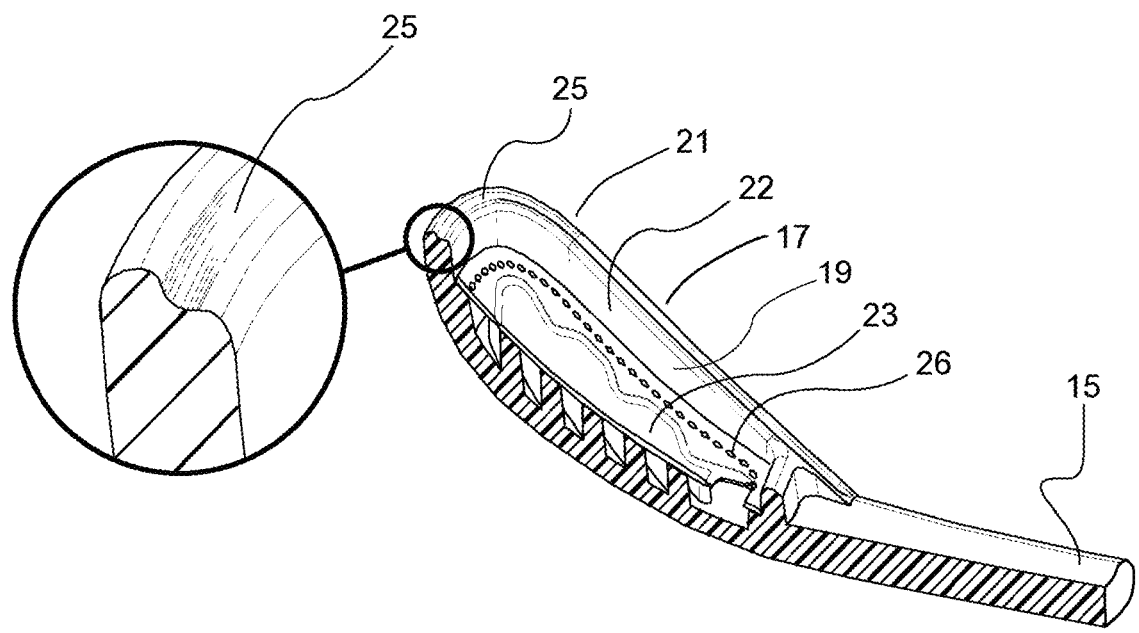

As shown in FIG. 4A (and in cross section in FIG. 4B), the sampling head 17 is provided with a perimeter wall 19 which extends generally perpendicularly to the axis of the stem 15 to create a protective hood 21 having a cavity or recess 22 to accommodate a sample collection membrane 23 in the form of a patch or small piece of (preferably absorbent and/or adsorbent) sampling material 23, to collect the sample from the subject 3. The perimeter wall 19 includes a gutter 25 around its upper edge, the purpose of which is explained later.

The sample collection membrane 23 of the present embodiment preferably comprises absorbent and/or adsorbent material, and may for example be Synthetic Absorptive Matrix (SAMT™) material. More generally, the sample collection membrane 23 materials could for example include, without limitation, a variety of synthetic and functionalised polymers in foam, fibrous or solid format. For example, and without limitation: polyurethane, fibrous hydroxylatred polyester (FHPE), polycaprolactone (PCL), nylon, cellulose acetate, cellulose, nitrocellulose, polyethersulfone, polysulfone, polypropylene, polyvinylidene fluoride (PVDF), polytetrafluoroethylene (PTFE), acrylic copolymer, white blood cell isolation media; also assay membranes for Point-of-Care (POC) diagnostics, lateral flow and flow through assays, blotting; also materials with antibodies and/or aptamers for diagnostic assays; and the like.

The sample collection membrane 23 is retained within the hood 21 by, but not limited to, adhesive bond, chemical weld, ultrasonic weld, or an overmoulding.

Figure 4C:
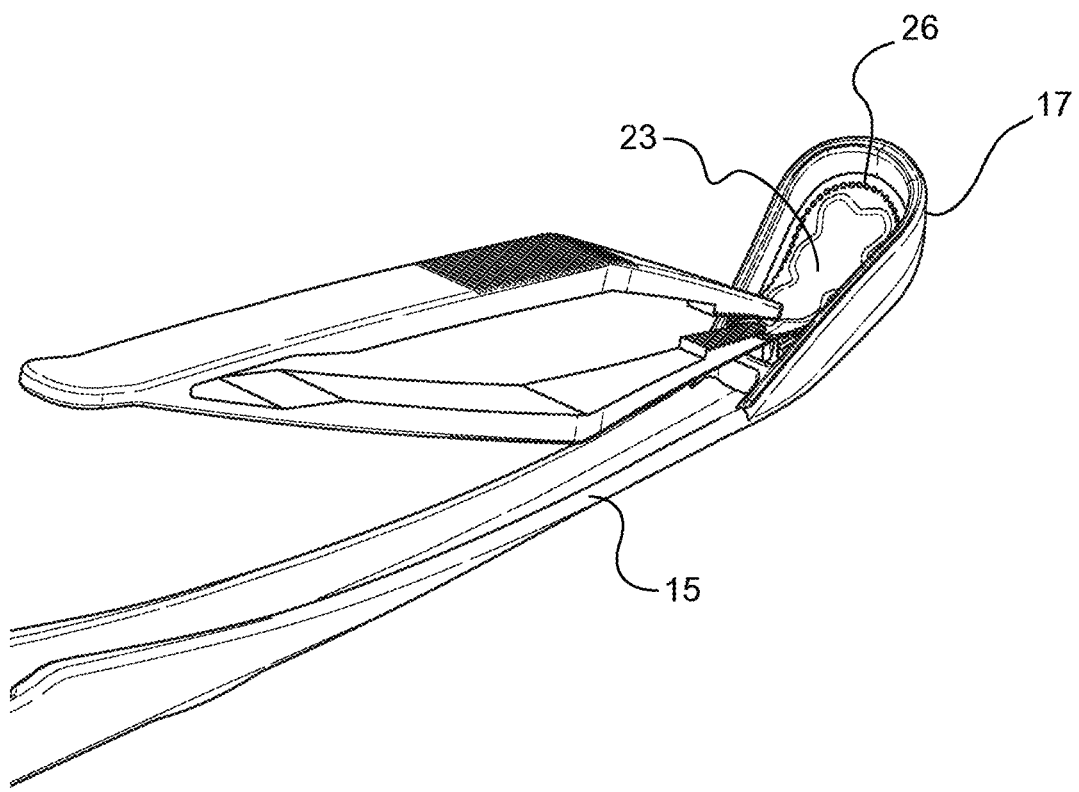

The sample collection membrane 23 is provided with an integral perforation 26 for its removal, post sample collection, with forceps or tweezers T, e.g. for analysis or retention by a clinician or other user (see FIG. 4C). To this end, the sample collection membrane 23 further includes a notch 27 at one end, to allow ready insertion of e.g. tweezers, to facilitate removal.

Figure 5A:
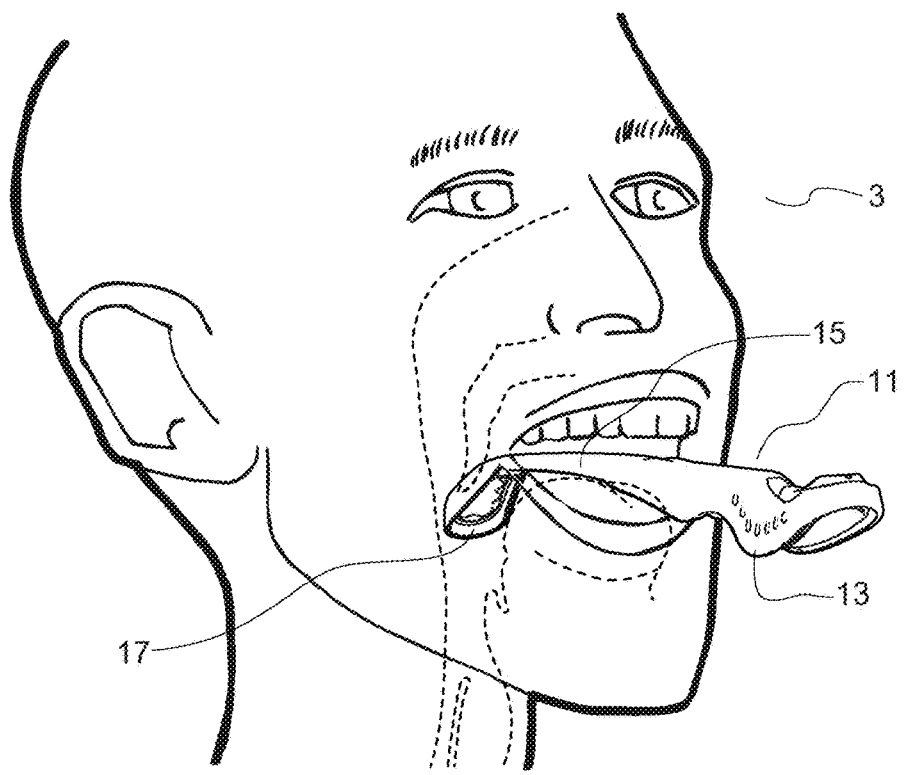
FIGS. 5A and 5B show the sampling device of the first embodiment in a sampling position within a subject.
Figure 5B:
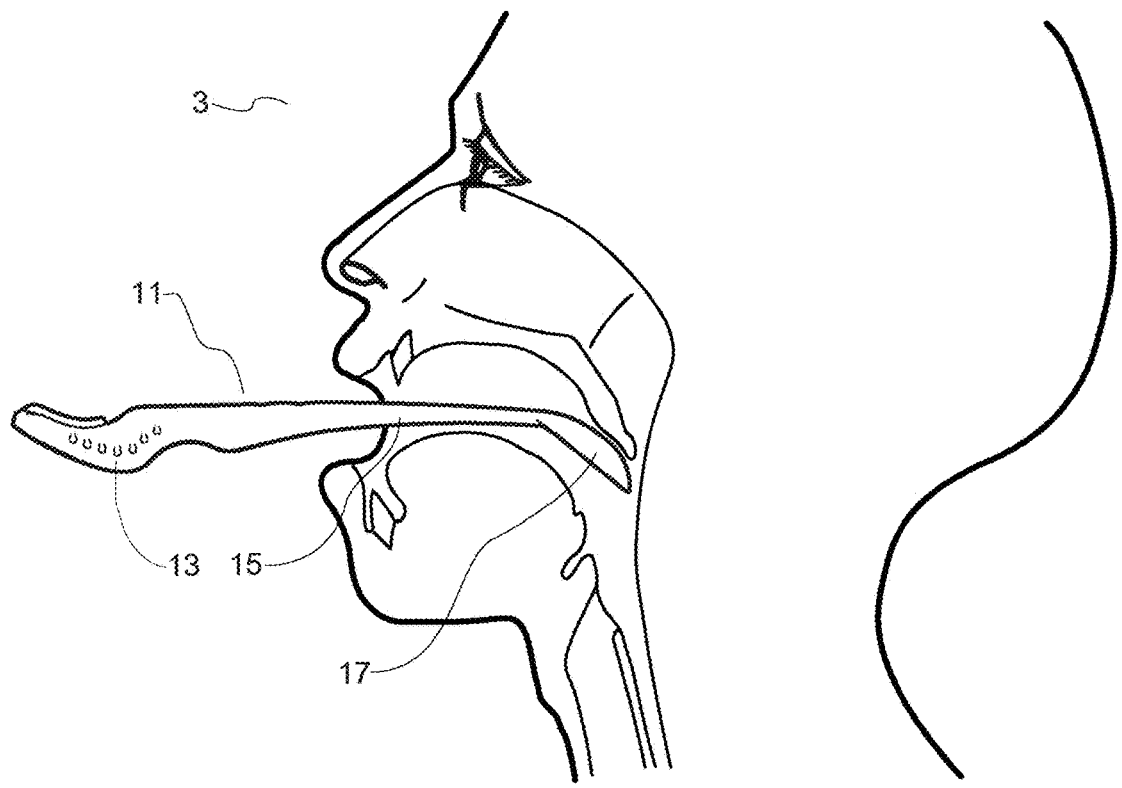

FIGS. 5A and 5B show the sampling device 11 in situ according to an airway sampling method aspect of the present invention. In this condition, the sampling head 17 is located at a sampling position according to the present embodiment, which sampling position is above (for example, a few centimetres above) the vocal cords of a subject 3, within the oropharynx and posterior to the uvula of the subject 3. This allows for MLF, uncontaminated (or with only minimal contamination) by saliva, to be adsorbed or absorbed onto the sample collection membrane 23 carried by the sampling head 17 when the subject is prompted to give a small cough or forced expiration (i.e. a short, sharp breath out).

The sampling device 11 of the present embodiment is specifically designed to facilitate the placement of the sampling head 17 into the sampling position shown in FIGS. 5A and 5B.

Firstly, various features of the sampling device 11 are dimensioned, angled and/or shaped to facilitate placement of the sampling head 17 into the sampling position shown in FIGS. 5A and 5B. In a preferred embodiment, different variants of the sampling device 11 are provided, each version being dimensioned, angled and/or shaped for usage with a subject, allowing ready placement by a user of the sampling head at the sampling position, based upon an age grading of the subject. Ultimately, the decision of which sized sampling device 11 to use will be determined by a clinician e.g. to account for a subject who is significantly larger or smaller than average for their age. However, the present embodiment seeks to provide, for example, three different sizes, intended for use by subjects coarsely graded according to three different age groups.

Figure 6A:
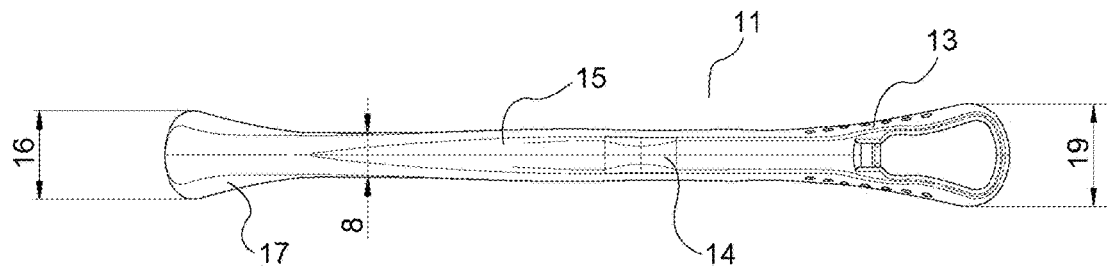
Figure 6B:
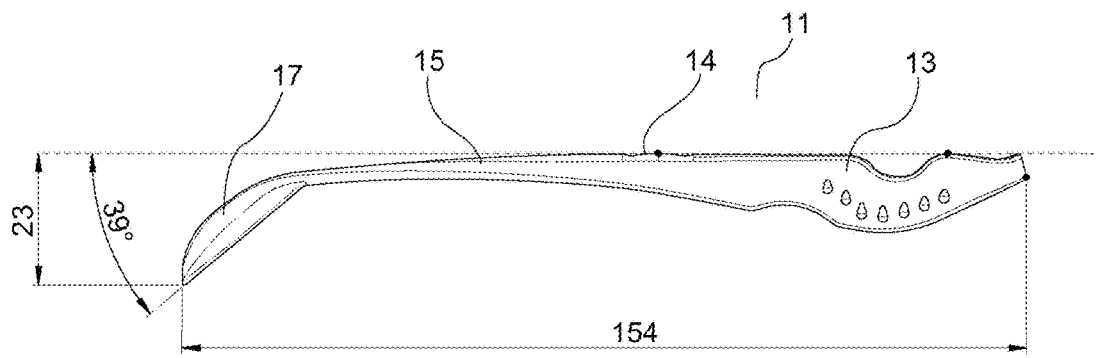
Figure 7A:
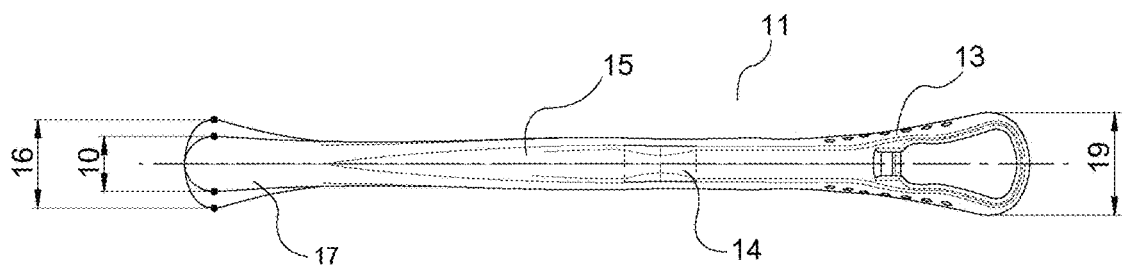
Figure 7B:
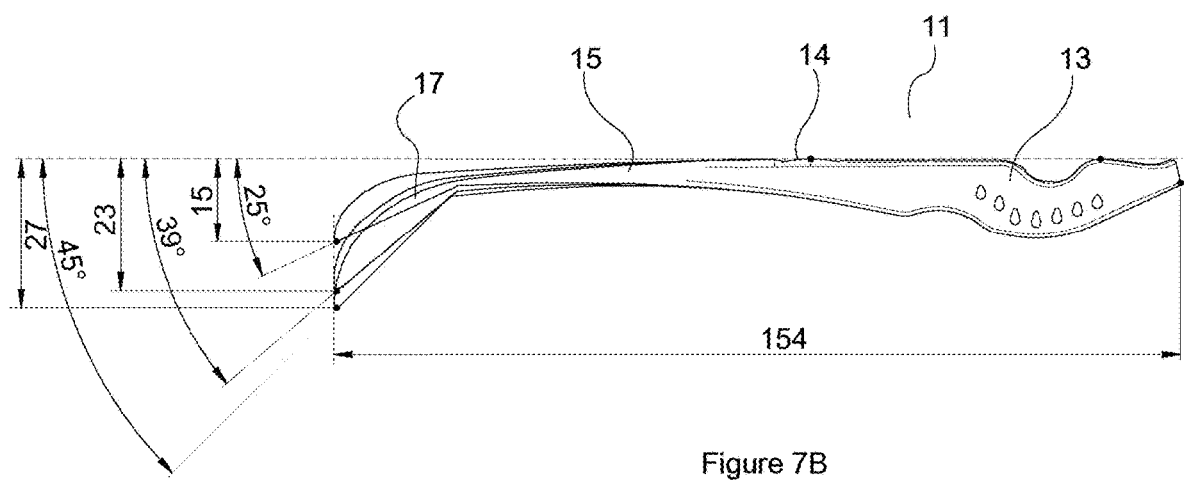

FIGS. 6A and 6B show dimensions (all in millimetres) and angles according to a currently most preferred embodiment for usage with an adult human subject (aged 16 or over); FIGS. 7A and 7B show preferred ranges for these dimensions (all in millimetres) and angles; FIGS. 7C and 7D show currently preferred dimensions (all in millimetres) and angles for a large-sized sampling device 11 intended for an adult subject (aged 16 or over); FIGS. 7E and 7F show currently preferred dimensions and angles for a medium-sized sampling device 11 intended for a subject aged between 12 to 15; and FIGS. 7G and 7H show currently preferred dimensions and angles for a small-sized sampling device 11 intended for a child subject (aged 8 to 11).

According to the present embodiment, the width of the sampling head 17 (this width being the dimension labelled in FIGS. 7C, 7E and 7G) is selected to maximise sampling material size (and hence maximising sample capture), without causing undue discomfort for a patient or subject 3. In particular, the width X of the sampling head 17 is designed so as to comfortably clear the corresponding distance X' between the tonsils of the subject 3 (see FIG. 8A) and especially to avoid and/or minimise interreference with the tonsils of a subject during the sample collection process, especially for a subject suffering from a viral or bacterial infection causing the tonsils to swell. In the present embodiment, the width ranges from 10 mm to 16 mm and, as an illustrative example only, may preferably be 16 mm for an adult/large sized device, 14 mm for an intermediate aged/medium sized device and 12 mm for a child/small sized device. A head width of 10 mm or more is advantageous, as it maximises sample capture and allows for a good-sized sample collection membrane 23 to be located within the protective hood 21 of the sampling head 17. A head width of 16 mm or less is also desirable, to avoid discomfort for the subject, and especially to avoid and/or minimise interreference with the tonsils of a subject during the sample collection process, especially for a subject suffering from a viral or bacterial infection causing the tonsils to swell.

Figure 8A:
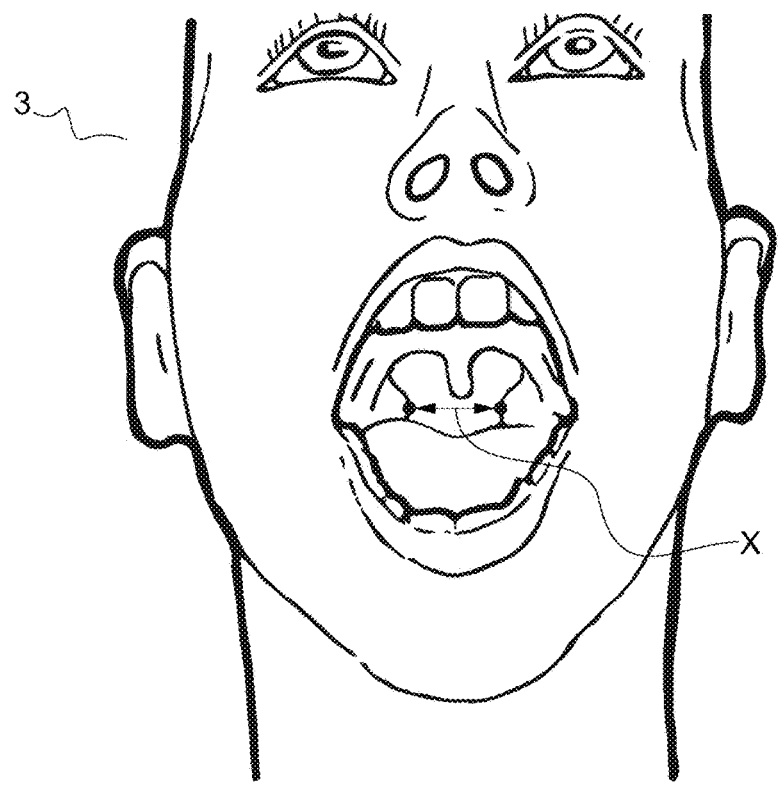
Figure 8B:
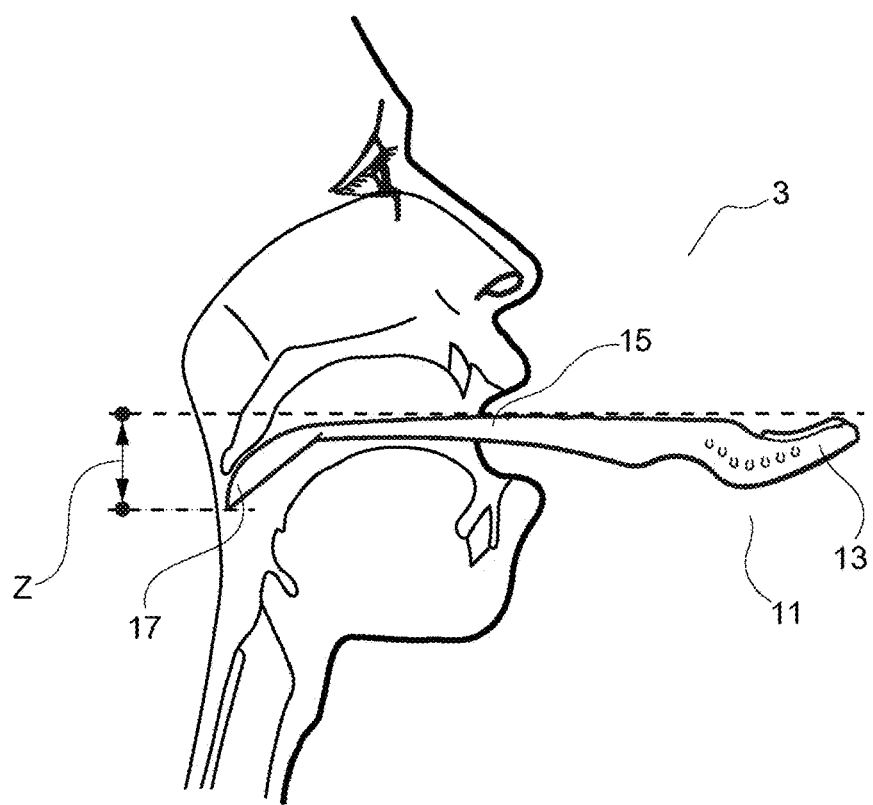
Figure 8C:
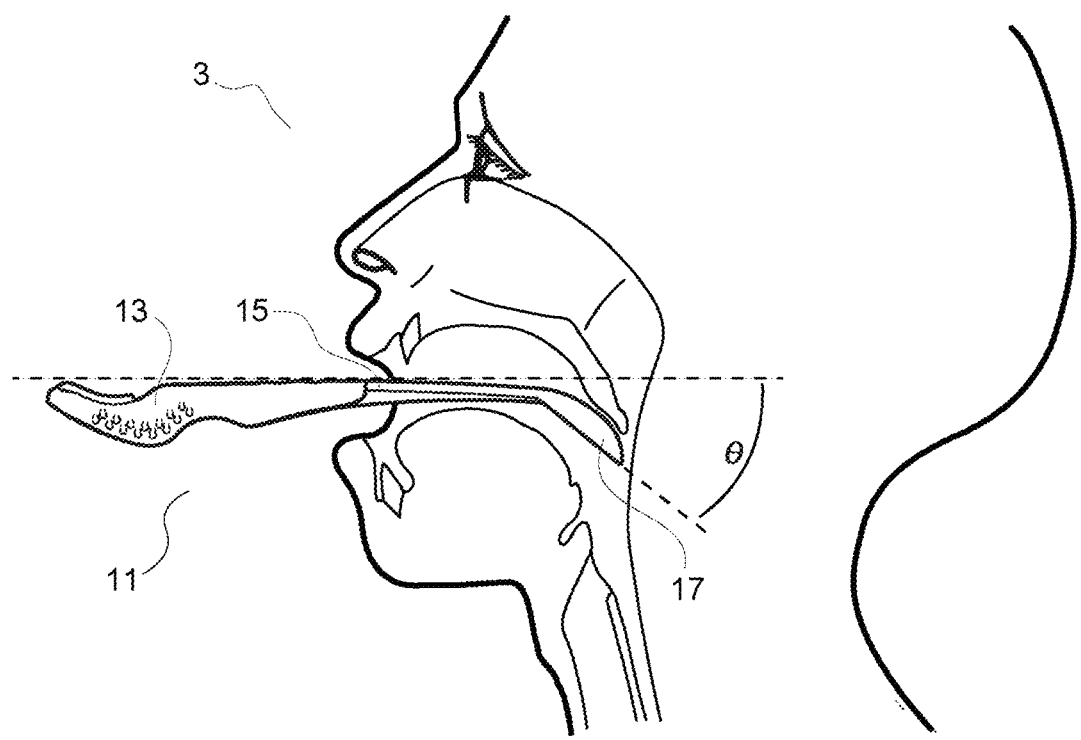

Next, and referring to FIGS. 8C and 8B, respectively, the open angle θ of the sampling head 17, along with the overall vertical depth Z of the sampling device 11 (measured from the uppermost point of the sampling device handle 11 to the lower-most point (the tip) of the downwardly-angled sampling head 17), are designed to maximise the sampling material sampling area (i.e. to maximise the exposure to expelled MLF), without significantly restricting airflow. Here, the "open angle" of the head 17 means the angle θ of the sampling head 17, and more specifically the plane of the opening of the recess 22 within the hood 21 (which plane also preferably corresponds to the plane of the sample collection membrane 23) relative to horizontal, when the sampling device 11 is positioned in situ in the sampling position shown in FIG. 8C, with the sampling head 17 located at the desired sampling position (i.e. above the vocal cords within the oropharynx, posterior to the uvula). In the present embodiment, the preferred range of open angle θ° of the sampling head 17 is 25° to 45°, with a most preferred angle of 39°, regardless of the age of the subject.

Figure 9:
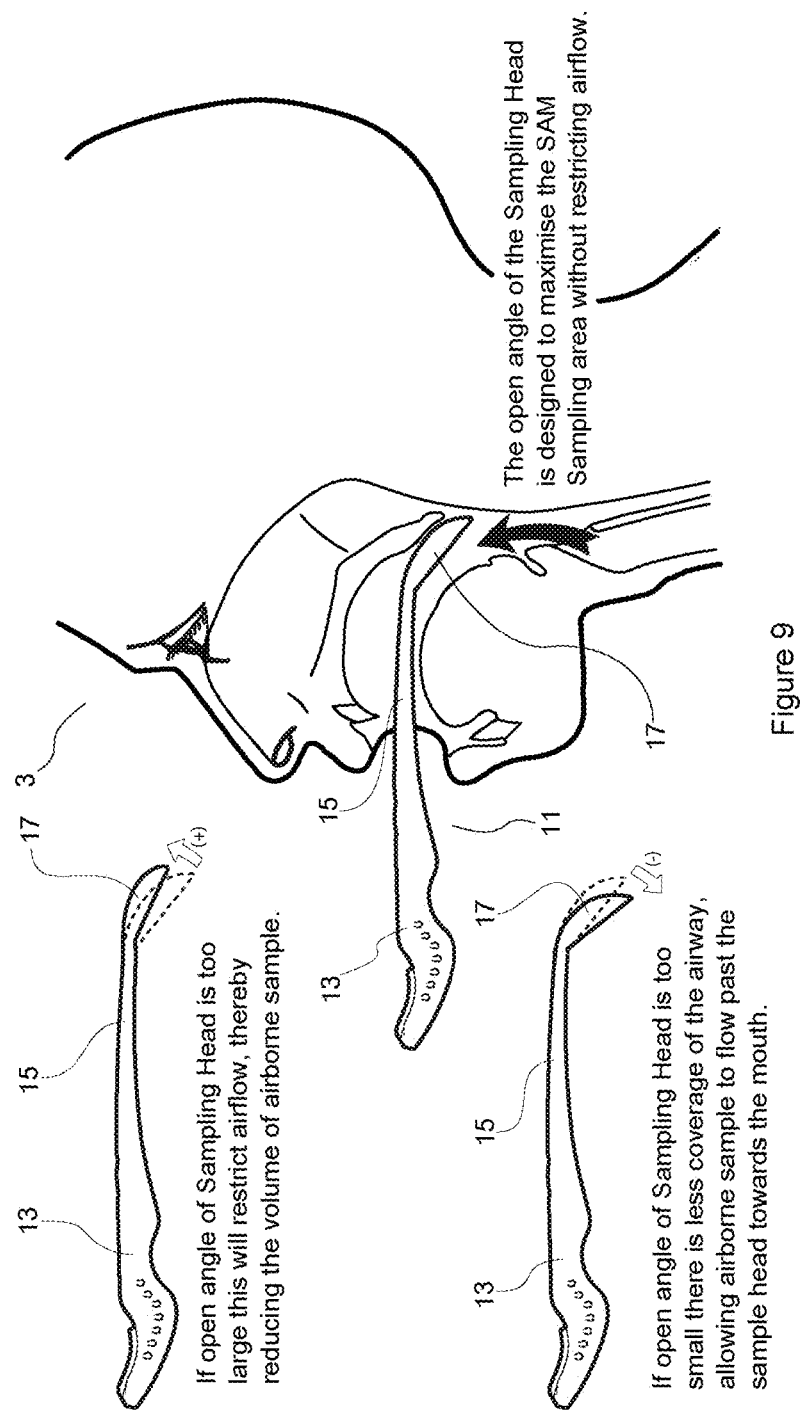

Here, and as explained with reference to FIG. 9, an open angle of at least 25° relative to horizontal is preferred, to avoid significantly restricting the airflow of the subject (and hence to avoid reducing the volume of the airborne sample). On the other hand, an open angle of 45° or less relative to horizontal is preferred, to avoid reducing the amount of airborne sample landing on the sample collection membrane, either as a result of sample escaping around the back of the sampling head 17, without coming into contact with the sample collection membrane 23, or simply impinging upon the protective hood 21 of the sampling device 11. As shown in FIG. 10, the preferred angling and length of the sampling head 17 maximise airflow and the amount of sample impacting on the sample collection membrane 23.

The overall depth Z of the sampling device 11 is preferably varied according to the age of the subject; purely as an illustration, for a sampling device 11 intended for use with an adult (aged 16 or over), the depth Z may for example be 23 mm; for a sampling device 11 intended for use with an intermediate-aged subject adult (aged 12 to 15), the depth Z may for example be 20 mm or 21 mm; for a sampling device 11 intended for use with a child (aged 8 to 11), the depth Z may for example be 17 mm.

The following table 1 recites currently preferred optimal values for the head width X, depth Z and sampling head angle θ. It is however to be appreciated that the following preferred optimal values, as well as all of the foregoing described angles and dimensions, are strictly non-limiting and illustrative only, and that other angles and dimensions may be used as appropriate.

TABLE 1

| Optimal Sizes | Age | X | Z | θ |
| --- | --- | --- | --- | --- |
| Small | 8-11 | 12 | 17 | 39° |
| Medium | 12-15 | 14 | 20 | 39° |
| Large | 16+ | 16 | 23 | 39° |

Next, and also with reference to FIG. 10, the outside surface 29 of the sampling head 17 is smooth and radiused so as to readily deflect the uvula 31 of the subject 3 towards the rear of the oropharynx, allowing the sampling head 17 to adopt the optimal sampling position shown in FIG. 10, centrally above the airway of the subject. For example, and simply as an illustration, a mid-point of the outside surface of the sampling head 17 may present the angles such as shown in FIGS. 7D and 7F (38° and 36° relative to horizontal when in the sampling position, respectively) to facilitate deflection of the uvula. However these angles are merely illustrative and other angles nay be used, as appropriate.

The sampling head 17 is further configured to minimise and/or eliminate sample collection membrane contamination e.g. from saliva or from lymph fluid from the tonsils. Firstly, and as explained above, the sampling head 17 is provided with a wrap-around hood 21 which encloses the sample collection membrane 23 on all sides (other than at the opening to the recess within the hood 21), and hence enables the sampling head 17 to push past the tonsils, to upwardly deflect the uvula, and potentially to also contact the back of a subject's throat, without any (or with only minimal) fluid contamination of the sample collection membrane 23. To prevent direct surface contact contamination from these areas the outer surface of the hood 21 is designed to be perpendicular to these landmarks, as shown in FIG. 11, during placement, sample capture, and removal of the sampling device 11 from the subject's airway.

As a further measure, and as noted above, the hood 21 is provided with an integral gutter 25. When the sampling device 11 is inverted for sample processing, there is a risk that fluids such as saliva or lymph fluid could flow over the peripheral edge of the sampling head 17, potentially contaminating the sample collection membrane 23. The integral gutter 25 avoids or ameliorates this risk by capturing these fluids, and allowing them to safely drain away as indicated by the pointed arrows in FIG. 4A. Flow is gravity fed and dependent on fluid viscosity, and allows fluid to drain off safely outside of the sampling area of the sampling device 11.

In addition to the design of the sampling head 17, the stem 15 is designed to be thin to minimise contact with the tongue and mouth of a subject 3, thus minimising the gag reflex. For example, and as illustrated in FIG. 6A, the stem width may preferably be 8 mm, for a sampling device 17 intended for use with an adult. Also, the sampling device 11 is preferably flexible, to minimise accidental trauma to the subject under testing.

In summary, the sampling device 11 of the present embodiment is designed to position the sample collection membrane in the oropharynx (behind the uvula), protected from saliva and other fluids from the mouth, tongue and uvula. On coughing, the sample collection membrane 23 catches (by impingement) tiny droplets of MLF from the vocal cords and originating from the lower airways.

An airway sampling method according to an embodiment of the present invention, using the sampling device 11 described above, will now be described with reference to FIG. 12.

As a preliminary step 1201, the back of the subject's throat is sprayed with lignocaine or other local anaesthetic, to minimise discomfort and to reduce the risk of a gag-reflex.

Next, at step 1202, and with the subject's mouth wide open, the sampling head 17 of the sampling device 11 is inserted into the patient's mouth, taking care to avoid saliva contamination to the sampling material from the tongue. Although not necessary, a tongue depressor may optionally be used during this step, to depress the tongue of the subject for greater visibility of the mouth and throat.

At step 1203, the rear surface of the sampling head 17 is used to upwardly lift the uvula, as necessary, so that the sampling head 17 is positioned centrally over the subject's airway, and in particular over the subject's vocal chords, within the oropharynx and posterior to the uvula.

Next, at step 1204, the subject is prompted to cough or give a forcible expiration (i.e. a sharp exhalation). As explained above, this results in MLF expelled from the vocal cords to be collected, uncontaminated (or with only minimal contamination) from saliva and other fluids.

Finally, at step 1205, the sampling device is removed from the patient's airway, allowing the sample collection membrane 23 to be removed from the sampling head 17 e.g. for analysis or storage.

A second embodiment of a sampling device 11 according to the present invention is shown in FIG. 13, in which the same or similar features are given the same reference numerals, and only the differences from the first embodiment will be described. As explained in the following, the primary distinction is that the second embodiment allows for an integrated sample washing and elution function.

Figure 14A:
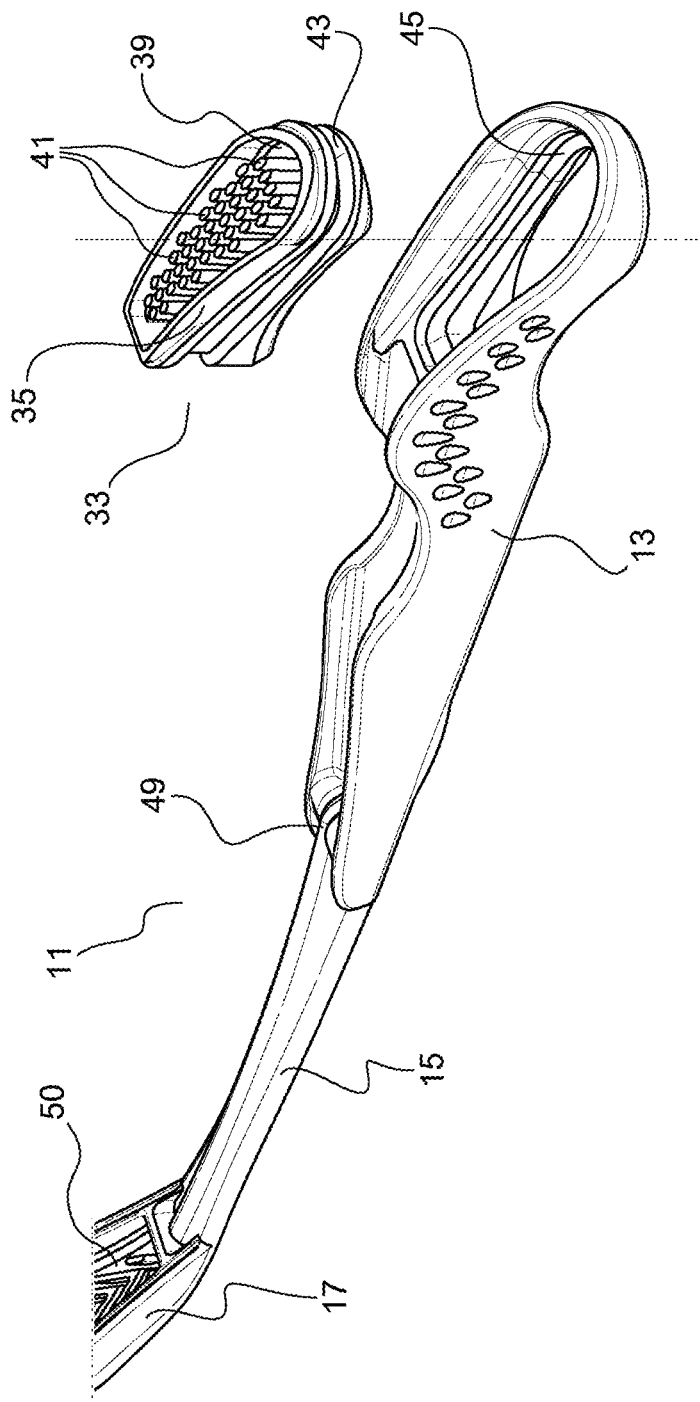
Figure 14B:
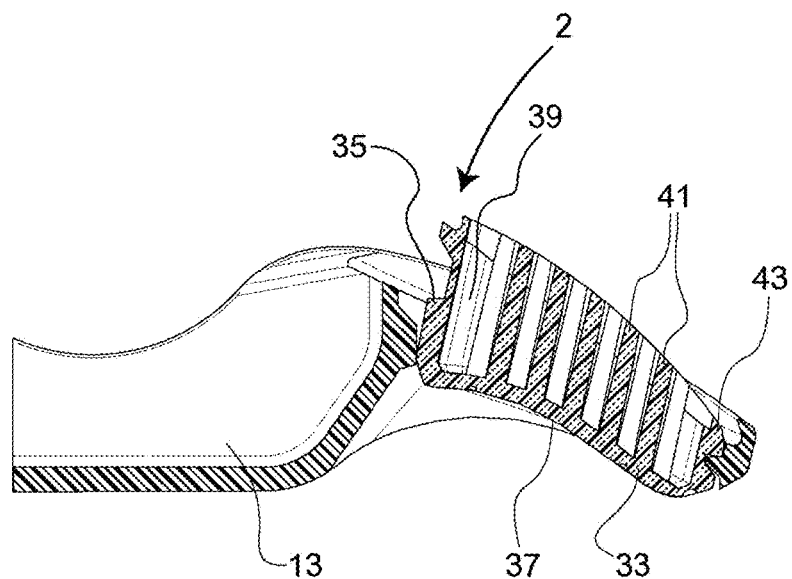
Figure 14C:
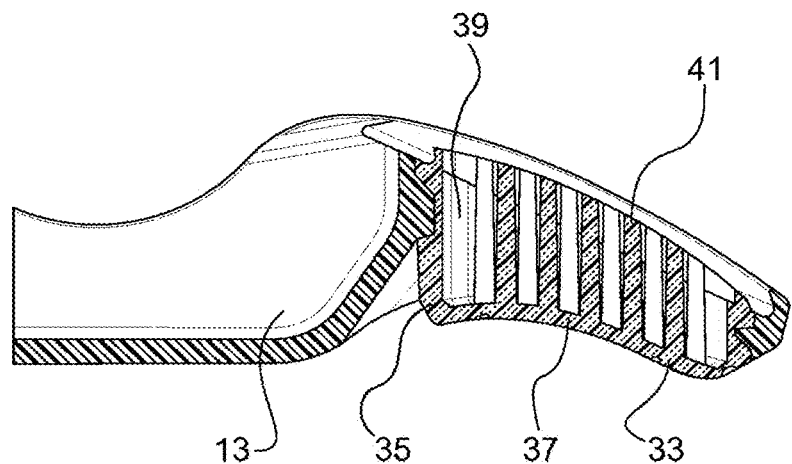
Figure 14D:
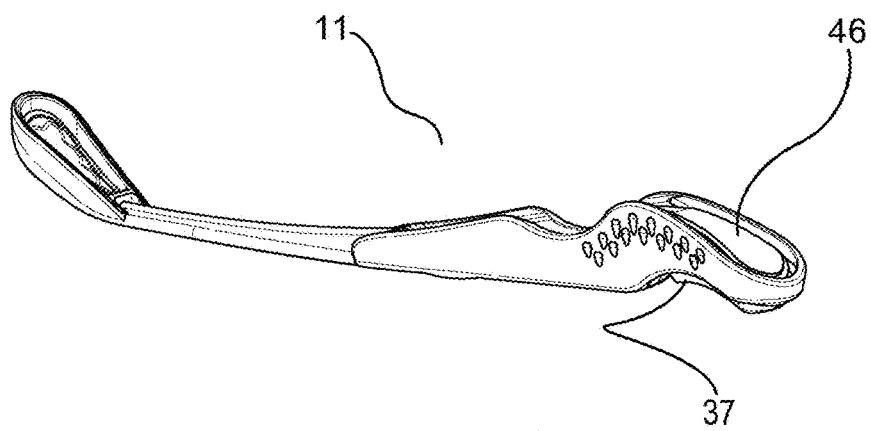
Figure 35:
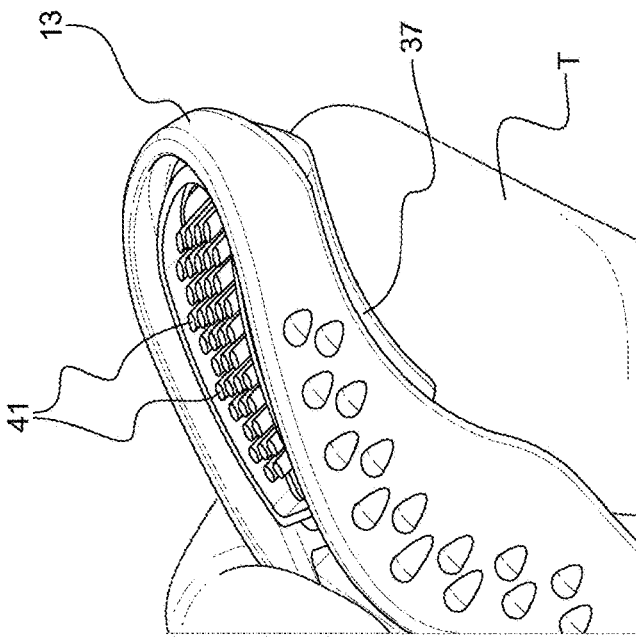

To this end, and unlike the first embodiment, the second embodiment is firstly provided with a washing and elution chamber 33 at the far end of the handle. As best shown in FIGS. 14A to 14C, the washing and elution chamber 33 has a perimeter wall 35 upstanding from and surrounding the entire circumference of a bottom wall 37, to define a cavity 39 within. Within the perimeter wall 35, a plurality of upstanding columns 41 are provided, spaced at regular intervals. In use, and as explained below, the chamber 33 is designed to be compressed (i.e. squeezed) by a user, as part of the sample washing and elution function. The 41 columns push in a spreading motion against the saturated sample collection membrane (e.g. SAM) to maximise the recovery of the eluted MLF, when the user compresses the chamber 33 e.g. with their thumb T, as shown in FIGS. 35 and 36. Accordingly, the chamber 33 is preferably formed from a deformable, resilient material (such as thermoplastic vulcanizate, TPV, although other suitable materials may equally be employed). In the present embodiment, the chamber 33 is further provided with a peripheral undercut feature 43 which locates over an annular flange 45 within the handle, holding the chamber 33 in place, with the bottom wall 37 protruding from the handle 13 to define a button, to facilitate squeezing of the chamber 33 by a user. The outer surface of the bottom wall 37 is provided with a roughened or textured area 41 to facilitate a user's steady grip on the bottom wall 37 during squeezing of the chamber 33. Preferably, the opening of the chamber 33 is closed by a removable protective cover 46 (see FIG. 14D), to prevent/reduce contamination risks prior to and during the sample collection process. The bottom wall 37 of the chamber 33 is further provided with a generally circular weakened area 47 of reduced thickness (see FIG. 13), the purpose of which is explained later.

Figure 15A:
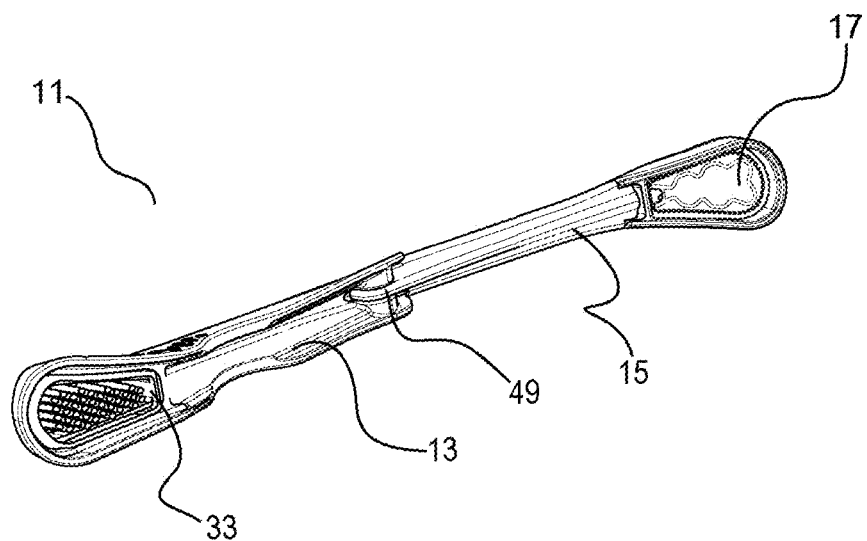
Figure 15B:
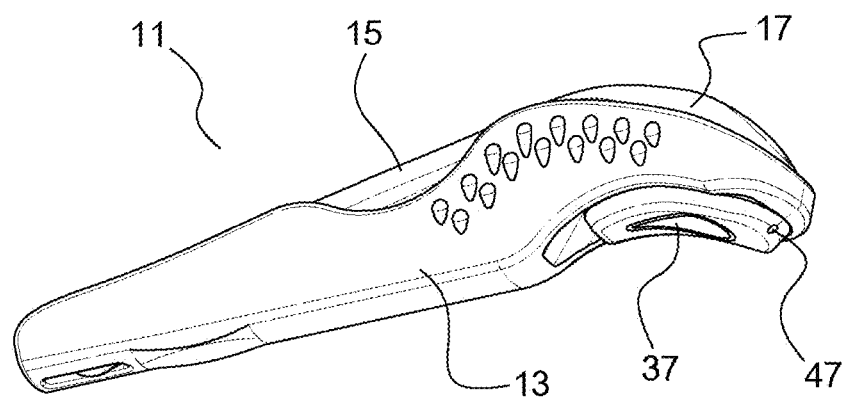
Figure 15C:
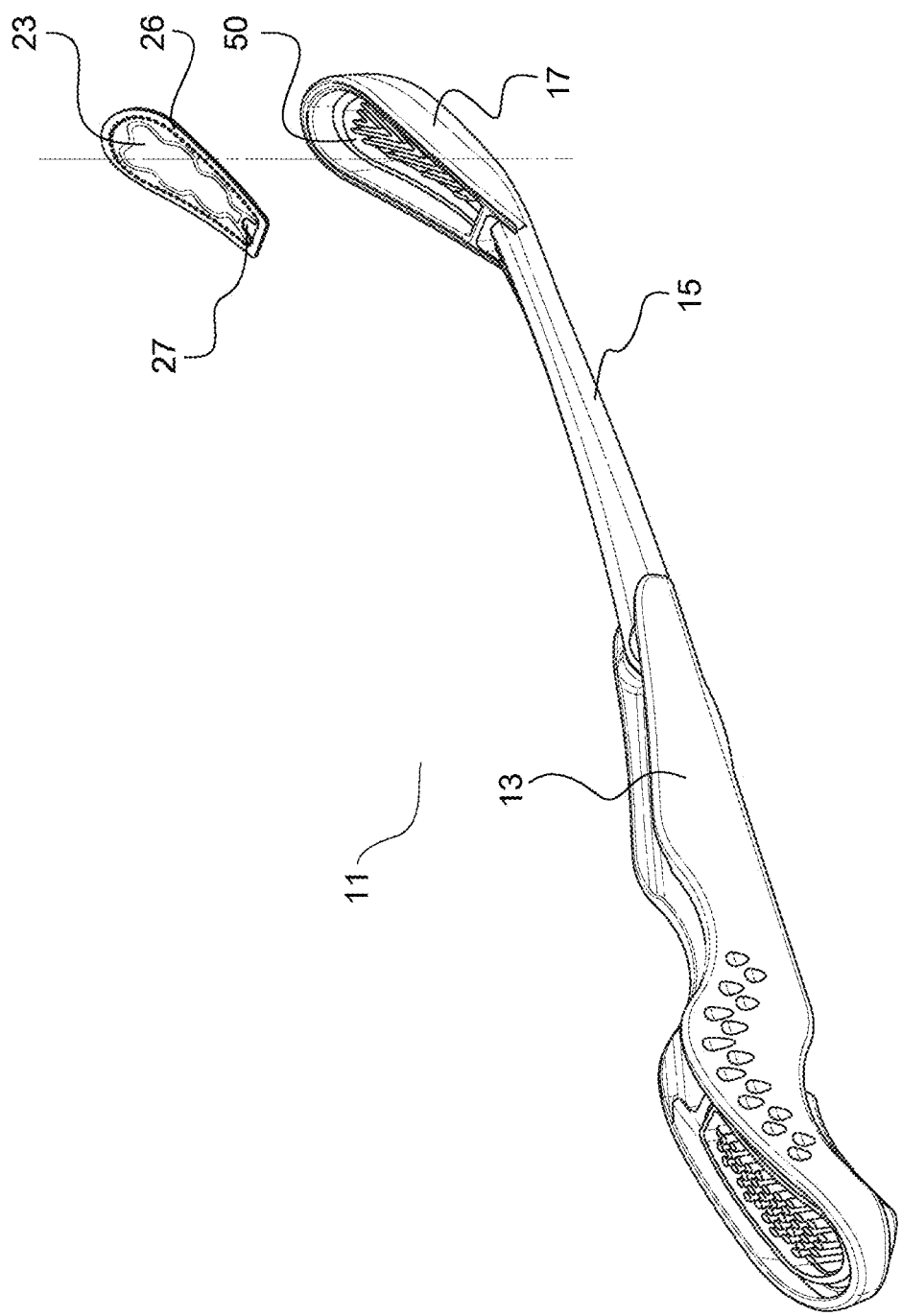
Figure 15D:
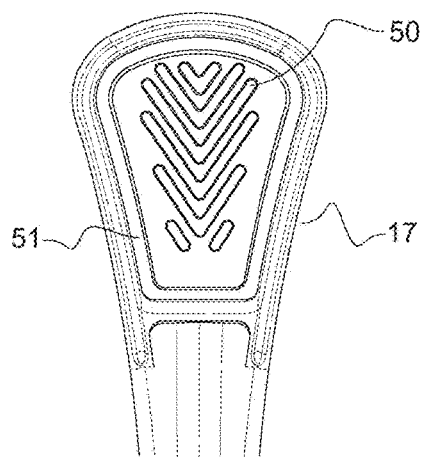
Figure 15E:
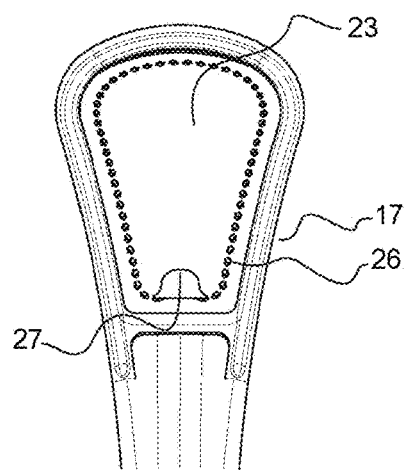
Figure 15F:
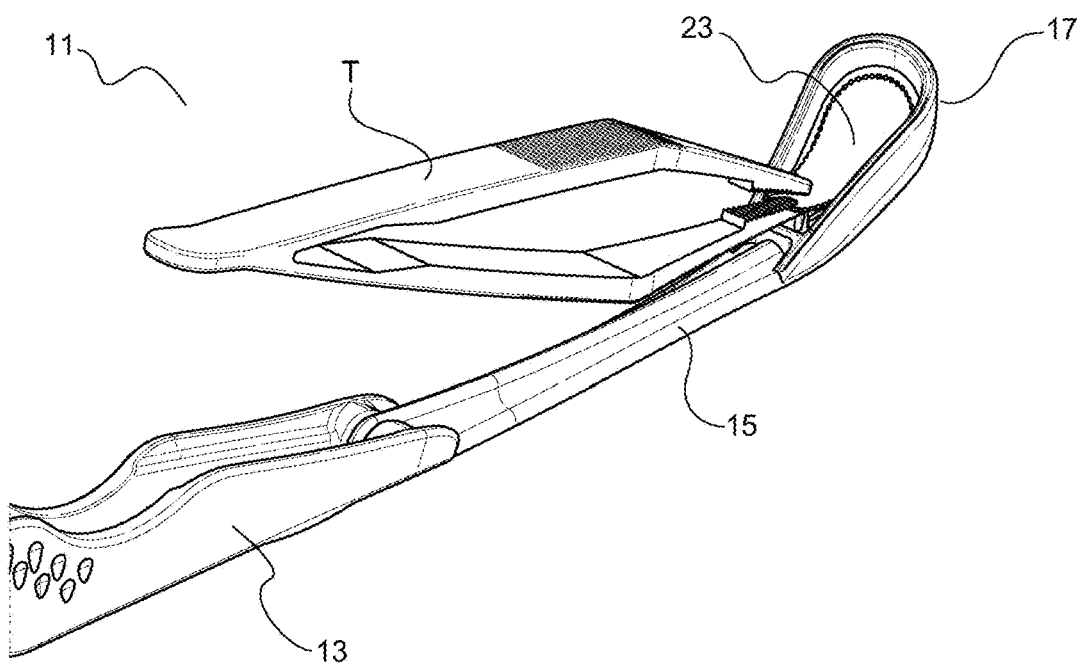

Secondly, the device 11 of the present embodiment is provided with a hinge 49 connecting the handle 13 to the stem 15 (see FIG. 15A), and thus permitting the stem 15 and sampling head 17 to be rotated relative to the handle 13 between the unfolded condition shown in FIG. 13 or FIG. 15A (for use in sample collection) and a folded condition as shown in FIG. 15B (for sample washing and elution, as well as sample storage and, optionally, initial shipping).

Figure 15G:
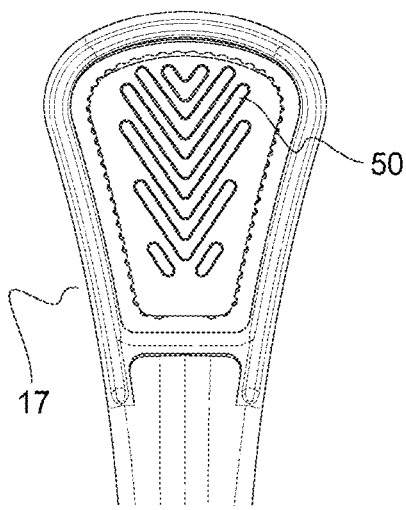

As in the first embodiment, the sampling head 17 of the present embodiment is configured to carry a sample collection membrane 23 such as a piece of absorbent and/or adsorbent sampling material (e.g. SAM™), to collect a sample from a subject's airway. In this embodiment, however, the interior of the sampling head 17 is further provided with a series of protrusions 50, arranged in a chevron pattern (see FIGS. 15C and 15D), on which the sample collection membrane 23 is placed, with its edges located on a peripheral ledge 51 of the interior head surrounding the chevron-patterned protrusions (see FIG. 15E). The sample collection membrane 23 may be attached to the peripheral edge of the sampling head 17 by, but not limited to, adhesive bond, chemical weld, ultrasonic weld, an overmoulding. Again, the sample collection membrane 23 is provided with an integral perforation 26 for optional removal with forceps or tweezers T (see FIG. 15F); FIG. 15G shows the interior of the sampling head 17 with the sample collection membrane 23 removed.

As shown in FIGS. 16A to 16G, the hinge 49 is preferably a snap-fit hinge, in which the stem 15 and sampling head 17 assemble to the handle 11 via a snap-fit. To assemble, the hinge centre 51 of the stem 15 is pushed between hinge studs 53 provided in the handle 13, which causes the handle sides to flex rotate, allowing the stem 15 to pass the hinge studs. When the hole 55 at the hinge centre of the stem 15 and the hinge studs 53 in the handle 15 are in-line, the pre-loaded force within the flexible sides of the handle 15 force the hinge studs to snap-in, captivating the hinge assembly.

Preferably, tapered hinged studs 53 are used. Tapered studs offer two advantages—firstly, they significantly improves assembly; secondly, the increased surface area contact gives the hinge greater transverse stability.

In the present embodiment, the hinge centre of the stem 15 is designed with a deliberate interference, therefore, once assembled, there is a frictional contact between both components (stem 15 and handle 17).

Figure 16A:
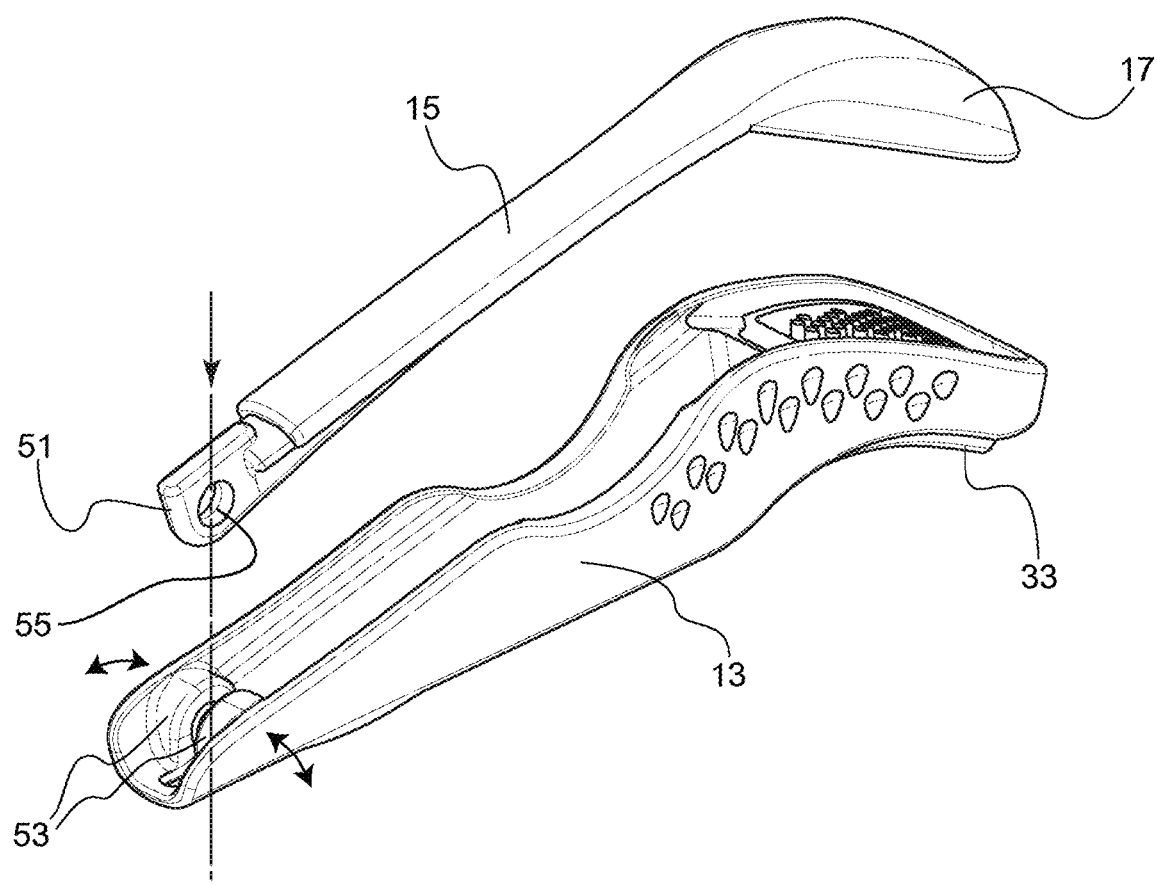
Figure 16B:
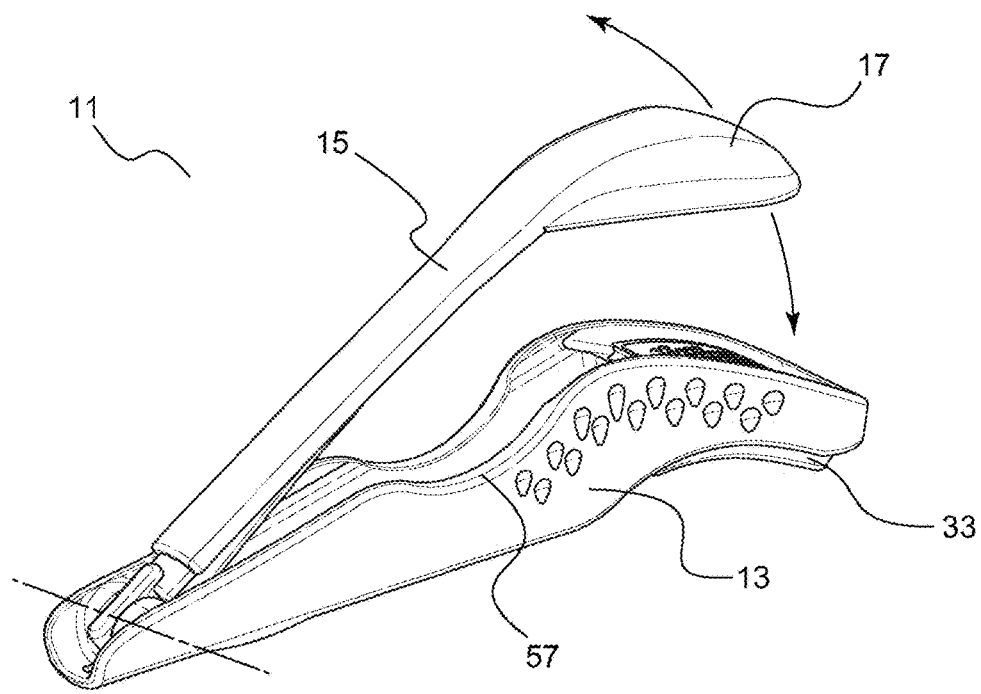
Figure 16C:
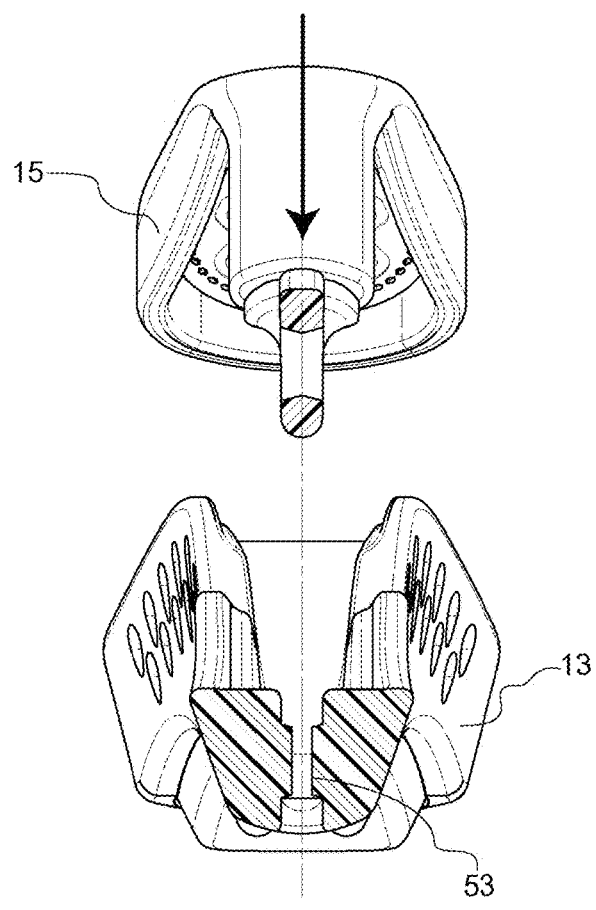
Figure 16D:
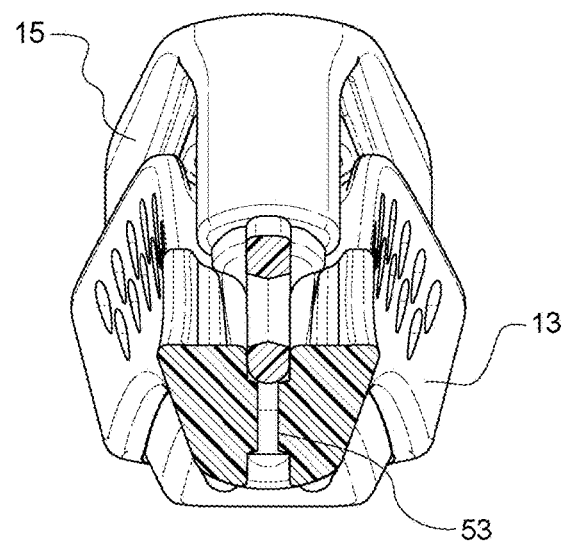
Figure 16E:
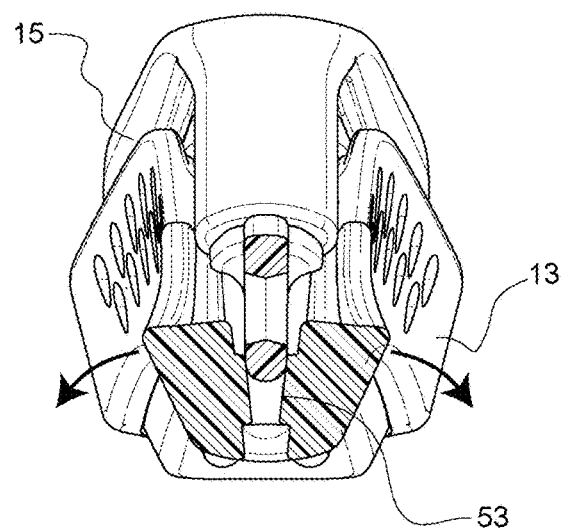
Figure 16F:
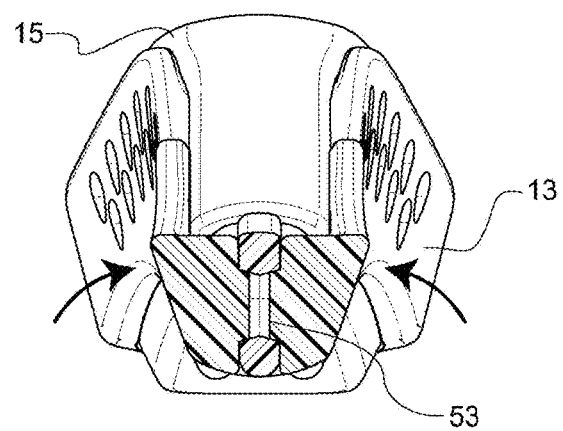
Figure 16G:
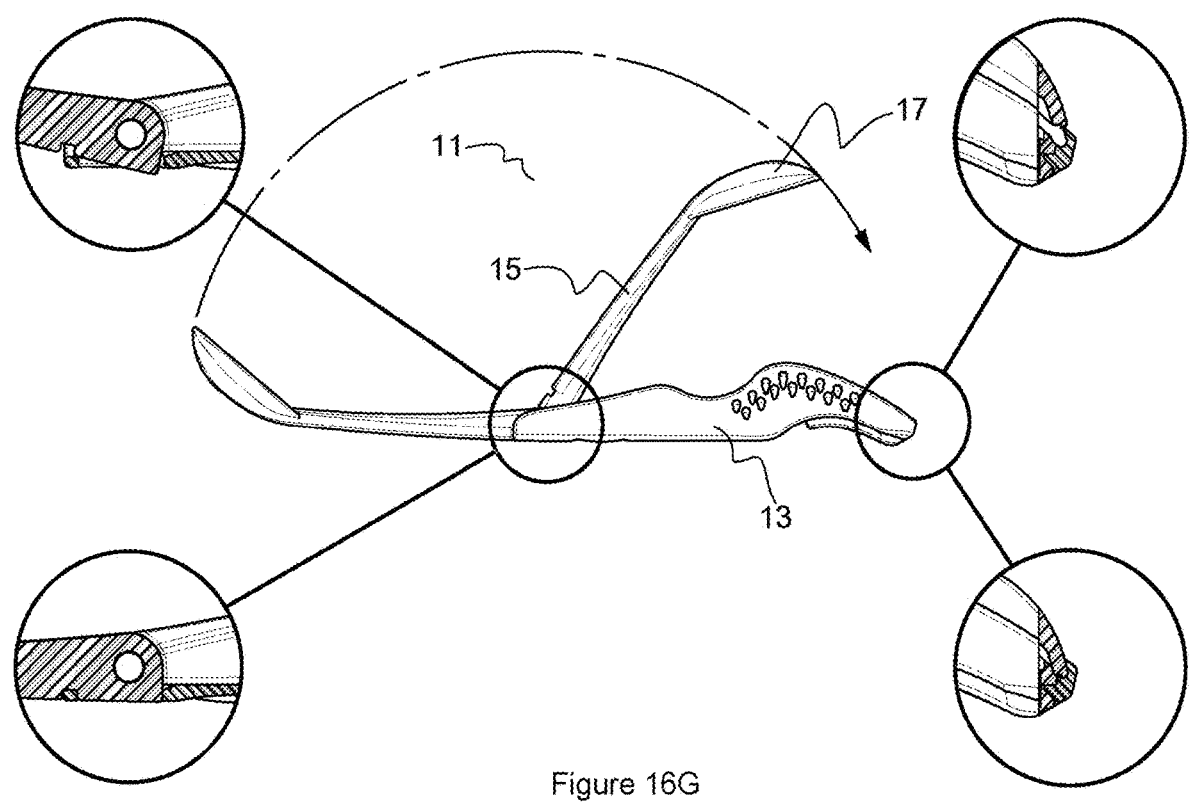

Once assembled, and as shown in FIG. 16G, there are two positional snap-fits, 165° apart, one in the extended "sampling" position and the other in the housed "washing and elution" position. Movement between these positions is facilitated by the scalloped finger locater curves 57 provided in the handle 17 (see FIG. 16B).

Figure 18A:
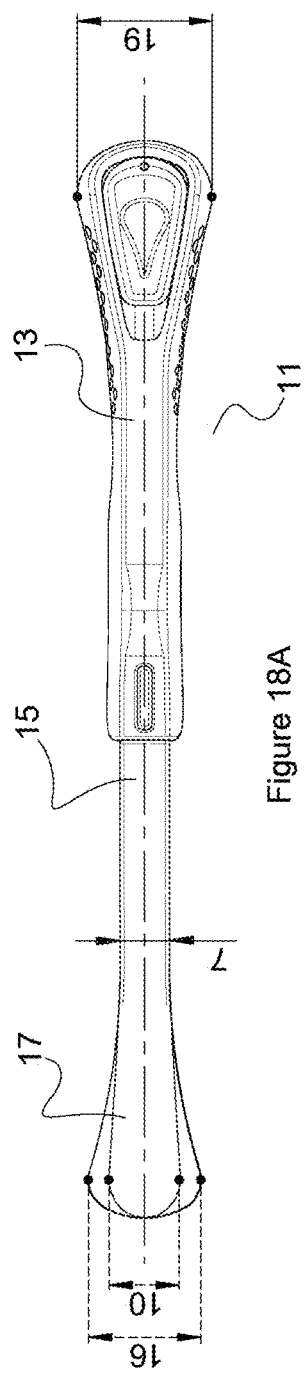
Figure 18B:
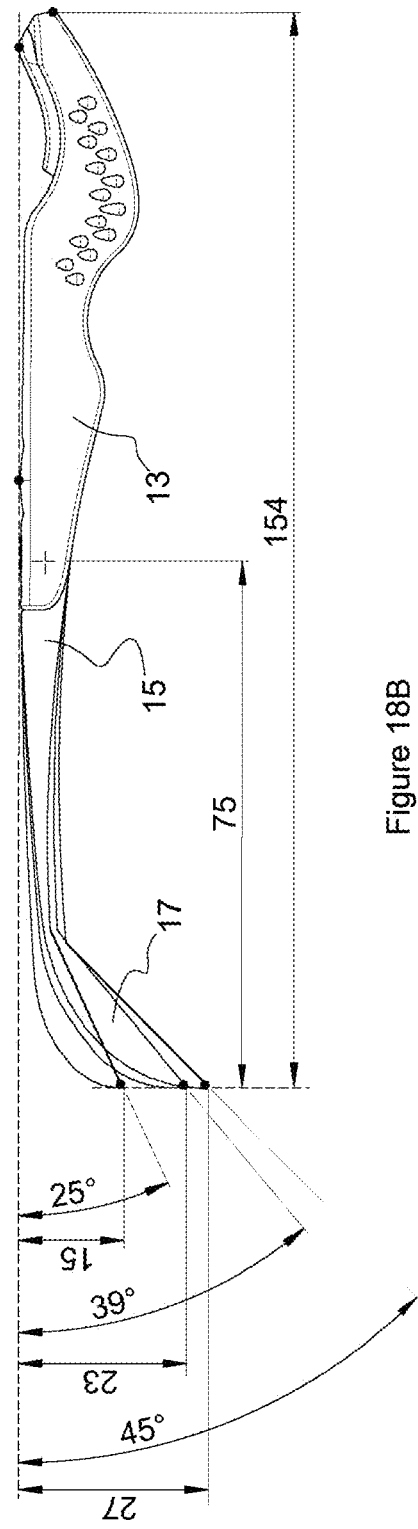

As with the first embodiment, the present embodiment may be provided in different sizes, shapes and dimensions for usage with different sized-subjects, preferably based as a guideline on the age of the subject. As with the first embodiment, for example, an adult/large size sampling device 11 may be produced for preferred use with a subject aged 16 or over—see FIGS. 17A and 17B, 18C and 18D for (merely illustrative) preferred dimensions and angles, with a preferable range of dimensions and angles as shown by FIGS. 18A and 18B. Further, a medium sized device 11 may preferably be dimensioned and angled as shown in FIGS. 18E and 18F, for preferable usage with a subject of intermediate age (age 12 to 15) and a small sized device 11 may preferably be dimensioned and angled as shown in FIGS. 18G and 18H, for preferable usage with a subject of child age (age 8 to 11). Here, the benefits of using the angles and dimensions shown is the same as for the first embodiment described above, again all dimensions shown are in millimetres, and again, although preferable, all dimensions and angles shown are illustrative and non-limiting and other sizes and dimensions and angles may be used e.g. for different sized subjects.

Figure 19A:
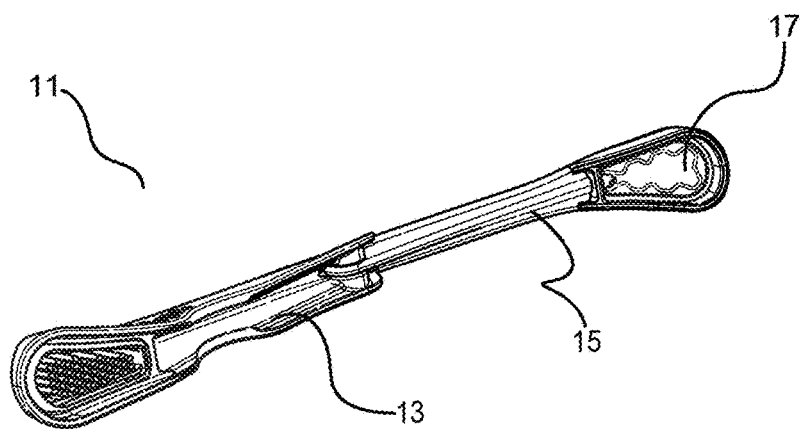
Figure 19B:
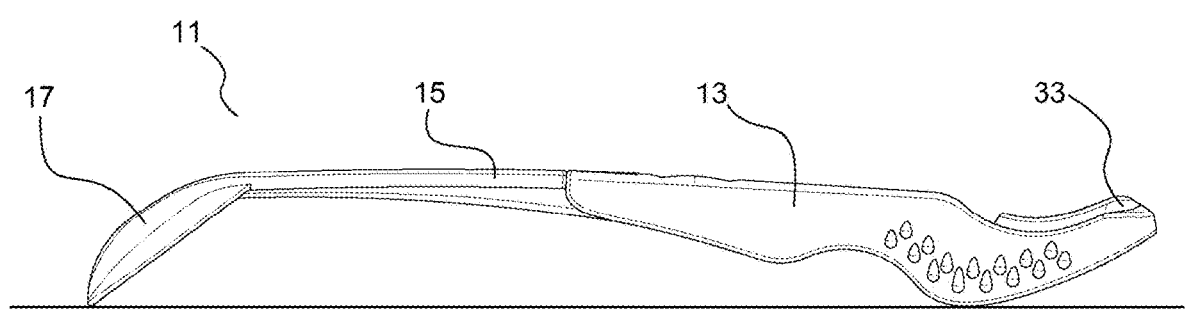
Figure 19C:
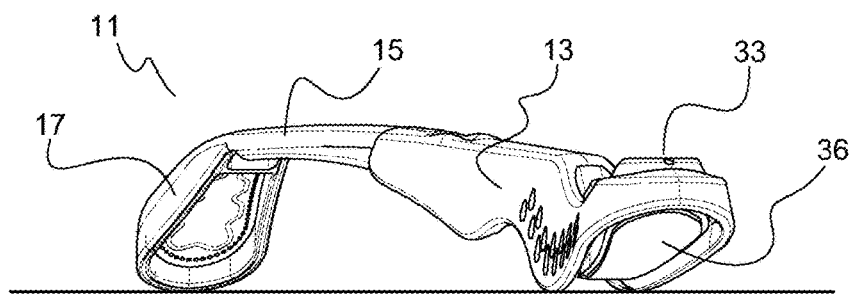
Figure 19D:
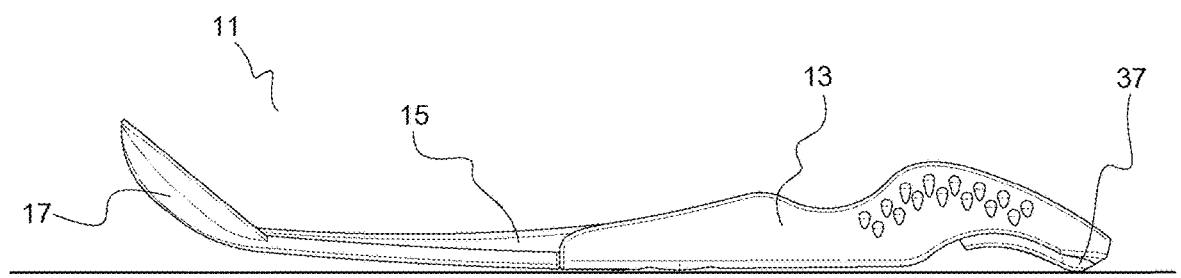
Figure 19E:
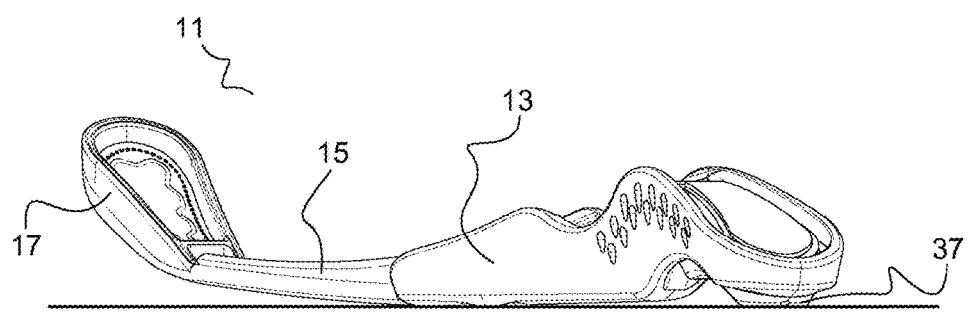

FIGS. 19A to 19E show various free standing positions of the sampling device 11 of the present embodiment. As shown in FIG. 19A, the sides of the handle 13, stem 15 and sampling head 17 are designed to allow the sampling head 17 to stay motionless when placed on its side, without rolling. FIGS. 19B and 19C show the device 11 in its unfolded/sampling condition, and placed on a level surface so as to rest on the sampling head 17 and sides of handle 13. FIGS. 19D and 19E shows the sampling device 11 placed on a level surface in an inverted condition, resting on a finger-grip portion of the handle 13 and the button provided by the bottom wall 37 of the washing and elution chamber 33, e.g. for insertion of a washing and elution buffer as explained below in connection with FIG. 21.

FIG. 20 shows the sampling device 11 of the present embodiment in a hand grip position for a user to conduct the sampling process described below in connection with FIG. 21.

Operation of the second embodiment of the sampling device, according to a second embodiment of a sampling method of the present invention, will now be described with reference to the flow chart of FIG. 21.

Firstly, in step 2101, and aided by the scalloped finger locators 57, a user pinches/pulls the stem 15 to open device 11 (see FIG. 22), and rotates the stem 15 and sampling head 17 relative to the handle 11, to click it into the fully unfolded sampling position.

In Step 2102, to reduce the risk of a gag-reflex, the back of the subject's throat is sprayed with lignocaine or other local anaesthetic. As will be appreciated, the order of steps 2101 and 2102 may be reversed, or these steps may be performed simultaneously e.g. by two clinicians working in tandem.

In step 2103, with the subject's mouth wide open, the sampling head 17 of the device 11 is inserted into the subject's mouth (see FIG. 23), taking care to avoid saliva contamination from the tongue. Although the device is useable on its own, for greater visibility of the mouth and throat, the device 11 may optionally be inserted whilst the subject's tongue is depressed using a suitable tongue depressor.

In step 2104, the sampling head 17 is used to deflect the subject's uvula, as necessary, until the device 11 is position centrally over the subject's airway (see FIG. 24, with the stem shown in cross-section and the handle omitted, for clarity) and the sampling head located at the desired sampling position namely over the vocal cords, within the oropharynx and posterior to the uvula of the subject.

In step 2105, the subject 3 is asked to cough or give a forced expiration (a sharp exhalation), thus allowing a sample of MLF to be collected by the sample collection membrane 23 located within the sampling head 17 of the device 11, uncontaminated (or with only minimal contamination) by saliva or other fluids.

In step 2106, the sampling device 11 is entirely removed from the subject's airway.

If the sample is to be stored for future sample preparation, the process proceeds to step 2107, in which the protective cover 46 is removed from the chamber 33, and the stem 15 and sampling head 17 are rotated towards the handle 13 until the closed condition is adopted, protecting the sample from extraneous contamination; the closed sampling device 11, including its collected sample, may then be frozen.

On the other hand, if a user wishes to directly wash and elute the sample, the process proceeds to step 2108. In this step, the protective cover 46 is again removed from the chamber 33, and elution buffer is introduced into the chamber 33 e.g. via a pipette P as shown in FIG. 25A. In the present embodiment, the chamber 33 has, merely as an example, a maximum capacity of 500 μl, although other sized chambers may of course be employed, as appropriate.

Figure 25B:
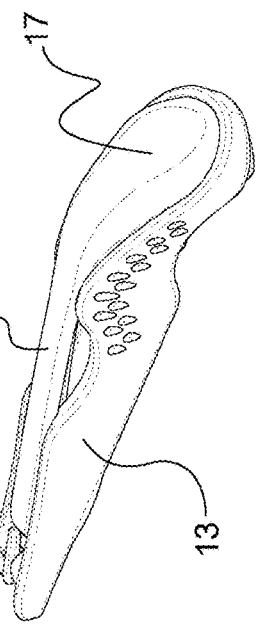

Next, in step 2109, the stem 15 and sampling head 17 are rotated towards the handle 13 to bring the device 11 into its fully folded condition (see FIG. 25B). As will be appreciated, the sample collection membrane 23 will now be located between the chevron-patterned protrusions of the sampling head 17 on one side, and the tops of the protruding columns 41 provided within the washing and elution chamber 33 on the other side.

Figure 26:
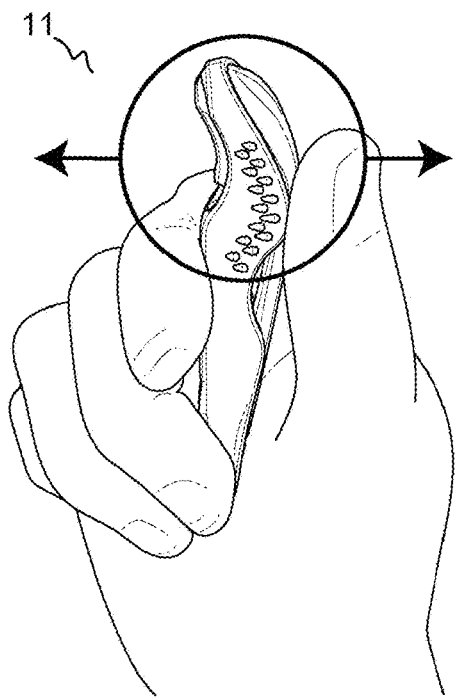

Next, in step 2110, the user shakes the folded device 11, causing the elution buffer to wash the sampling material 23 now located within the chamber (see FIG. 26). Here, the washing of the sample collection membrane 23 is facilitated by the fact that the elution buffer is able to travel freely around and between the columns 41 within the chamber and the chevron-patterned protrusions within the sampling head 17, thus readily exposing both sides of the sampling material of the sample collection membrane 23 to the elution buffer and hence maximising MLF capture from the sample collection membrane 23.

Figure 27A:
Figure 27B:
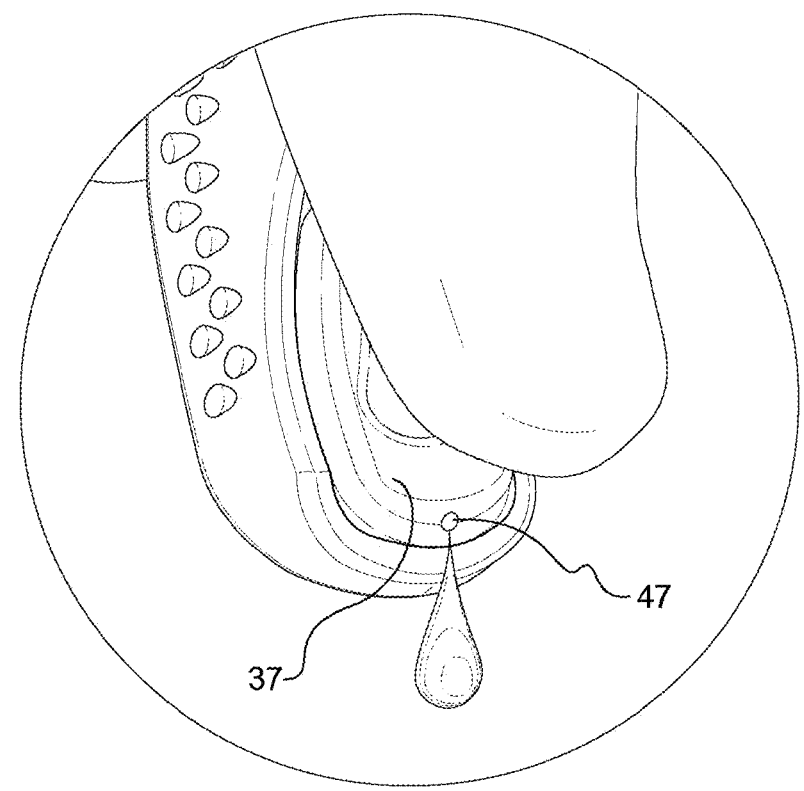

Next, in step 2111, the user orientates the device 11 with the circular weakened area 47 located over a suitable collection vessel V (see FIG. 27A).

Finally, in step 2112, the user squeezes the button defined by the bottom wall 37 of the chamber 33. The resultant pressure increase within the chamber 33 causes the weakened area 47 to rupture, ejecting the liquid contents (i.e. the elution buffer containing MLF washed from the sampling material) (see FIG. 27B) into the collection vessel V, e.g. for analysis or storage.

Hence, the process described above provides a user with a ready and convenient means of sample extraction. However, the sample extraction process of FIG. 21 is only one example, and other sample extraction processes are possible. Some exemplary alternative sample extraction process are described later. First, some further sampling device embodiments are described, in which like features are given the same reference numerals, and the discussion will focus only on the distinctions from the first and/or second embodiments of the sampling device described above.

Figure 28A:
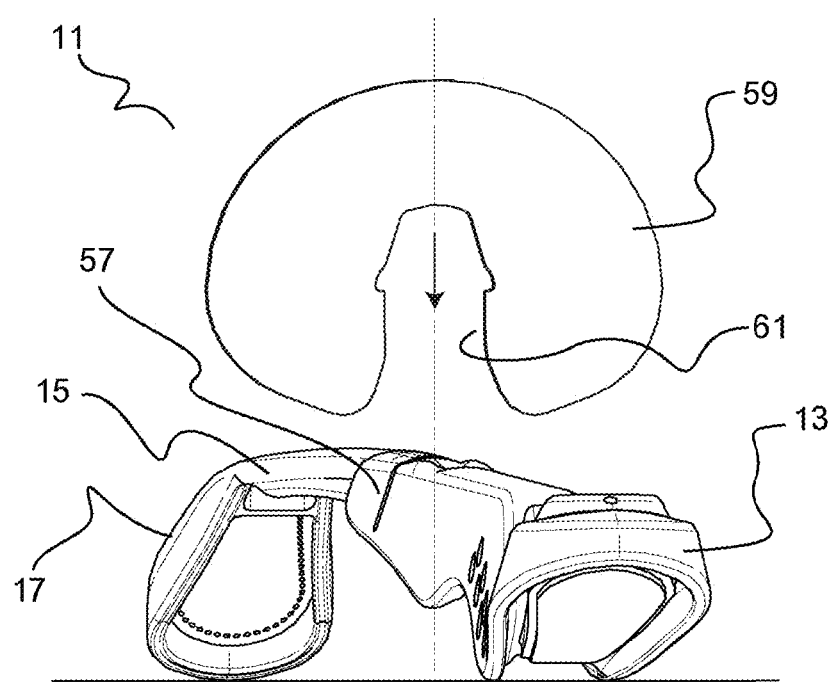
Figure 28C:
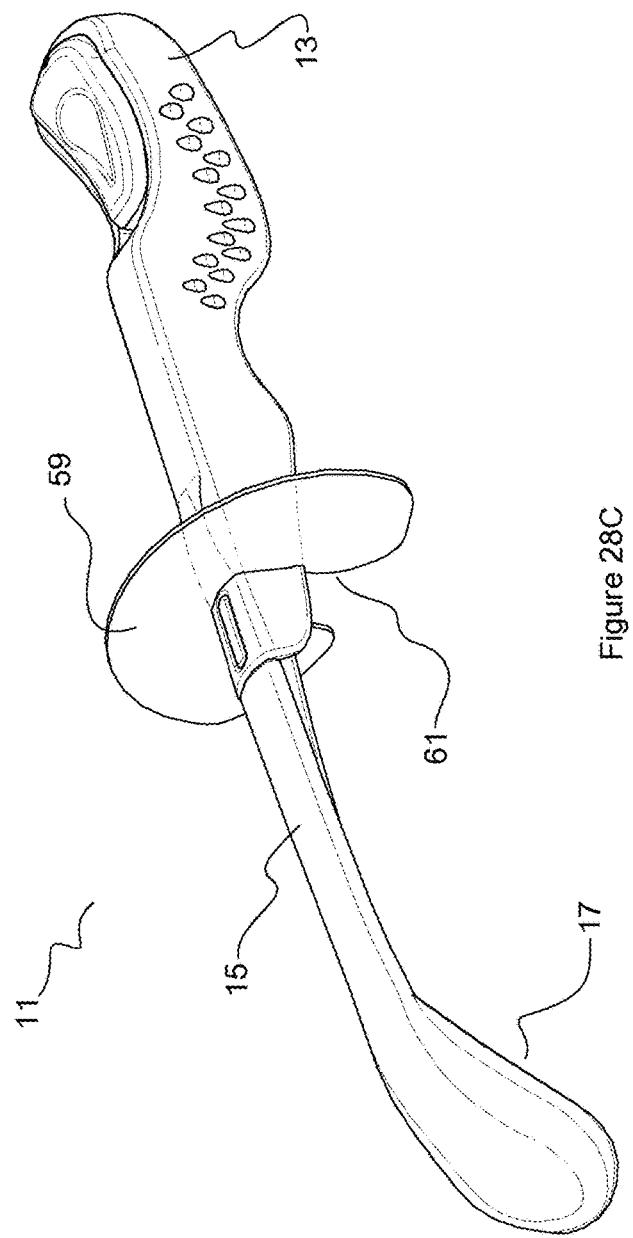
Figure 28B:
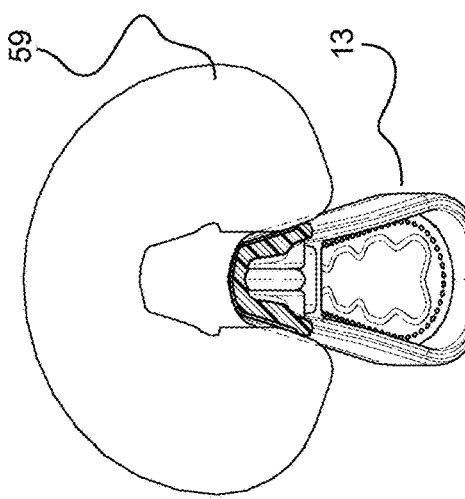
Figure 28D:
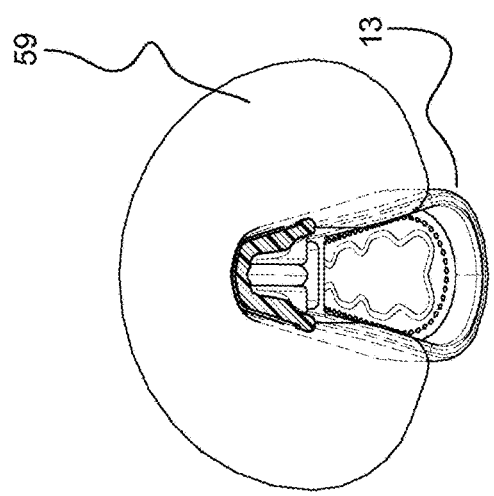
Figure 28E:
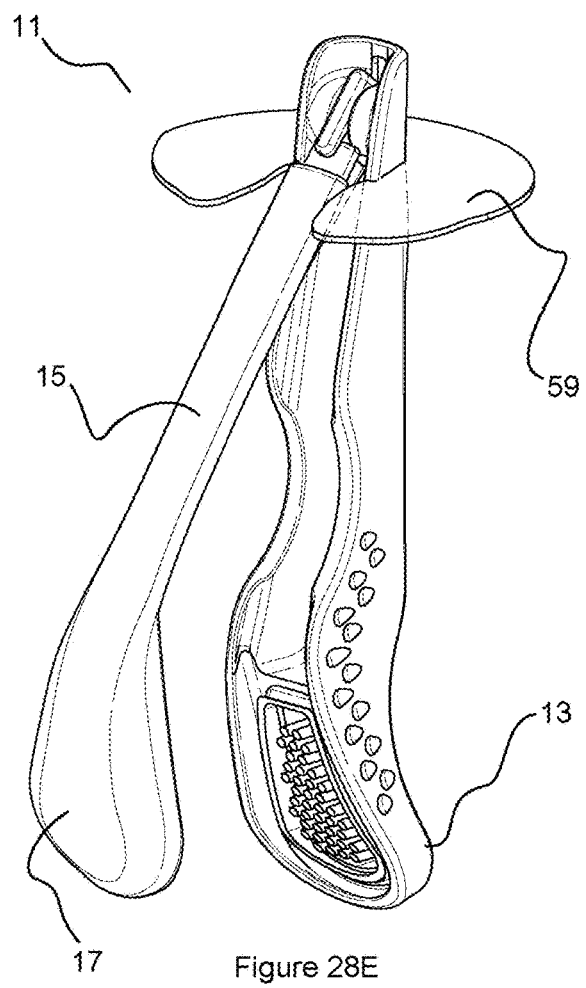
Figure 29A:
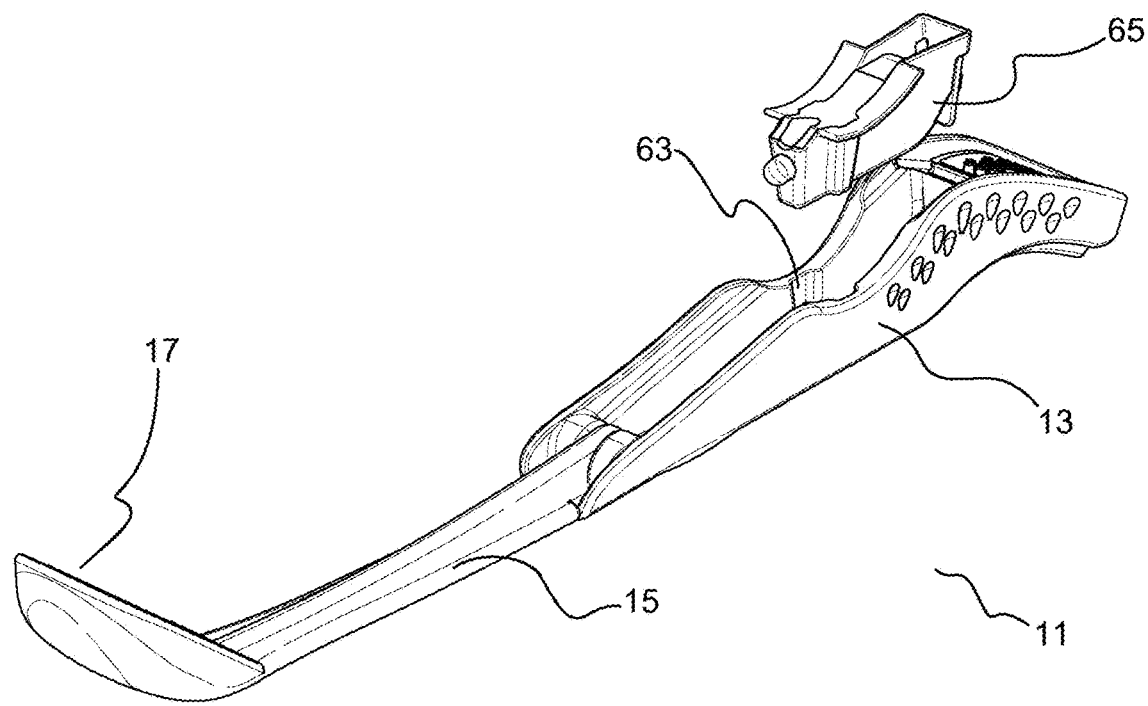
Figure 29B:
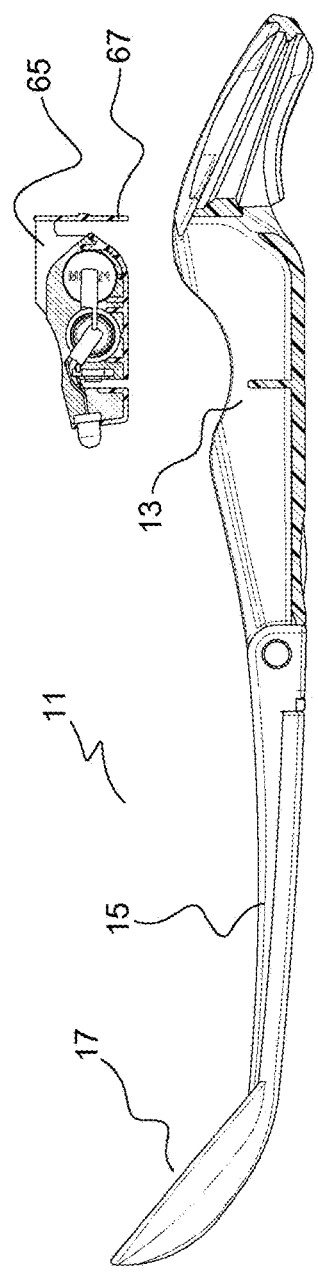
Figure 29C:
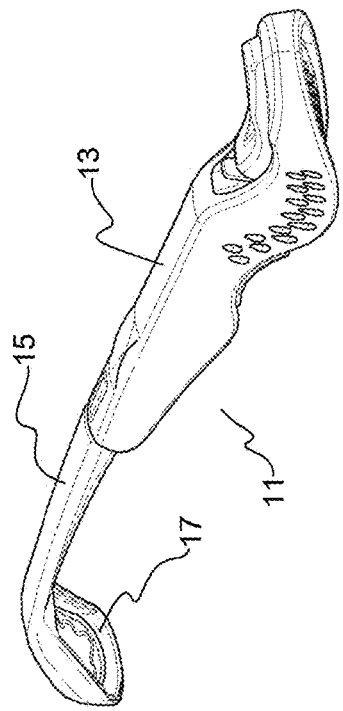
Figure 29D:
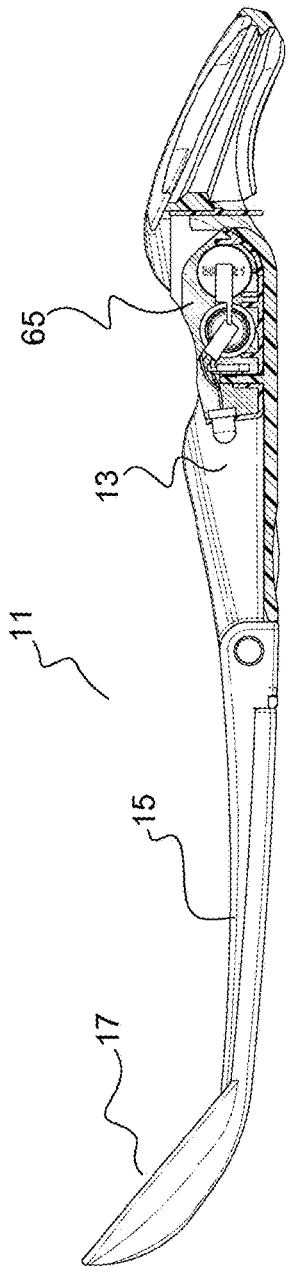

A third embodiment of a sampling device 11 is shown in FIGS. 28A to 28E. The sampling device 11 of the present embodiment is very similar to the second embodiment described above, but is additionally provided with a transverse slot or groove 57, located forward (i.e. towards the sampling head end) of the finger locator 14 of the handle, into which a generally circular cough shield 59 is located (as shown in FIGS. 28A and 28B) to form the completed device 11 shown in FIGS. 28C and 28D. The third embodiment is otherwise the same as the second embodiment.

The cough shield 59 is preferably made from a thin sheet of plastics material (e.g. Polyethylene Terephthalate Glycol (PETG) or Polycarbonate (PC)) although other suitable materials (e.g. metals) may be used, as appropriate. In the present embodiment, the cough shield 59 offers a user ≅315° protective coverage from the cough cloud generated by the subject during airway sampling, with the remaining ≅45° of the cough cloud passing underneath the winged sides of the handle. A slot 61 is provided in the cough shield 59, offering sufficient clearance for the sampling head 17 to be freely rotated between the folded and unfolded conditions of the sampling device 11 (see FIG. 28E).

As will be appreciated, the first embodiment of a sampling device 11 described above may likewise be modified to similarly include a cough shield 59, locating into a slot 57 to be provided, according to this modification, in the handle of the device 11.

A fourth embodiment of a sampling device 11 is shown in FIGS. 29 and 30. This embodiment modifies the second embodiment described above, to include an illumination module 65 within the handle 13, and to configure the stem 15 and sampling head 17 as a light guide device, beneficially allowing for the interior of a subject's mouth to be illuminated to facilitate the correct positioning of the sampling device 11 during the sampling process.

In more detail, and as shown in the various parts of FIG. 29, the stem 15 and sampling head 17 of the present embodiment are formed from a suitable light-transmissive material or materials so as to act as a light guide. For example, the stem 15 and sampling head 17 of the present embodiment may be formed from optically clear thermoplastic styrene-butadiene copolymers (SBC) or optically clear polycarbonates (PC) which are designed to glow with light from an external light source.

Next, the handle 13 of the present device is adapted to include a location groove 63 (see FIG. 29A) for accommodating an illumination module 65. In the present embodiment, the illumination module 65 includes a snap hook 67 (see FIG. 29b), and the handle 13 further comprises a snaphook hole (not shown) to receive the same, to securely retain the illumination module 65 in the handle 13 (see FIGS. 29C and 29D). In the present embodiment, the snap hook 67 may be disengaged from the snaphook hole, allowing the illumination module 65 to be removed for insertion into one or more other sampling devices 11; that is, one illumination module 65 may be re-used (after appropriate cleansing) and shared amongst a plurality of different illuminated sampling devices 11. The illumination module 65 is sealed against liquid and dirt ingress and for example may be constructed with an ABS moulded housing, with the necessary electronics potted in place using e.g. a TPE overmoulding process.

Preferably, the illumination module 65 may include a switch 71, which may be actuated by a light activating spigot optionally provided within the handle 13. This arrangement may for example allow for the light to be automatically switched on when the illumination module 65 is inserted into the handle 13 and switched off when the illumination module 65 is removed from the handle 13. Alternatively, the switch 71 may allow for the light to be automatically switched on when the sampling device 11 is brought into its unfolded (sampling) condition, and switched off when the sampling device 11 is in the folded condition. Alternatively, a manual on/off switch may be provided for manual activation by a user.

As for the illumination module 65, any suitable illumination device may be employed, but for example these may include e.g.:

1) A laser light source, for example a laser with a wavelength between 450-500 nm (blue-cyan).
2) An LED light source, for example an Ultrabright White directional LED.

Figure 30A:
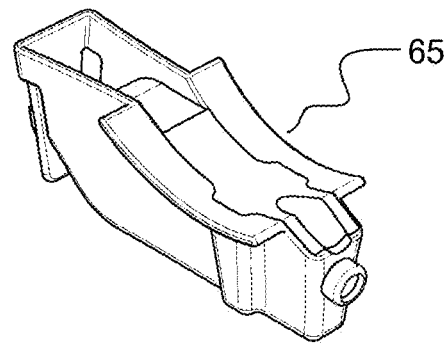
Figure 30B:
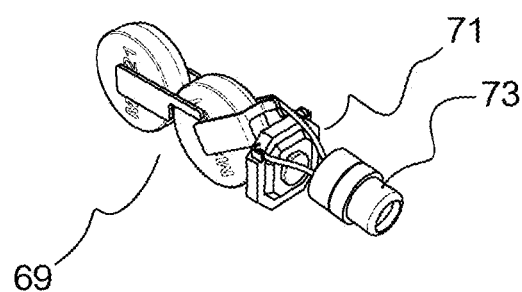

An example of a laser light source is shown in FIG. 30A, with the light emitting element shown in detail in FIG. 30B. The latter may include, for example, a suitable power supply 69 such as two 3 Volt batteries wired in parallel, for example 5.5 mAh Lithium Manganese Silicon Batteries having Dimensions ø6.8 mm, 2.1 mm thick (Part number: MS621). Also shown in FIG. 30B is a low profile, tactile, surface mount switch 71 e.g. for automatic activation by a light activating spigot optionally provided within the handle 11 as described above. The light emitting element further comprises a laser diode 73, for example a 3.3 mm laser diode with driver module.

Figure 31A:
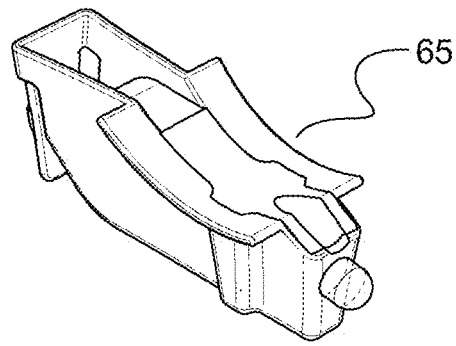
Figure 31B:
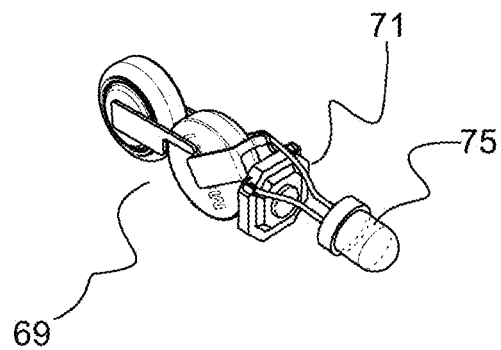

An example of an LED light source is shown in FIG. 31A, with the light emitting element shown in detail in FIG. 31B. The latter may include, for example, a suitable power supply 69 such as two 1.55 Volt batteries wired in series, for example 16 mAh Silver Oxide Batteries having dimensions ø6.8 mm, 1.65 mm thick (Part number: SR65). Also shown in FIG. 31B is a low profile, tactile, surface mount switch 71 e.g. for automatic activation by a light activating spigot optionally provided within the handle, as described above. The light emitting element further comprises an LED light source 75, for example a 3 mm ultra bright directional LED.

In the same way that the second embodiment may be modified to include an illumination feature, according to a fifth embodiment of the present invention, the first embodiment of the sampling device 11 described above may also be modified as shown in FIG. 32 to include a light module 65 within the handle 13, beneficially allowing for the interior of a subject's mouth to be illuminated to facilitate the correct positioning of the sampling device 11 during the sampling process. In this embodiment, as it is provided integrally with the sampling head 17 and stem 15 of the device 11, the handle 13 is also configured as a light guide device. In particular, the integral handle 13, stem 15 and sampling head 17 of the present embodiment are preferably formed from a suitable light-transmissive material or materials so as to act as a light guide. For example, the handle 13, stem 15 and sampling device 17 of the present embodiment may be integrally formed from optically clear thermoplastic styrene-butadiene copolymers (SBC) or optically clear polycarbonates (PC) which are designed to glow with light from the illumination module 65.

As the present fifth embodiment (like the first embodiment) does not have a folding function, a light activating spigot is not provided in the handle 11. However, a manual light switch is provided for activation by a user, so as to switch on the illumination device during the sampling process. In other respects, such as the nature of the illumination module, the fifth embodiment may generally be the same as for the fourth embodiment described above, and hence is not re-described here.

It will be appreciated that, according to further embodiments of the present invention, the cough shield feature of the third embodiment may also be combined with the fourth and fifth embodiments having the light guide feature.

The following describes some alternative sample extraction methods, suitable for usage with embodiments of the sampling device having a washing and elution chamber (e.g. the second, third and fourth embodiments described above).

According to a further embodiment of a sample extraction method, as shown in FIG. 33, rather than a user squeezing the chamber to cause rupture of the weakened area, a user may instead extract the liquid content (elution buffer containing MLF) by inserting a needle N of a syringe S into the weakened area, and pulling back on the plunger of the syringe to extract the sample. The extracted sample may then be processed as desired e.g. ejected from the syringe into a suitable vessel for direct analysis or transferred into a cryogenic storage container and frozen.

According to a still further embodiment of a sample extraction method, as shown in FIG. 34, a centrifuge method may for example be employed. According to this embodiment, after conducting the sample gathering process, introducing elution buffer introduced into the chamber and placing the sampling device into its folded condition, a user places the sampling device into a suitable centrifuge tube T (e.g. a cryogenic 50 ml centrifuge tube), with the tube then being closed by a cap C. The centrifuge tube is then located into a suitable centrifuge, which is then operated to spin the centrifuge tube e.g. to spin-down for 30 seconds @ 4000 rpm. This causes the weakened area to rupture, so that the liquid contents (elution buffer containing sampled MLF) collect at the bottom of the centrifuge tube T. A user then removes the cap from the tube, removes the device, and re-caps the tube e.g. for freezing or analysis.

The embodiments described above relate to airway sampling from a human subject. However, this is merely exemplary, and according to further embodiments the present invention may instead be applied to sampling devices and associated sampling methods for airway sampling performed on non-human subjects e.g. livestock such as cattle or pets such as cats and dogs.

The embodiments above assume that a user e.g. a nurse, doctor or other clinician would take a sample from a subject. However, potentially, a subject may take a sample from themselves, in which case the "user" and the "subject" are the same person.

The foregoing description has been given by way of example only and it will be appreciated by a person skilled in the art that modifications can be made without departing from the scope of the present invention as defined by the claims.

The invention claimed is:

1. An airway sampling device for taking a sample from a subject's airway, the device comprising:
   a handle to be gripped by a user when taking the sample, and
   a sampling head carried by the handle, the sampling head comprising a cavity with an opening for entry by the sample and a sample collection membrane located within the cavity for receiving the sample,
   wherein the sampling head is provided with a wrap-around hood which encloses the sample collection membrane on all sides, including on lateral sides of the sampling head and on a leading side of the sampling head opposite to the handle, such that the sample collection membrane is enclosed on all sides other than at the opening to the cavity within the hood to enable the sampling head to push past the tonsils of the subject, to deflect the uvula of the subject, and potentially to also contact the back of the subject's throat, without any fluid contamination of the sample collection membrane.

2. The airway sampling device according to claim 1, wherein the sample collection membrane comprises absorbent and/or adsorbent material.

3. The airway sampling device according to claim 1, wherein the sample collection membrane is detachable from the sampling head.

4. The airway sampling device according to claim 1, wherein the cavity has a gutter provided at least partly around its opening.

5. The airway sampling device according to claim 1, wherein the cavity is defined within a peripheral wall which creates the wrap-around hood, and wherein an outer surface of the peripheral wall is configured to be perpendicular to the tonsils of the subject when the sampling head is inserted into and/or removed from the subject's pharynx.

6. The airway sampling device according to claim 5, wherein the outer surface of the peripheral wall is further configured to be perpendicular to the uvula and/or posterior wall of the oropharynx of the subject during capture of the sample from a sampling position in the patient's airway at which the opening of the cavity is located over the vocal cords and within the oropharynx posterior to the uvula of the subject.

7. The airway sampling device according to claim 6, wherein an outer surface of the peripheral wall is configured to deflect the uvula of the subject, allowing the sampling head to enter the pharynx from the oral cavity.

8. The airway sampling device according to claim 1, wherein the handle is provided with a chamber, and the sampling head is movable relative to the handle between a first condition in which the sampling head is distal from the handle and a second condition in which the cavity is located over the chamber to define an enclosure which encloses the sample collection membrane between the cavity and the chamber.

9. The airway sampling device according to claim 8, wherein the enclosure is fluid-tight.

10. The airway sampling device according to claim 8, wherein a weakened area is provided in one of the chamber or the cavity.

11. The airway sampling device according to claim 10, wherein the weakened area is configured to rupture when pressure is applied to the enclosure.

12. The airway sampling device according to claim 11, wherein the weakened area is provided in the chamber, and the chamber is formed from a deformable material to allow a user to apply pressure to the enclosure.

13. The airway sampling device according to claim 8, wherein the interior of the chamber is provided with one or more protrusions which contact the sample collection membrane when the sampling head is placed into its second condition.

14. The airway sampling device according to claim 1, wherein the interior of the cavity is provided with one or more protrusions on which the sample collection membrane is located.

15. The airway sampling device according to claim 1, wherein the sampling device further comprises an illumination module, and the sampling head is configured as a light guide to guide and emit light emitted from the illumination module.

16. The airway sampling device according claim 15, wherein the illumination module is removably mounted on the sampling device.

17. The airway sampling device according to claim 1, wherein the sampling head is provided at a first end of the sampling device distal from a second end of the sampling device at which the handle is provided, and the sampling device further comprises a shield mounted between the first and second ends of the sampling device, for shielding the user from sample from the subject.

18. The airway sampling device according to claim 1, wherein the airway sampling device is shaped and dimensioned so as to locate the opening of the cavity over the vocal cords and within the oropharynx posterior to the uvula of a subject when the sampling head is located at a sampling position in the patient's airway for taking the sample.

19. The airway sampling device according to claim 1, wherein the sampling head is angled relative to the handle, so as to present a plane of the opening of the cavity at an angle of between 25° to 45° downwardly from horizontal when the sampling head is located at a sampling position in the patient's airway at which the opening of the cavity is located over the vocal cords and within the oropharynx posterior to the uvula of the subject, with the subject upright.

20. The airway sampling device according to claim 1, wherein a depth of the sampling device, from an uppermost surface of the handle to a lowermost tip of the sampling head, is from 17 mm to 23 mm.

21. The airway sampling device according to claim 1, wherein a maximum width of the sampling head is between 10 mm to 16 mm.

22. A method of taking a sample from a subject's airway using the airway sampling device of claim 1, the method comprising:
(i) inserting the airway sampling device of any one of the preceding claims into the subject's airway so as to position the sampling head at a sampling position located above the vocal cords and within the oropharynx and posterior to the uvula of the subject;
(ii) prompting the subject to cough or give a forcible expiration to produce the sample, which sample is collected by the sampling head; and
(iii) removing the sampling device from the subject's airway.

23. The method of claim 22, further comprising exposing the sample collection membrane to an elution buffer to elute the sample into the elution buffer.

* * * * *